United States Patent [19]

Bochis et al.

[11] Patent Number: 5,283,241

[45] Date of Patent: Feb. 1, 1994

[54] BENZO-FUSED LACTAMS PROMOTE RELEASE OF GROWTH HORMONE

[75] Inventors: Richard J. Bochis, East Brunswick; Matthew J. Wyvratt, Mountainside; William R. Schoen, Edison, all of N.J.

[73] Assignee: Merck & Co., Inc., Rahway, N.J.

[21] Appl. No.: 936,975

[22] Filed: Aug. 28, 1992

[51] Int. Cl.$^5$ .................... A61K 31/55; C07D 209/34; C07D 215/227; C07D 223/16

[52] U.S. Cl. ..................... 514/183; 514/213; 514/312; 514/418; 540/455; 540/460; 540/461; 540/491; 540/509; 540/523; 544/52; 544/105; 544/354; 546/158; 548/483

[58] Field of Search ............... 540/461, 523; 546/158; 548/483; 514/183, 213, 312, 418

[56] References Cited

U.S. PATENT DOCUMENTS

| | | | |
|---|---|---|---|
| 3,239,345 | 3/1966 | Hodge et al. | 514/450 |
| 4,036,979 | 7/1977 | Asato | 514/443 |
| 4,411,890 | 10/1983 | Momany | 514/17 |
| 4,692,522 | 9/1987 | Parsons et al. | 540/461 |
| 5,206,235 | 4/1993 | Fisher et al. | 540/523 |

FOREIGN PATENT DOCUMENTS

| | | |
|---|---|---|
| 166357 | 1/1986 | European Pat. Off. |
| 253310 | 1/1988 | European Pat. Off. |
| 291969 | 11/1988 | European Pat. Off. |
| 324377 | 7/1989 | European Pat. Off. |
| 349949 | 1/1990 | European Pat. Off. |

OTHER PUBLICATIONS

Jones, et al. J. Chem. Soc. c pp. 2176–2181 (1969).
Davis, et al., Arch. Biochem. Biophys 102 pp. 48–51 (1963).
Wattley, et al. J. Med. Chem. 28 pp. 1511–1516 (1985).
Slade, et al. J. Med. Chem. 28 pp. 1517–1521 (1985).
Huang, et al. Synthesis, 10 p. 851 (1984).
Stewart, Australia J. Chem. 33 pp. 633–640 (1980).
Still, et al. J. Org. Chem. 43, p. 2923 (1978).
Parsons, W. H., Med. Chem. vol. 32 pp. 1681–1685 (1989).

Primary Examiner—John M. Ford
Assistant Examiner—Philip F. Datlow
Attorney, Agent, or Firm—David L. Rose; Joseph F. DiPrima

[57] ABSTRACT

There are disclosed certain novel compounds identified as benzo-fused lactams which promote the release of growth hormone in humans and animals. This property can be utilized to promote the growth of food animals to render the production of edible meat products more efficient, and in humans, to increase the stature of those afflicted with a lack of a normal secretion of natural growth hormone. The compounds are prepared by substitution of an amino-lactam with a substituted amide function. Growth promoting compositions containing such benzo-fused lactams as the active ingredient thereof are also disclosed.

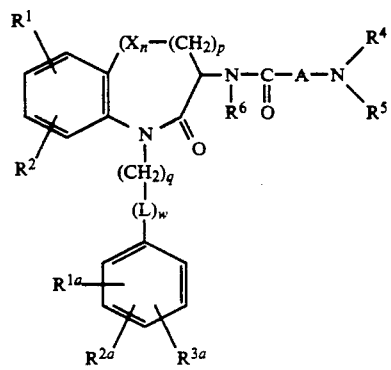

Where L is

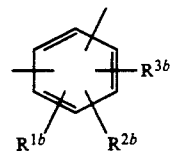

8 Claims, No Drawings

BENZO-FUSED LACTAMS PROMOTE RELEASE OF GROWTH HORMONE

BACKGROUND OF THE INVENTION

Growth hormone, which is secreted from the pituitary, stimulates growth of all tissues of the body that are capable of growing. In addition, growth hormone is known to have the following basic effects on the metabolic process of the body:

1. Increased rate of protein synthesis in all cells of the body.
2. Decreased rate of carbohydrate utilization in cells of the body;
3. Increased mobilization of free fatty acids and use of fatty acids for energy.

A deficiency in growth hormone secretion can result in various medical disorders, such as dwarfism.

Various ways are known to release growth hormone. For example, chemicals such as arginine, L-3,4-dihydroxyphenylalanine (L-DOPA), glucagon, vasopressin, and insulin induced hypoglycemia, as well as activities such as sleep and exercise, indirectly cause growth hormone to be released from the pituitary by acting in some fashion on the hypothalamus perhaps either to decrease somatostatin secretion or to increase the secretion of the known secretagogue growth hormone releasing factor (GRF) or an unknown endogenous growth hormone-releasing hormone or all of these.

In cases where increased levels or growth hormone were desired, the problem was generally solved by providing exogenous growth hormone or by administering an agent which stimulated growth hormone production and/or release. In either case the peptidyl nature of the compound necessitated that it be administered by injection. Initially the source of growth hormone was the extraction of the pituitary glands of cadavers. This resulted in a very expensive product and carried with it the risk that a disease associated with the source of the pituitary gland could be transmitted to the recipient of the growth hormone. Recently, recombinant growth hormone has become available which, while no longer carrying any risk of disease transmission, is still a very expensive product which must be given by injection or by a nasal spray.

Other compounds have been developed which stimulate the release of endogenous growth hormone such as analogous peptidyl compounds related to GRF or the peptides of U.S. Pat. No. 4,411,890. These peptides, while considerably smaller than growth hormones are still susceptible to various proteases. As with most peptides, their potential for oral bioavailability is low. The instant compounds are bon-peptidyl agents for promoting the release of growth hormone which may be administered parenterally, nasally or by the oral route.

SUMMARY OF THE INVENTION

The instant invention covers certain benzo-fused lactam compounds which have the ability to stimulate the release of natural or endogenous growth hormone. The compounds thus have the ability to be used to treat conditions which require the stimulation of growth hormone production or secretion such as in humans with a deficiency of natural growth hormone or in animals used for food production where the stimulation of growth hormone will result in a larger, more productive animal. Thus, it is an object of the instant invention to describe the benzo-fused lactam compounds. It is a further object of this invention to describe procedures for the preparation of such compounds. A still further object is to describe the use of such compounds to increase the secretion of growth hormone in humans and animals. A still further object of this invention is to describe compositions containing the benzo-fused lactam compounds for the use of treating humans and animals so as to increase the level of growth hormone secretions. Further objects will become apparent from a reading of the following description.

DESCRIPTION OF THE INVENTION

The novel benzo-fused lactams of the instant invention are best described in the following structural formula I:

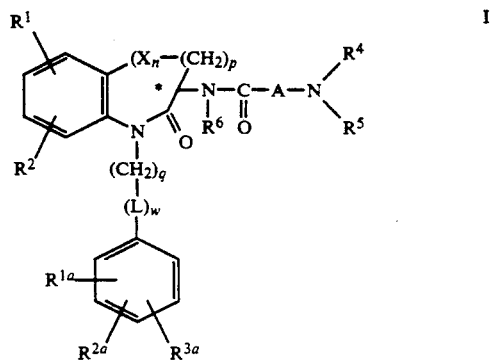

where L is

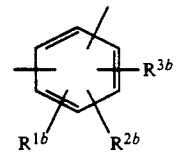

n is 0 or 1;
p is 0 to 3;
q is 0 to 4;
w is 0 or 1;
X is C=O, O, S(O)$_m$,

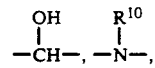

—CH=CH—;
m is 0 to 2;
$R^1$, $R^2$, $R^{1a}$, $R^{2a}$, $R^{1b}$, and $R^{2b}$ are independently hydrogen, halogen, $C_1$-$C_7$ alkyl, $C_1$-$C_3$ perfluoroalkyl, $C_1$-$C_3$ perfluoroalkoxy, —S(O)$_m$R$^{7a}$, cyano, nitro, $R^{7b}$O(CH$_2$)$_v$—, $R^{7b}$COO(CH$_2$)$_v$—, $R^{7b}$OCO(CH$_2$)$_v$, $R^4R^5$N(CH$_2$)$_v$—, $R^{7b}$CON(R$^4$)(CH$_2$)$_v$—, $R^4R^5$NCO(CH$_2$)$_v$—, phenyl or substituted phenyl where the substituents are from 1 to 3 of halogen, $C_1$-$C_6$ alkyl, $C_1$-$C_6$ alkoxy, or hydroxy; $R^{7a}$ and $R^{7b}$ are independently hydrogen, $C_1$-$C_3$ perfluoroalkyl, $C_1$-$C_6$ alkyl, substituted $C_1$-$C_6$ alkyl, where the substituents are phenyl or substituted phenyl; phenyl or substituted phenyl where the phenyl substituents are from 1 to 3 of halogen. $C_1$-$C_6$ alkyl, $C_1$-$C_6$ alkoxy, or hydroxy and v is 0 to 3; $R^{3a}$ and $R^{3b}$ are independently hydrogen, $R^9$, $C_1$-$C_6$ alkyl substituted with $R^9$, phenyl substituted with $R^9$, or phenoxy substituted with $R^9$ with the proviso that either $R^{3a}$ or $R^{3b}$ must be a substituent other than hydrogen;

$R^9$ is: $R^{4b}R^{12a}NCON(R^{12b})(CH_2)_v$—, $R^{4b}R^{12a}NCSN(R^{12b})(CH_2)_v$—, $R^{4b}R^{12a}NN(R^{12b})CSN(R^{12c})(CH_2)_v$—, $R^{4b}R^{12a}NN(R^{12b})CON(R^{12c})(CH_2)_v$—, $R^{4b}R^{12a}NN(R^{12b})COO(CH_2)_v$—, $R^{4b}R^{12a}NCOO(CH_2)_v$— or $R^{13}OCON(R^{12b})(CH_2)_v$—, where v is 0 to 3.

$R^{12a}$, $R^{12b}$ and $R^{12c}$ are independently $R^{5a}$, $OR^{5a}$, or $COR^{5a}$. $R^{12a}$ and $R^{12b}$, or $R^{12b}$ and $R^{12c}$, or $R^{13}$ and $R^{12b}$, or $R^{12a}$ and $R^{4b}$ can be taken together to form —$(CH_2)_r$—B—$(CH_2)_s$— where B is $CHR^1$, O, $S(O)_m$ or $NR^{10}$, m is 0, 1 or 2, r and s are independently 0 to 3 and $R^1$ and $R^{10}$ are as defined.

$R^{13}$ is: $C_1$-$C_3$ perfluoroalkyl, $C_1$-$C_6$ alkyl, substituted $C_1$-$C_6$ alkyl, where the substituents are hydroxy, $NR^{10}R^{11}$, carboxy, phenyl or substituted phenyl; phenyl or substituted phenyl where the substituents on the phenyl are from 1 to 3 of halogen, $C_1$-$C_6$ alkyl, $C_1$-$C_6$ alkoxy or hydroxy.

and v is as defined above;

$R^4$, $R^{4b}$, $R^5$ and $R^{5a}$ are independently hydrogen, phenyl, substituted phenyl, $C_1$-$C_{10}$ alkyl, substituted $C_1$-$C_{10}$ alkyl, $C_3$-$C_{10}$ alkenyl, substituted $C_3$-$C_{10}$ alkenyl, $C_3$-$C_{10}$ alkynyl, or substituted $C_3$-$C_{10}$ alkynyl where the substituents on the phenyl, alkyl, alkenyl or alkynyl are from 1 to 5 of hydroxy, $C_1$-$C_6$ alkoxy, $C_3$-$C_7$ cycloalkyl, fluoro, $R^1$ substituted or $R^1$, $R^2$ independently disubstituted phenyl $C_1$-$C_3$ alkoxy, $R^1$ substituted or $R^1$, $R^2$ independently disubstituted phenyl, $C_1$-$C_{20}$-alkanoyloxy, $C_1$-$C_5$ alkoxycarbonyl, carboxy, formyl, or —$NR^{10}R^{11}$ where $R^{10}$ and $R^{11}$ are independently hydrogen, $C_1$-$C_6$ alkyl, phenyl, phenyl $C_1$-$C_6$ alkyl, $C_1$-$C_5$-alkoxycarbonyl, or $C_1$-$C_5$-alkanoyl-$C_1$-$C_6$ alkyl; or $R^4$ and $R^5$ can be taken together to form —$(CH_2)_r$B$(CH_2)_s$— where B is $CHR^1$, O, $S(O)_m$ or N—$R^{10}$, r and s are independently 1 to 3 and $R^1$ and $R^{10}$ are as defined above;

$R^6$ is hydrogen, $C_1$-$C_{10}$ alkyl, phenyl or phenyl $C_1$-$C_{10}$ alkyl;

A is

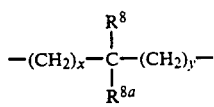

where x and y are independently 0-3;

$R^8$ and $R^{8a}$ are independently hydrogen, $C_1$-$C_{10}$ alkyl, trifluoromethyl, phenyl, substituted $C_1$-$C_{10}$ alkyl where the substituents are from 1 to 3 of imidazolyl, indolyl, hydroxy, fluoro, $S(O)_mR^{7a}$, $C_1$-$C_6$ alkoxy, $C_3$-$C_7$ cycloalkyl, $R^1$ substituted or $R^1$, $R^2$ independently disubstituted phenyl $C_1$-$C_3$ alkoxy, $R^1$ substituted or $R^1$, $R^2$ independently disubstituted phenyl, $C_1$-$C_5$-alkanoyloxy, $C_1$-$C_5$ alkoxycarbonyl, carboxy, formyl, or —$NR^{10}R^{11}$ where $R^{10}$ and $R^{11}$ are as defined above; or $R^8$ and $R^{8a}$ can be taken together to form —$(CH_2)_t$— where t is 2 to 6; and $R^8$ and $R^{8a}$ can independently be joined to one or both of $R^4$ and $R^5$ to form alkylene bridges between the terminal nitrogen and the alkyl portion of the A group wherein the bridge contains from 1 to 5 carbon atoms; and pharmaceutically acceptable salts thereof.

In the above structural formula and throughout the instant specification, the following terms have the indicated meanings:

The alkyl groups specified above are intended to include those alkyl groups of the designated length in either a straight or branched configuration. Exemplary of such alkyl groups are methyl, ethyl, propyl, isopropyl, butyl, sec-butyl, tertiary butyl, pentyl, isopentyl, hexyl, isohexyl, and the like.

The alkoxy groups specified above are intended to include those alkoxy groups of the designated length in either a straight or branched configuration. Exemplary of such alkoxy groups are methoxy, ethoxy, propoxy, isopropoxy, butoxy, isobutoxy, tertiary butoxy, pentoxy, isopentoxy, hexoxy, isohexoxy and the like.

The term "halogen" is intended to include the halogen atom fluorine, chlorine, bromine and iodine.

Certain of the above defined terms may occur more than once in the above formula and upon such occurrence each term shall be defined independently of the other.

Preferred compounds of the instant invention are realized when in the above structural formula:

n is 0 or 1;
p is 0 to 3;
q is 0 to 2;
w is 0 or 1;
X is O, $S(O)_m$,

m is 0 to 2;

$R^1$, $R^2$, $R^{1a}$, $R^{2a}$, $R^{1b}$, and $R^{2b}$ are independently hydrogen, halogen, $C_1$-$C_7$ alkyl, $C_1$-$C_3$ perfluoroalkyl, —$S(O)_mR^{7a}$, $R^{7b}O(CH_2)_v$—, $R^{7b}COO(CH_2)_v$—, $R^{7b}OCO(CH_2)_v$—, phenyl or substituted phenyl where the substituents are from 1 to 3 of halogen, $C_1$-$C_6$ alkyl, $C_1$-$C_6$ alkoxy, or hydroxy;

$R^{7a}$ and $R^{7b}$ are independently hydrogen, $C_1$-$C_3$ perfluoroalkyl, $C_1$-$C_6$ alkyl, substituted $C_1$-$C_6$ alkyl, where the substituents are phenyl; phenyl and v is 0 to 2;

$R^{3a}$ and $R^{3b}$ are independently hydrogen, $R^9$, $C_1$-$C_6$ alkyl substituted with $R^9$, phenyl substituted with $R^9$, or phenoxy substituted with $R^9$ with the proviso that either $R^{3a}$ or $R^{3b}$ must be a substituent other than hydrogen;

$R^9$ is: $R^{4b}R^{12a}NCON(R^{12b})(CH_2)_v$—, $R^{4b}R^{12a}NCSN(R^{12b})(CH_2)_v$—, $R^{4b}R^{12a}NN(R^{12b})CON(R^{12c})(CH_2)_v$—, $R^{4b}R^{12a}NN(R^{12b})COO(CH_2)_v$—, $R^{4b}R^{12a}NCOO(CH_2)_v$— or $R^{13}OCON(R^{12b})(CH_2)_v$—, where v is 0 to 3.

$R^{12a}$, $R^{12b}$ and $R^{12c}$ are independently $R^{5a}$, $OR^{5a}$, or $COR^{5a}$; $R^{12a}$ and $R^{12b}$, or $R^{12b}$ and $R^{12c}$, or $R^{13}$ and $R^{12b}$ or $R^{12a}$ and $R^{4b}$ can be taken together to form —$(CH_2)_r$—B—$(CH_2)_s$—where B is $CHR^1$, O, $S(O)_m$ or $NR^{10}$, m is 0, 1 or 2, r and s are independently 0 to 3, $R^1$ is as defined above and $R^{10}$ is hydrogen, $C_1$-$C_6$ alkyl, phenyl $C_1$-$C_6$ alkyl or $C_1$-$C_5$ alkanoyl-$C_1$-$C_6$ alkyl.

$R^{13}$ is: $C_1$-$C_3$ perfluoroalkyl, $C_1$-$C_6$ alkyl, substituted $C_1$-$C_6$ alkyl, where the substituents are hydroxy, $NR^{10}R^{11}$, carboxy, phenyl or substituted phenyl; phenyl or substituted phenyl where the substituents on the phenyl are from 1 to 3 of halogen, $C_1$-$C_6$ alkyl, $C_1$-$C_6$ alkoxy or hydroxy;

where v is as defined above;

$R^4$, $R^{4b}$, $R^5$ and $R^{5a}$ are independently hydrogen, phenyl, substituted phenyl, $C_1$-$C_{10}$ alkyl, substituted $C_1$-$C_{10}$ alkyl, where the substituents on the alkyl or phenyl are from 1 to 5 of hydroxy, $C_1$-$C_6$ alkoxy, $C_3$-$C_7$ cycloalkyl, fluoro, $R^1$ substituted or $R^1$, $R^2$ independently disubstituted phenyl $C_1$-$C_3$ alkoxy, $R^1$ substituted or $R^1$, $R^2$ independently disubstituted phenyl, $C_1$-$C_{20}$-alkanoyloxy, $C_1$-$C_5$ alkoxycarbonyl, carboxy or formyl;

$R^4$ and $R^5$ can be taken together to form —$(CH_2)_rB(CH_2)_s$— where B is $CHR^1$, O, $S(O)_m$ or N—$R^{10}$, r and s are independently 1 to 3 and $R^1$ and $R^{10}$ are as defined above;

$R^6$ is hydrogen, $C_1$-$C_{10}$ alkyl or phenyl $C_1$-$C_{10}$ alkyl;

A is

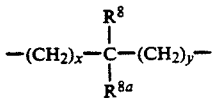

where x and y are independently 0-2;

$R^8$ and $R^{8a}$ are independently hydrogen, $C_1$-$C_{10}$ alkyl, substituted $C_1$-$C_{10}$ alkyl where the substituents are from 1 to 3 of imidazolyl, indolyl, hydroxy, fluoro, $S(O)_mR^{7a}$, $C_1$-$C_6$ alkoxy, $R^1$ substituted or $R^1$, $R^2$ independently disubstituted phenyl, $C_1$-$C_5$-alkanoyloxy, $C_1$-$C_5$ alkoxycarbonyl, carboxy, formyl, —$NR^{10}R^{11}$ where $R^{10}$ and $R^{11}$ are independently hydrogen, $C_1$-$C_6$ alkyl, or $C_1$-$C_5$ alkanoyl-$C_1$-$C_6$ alkyl; or $R^8$ and $R^{8a}$ can be taken together to form —$(CH_2)_t$— where t is 2 to 4; and $R^8$ and $R^{8a}$ can independently be joined to one or both of $R^4$ and $R^5$ to form alkylene bridges between the terminal nitrogen and the alkyl portion of the A group wherein the bridge contains from 1 to 5 carbon atoms; and pharmaceutically acceptable salts thereof.

Additional preferred compounds are realized in the above structural formula when:
n is 0 or 1;
p is 0 to 2;
q is 0 to 2;
w is 0 or 1;
X is $S(O)_m$ or —CH=CH—;
m is 0 or 1;

$R^1$, $R^2$, $R^{1a}$, $R^{2a}$, $R^{1b}$, and $R^{2b}$ are independently hydrogen, halogen, $C_1$-$C_7$ alkyl, $C_1$-$C_3$ perfluoroalkyl, —$S(O)_mR^{7a}$, $R^{7b}O(CH_2)_v$—, $R^{7b}COO(CH_2)_v$—, $R^{7b}OCO(CH_2)_v$—, phenyl or substituted phenyl where the substituents are from 1 to 3 of halogen, $C_1$-$C_6$ alkyl, $C_1$-$C_6$ alkoxy, or hydroxy;

$R^{7a}$ and $R^{7b}$ are independently hydrogen, $C_1$-$C_6$ alkyl, substituted $C_1$-$C_6$ alkyl, where the substituents are phenyl and v is 0 to 2;

$R^{3a}$ and $R^{3b}$ are independently hydrogen, $R^9$, $C_1$-$C_6$ alkyl substituted with $R^9$, phenyl substituted with $R^9$, or phenoxy substituted with $R^9$ with the proviso that either $R^{3a}$ or $R^{3b}$ must be a substituent other than hydrogen;

$R^9$ is: $R^{4b}R^{12a}NCON(R^{12b})(CH_2)_v$—, $R^{4b}R^{12a}NCSN(R^{12b})(CH_2)_v$—, $R^{4b}R^{12a}NN(R^{12b})CON(R^{12c})(CH_2)_v$—, $R^{4b}R^{12a}NN(R^{12b})COO(CH_2)_v$—, $R^{4b}R^{12a}NCOO(CH_2)_v$— or $R^{13}OCON(R^{12b})(CH_2)_v$—, where v is 0 to 2.

$R^{12a}$, $R^{12b}$ and $R^{12c}$ are independently $R^{5a}$ or $OR^{5a}$. $R^{12a}$ and $R^{12b}$, or $R^{12b}$ and $R^{12c}$, or $R^{13}$ and $R^{12b}$ or $R^{12a}$ and $R^{4b}$ can be taken together to form —$(CH_2)_r$—B—$(CH_2)_s$— where B is $CHR^1$, O, $S(O)_m$ or $NR^{10}$, m is 0, 1 or 2, r and s are independently 0 to 2, $R^1$ is as defined above and $R^{10}$ is hydrogen, $C_1$-$C_6$ alkyl or $C_1$-$C_5$ alkanoyl-$C_1$-$C_6$ alkyl;

$R^{13}$ is: $C_1$-$C_6$ alkyl, substituted $C_1$-$C_6$ alkyl, where the substituents are phenyl or substituted phenyl; phenyl or substituted phenyl where the substituents on the phenyl are from 1 to 3 of halogen, $C_1$-$C_6$ alkyl, $C_1$-$C_6$ alkoxy or hydroxy;

$R^4$, $R^{4b}$, $R^5$ and $R^{5a}$ are independently hydrogen, $C_1$-$C_{10}$ alkyl, substituted $C_1$-$C_{10}$ alkyl, where the substituents on the alkyl are from 1 to 5 of hydroxy, $C_1$-$C_6$ alkoxy, fluoro, $R^1$ substituted or $R^1$, $R^2$ independently disubstituted phenyl, $C_1$-$C_{20}$-alkanoyloxy, $C_1$-$C_5$ alkoxycarbonyl or carboxy;

$R^6$ is hydrogen or $C_1$-$C_{10}$ alkyl;

A is

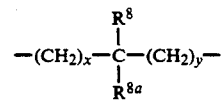

where x and y are independently 0-2;

$R^8$ and $R^{8a}$ are independently hydrogen, $C_1$-$C_{10}$ alkyl, substituted $C_1$-$C_{10}$ alkyl where the substituents are from 1 to 3 of imidazolyl, indolyl, hydroxy, fluoro, $S(O)_mR^{7a}$, $C_1$-$C_6$ alkoxy, $R^1$ substituted or $R^1$, $R^2$ independently disubstituted phenyl, $C_1$-$C_5$-alkanoyloxy, $C_1$-$C_5$ alkoxycarbonyl, carboxy; or $R^8$ and $R^{8a}$ can be taken together to form —$(CH_2)_t$— where t is 2; or $R^8$ and $R^{8a}$ can independently be joined to one or both of $R^4$ and $R^5$ to form alkylene bridges between the terminal nitrogen and the alkyl portion of the A group wherein the bridge contains from 1 to 5 carbon atoms; and pharmaceutically acceptable salts thereof.

Still further preferred compounds of the instant invention are realized in the above structural formula when;
n is 0 or 1;
p is 0 to 2;
q is 1;
w is 1;
X is $S(O)_m$ or —CH=CH—;
m is 0 or 1;

$R^1$, $R^2$, $R^{1a}$, $R^{2a}$, $R^{1b}$, and $R^{2b}$ are independently hydrogen, halogen, $C_1$-$C_7$ alkyl, $C_1$-$C_3$ perfluoroalkyl, —$S(O)_mR^{7a}$, $R^{7b}O(CH_2)_v$—, $R^{7b}COO(CH_2)_v$—, phenyl or substituted phenyl where the substituents are from 1 to 3 halogen, $C_1$-$C_6$ alkyl, $C_1$-$C_6$ alkoxy, or hydroxy;

$R^{7a}$ and $R^{7b}$ are independently hydrogen, $C_1$-$C_6$ alkyl, substituted $C_1$-$C_6$ alkyl, where the substituents are phenyl and v is 0 or 1;

$R^{3a}$ and $R^{3b}$ are independently hydrogen, $R^9$, or $C_1$-$C_6$ alkyl substituted with $R^9$ with the proviso that either $R^{3a}$ or $R^{3b}$ must be a substituent other than hydrogen;

$R^9$ is: $R^{4b}R^{12a}NCON(R^{12b})(CH_2)_v$—, $R^{4b}R^{12a}NN(R^{12b})CON(R^{12c})(CH_2)_v$—, $R^{4b}R^{12a}NN(R^{12b})COO(CH_2)_v$—, $R^{4b}R^{12a}NCOO(CH_2)_v$— or $R^{13}OCON(R^{12b})(CH_2)_v$—, where v is 0 to 1.

$R^{12a}$, $R^{12b}$ and $R^{12c}$ are independently $R^{5a}$. $R^{12a}$ and $R^{12b}$, or $R^{12b}$ and $R^{12c}$, or $R^{13}$ and $R^{12b}$ or $R^{12a}$ and $R^{4b}$ can be taken together to form —$(CH_2)_r$—B—$(CH_2)_s$— where B is $CHR^1$, O, $S(O)_m$ or $NR^{10}$, m is 0, 1 or 2, r and s are independently 0 to 2, $R^1$ is as defined above and $R^{10}$ is hydrogen, $C_1$-$C_6$ alkyl or $C_1$-$C_5$ alkanoyl $C_1$-$C_6$ alkyl;

$R^{13}$ is: $C_1-C_6$ alkyl, substituted $C_1-C_6$ alkyl, where the substituents are phenyl or substituted phenyl; phenyl or substituted phenyl where the substituents on the phenyl are from 1 to 3 of halogen, $C_1-C_6$ alkyl, $C_1-C_6$ alkoxy or hydroxy;

$R^4$, $R^{4b}$, $R^5$ and $R^{5a}$ are independently hydrogen, $C_1-C_{10}$ alkyl, substituted $C_1-C_{10}$ alkyl, where the substituents on the alkyl are from 1 to 3 of hydroxy, $C_1-C_3$ alkoxy, fluoro, $R^1$ substituted or $R^1$, $R^2$ independently disubstituted phenyl, $C_1-C_{20}$ alkanoyloxy, $C_1-C_5$ alkoxycarbonyl or carboxy;

$R^6$ is hydrogen;

A is

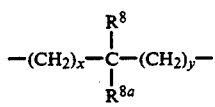

where x and y are independently 0-1;

$R^8$ and $R^{8a}$ are independently hydrogen, $C_1-C_{10}$ alkyl, substituted $C_1-C_{10}$ alkyl where the substituents are from 1 to 3 of imidazolyl, indolyl, hydroxy, fluoro, $S(O)_m R^{7a}$, $C_1-C_6$ alkoxy, $R^1$ substituted or $R^1$, $R^2$ independently disubstituted phenyl, $C_1-C_5$-alkanoyloxy, $C_1-C_5$ alkoxycarbonyl, carboxy; or $R^8$ and $R^{8a}$ can be taken together to form $-(CH_2)_t-$ where t is 2; and $R^8$ and $R^{8a}$ can independently be joined to one or both of $R^4$ and $R^5$ to form alkylene bridges between the terminal nitrogen and the alkyl portion of the A group wherein the bridge contains from 1 to 5 carbon atoms; and pharmaceutically acceptable salts thereof.

Representative preferred growth hormone releasing compounds of the present invention include the following:

1. N-[1-[[2'-[(Methoxycarbonyl)amino][1,1'-biphenyl]-4-yl]methyl]-2,3,4,5-tetrahydro-2-oxo-1H-1-benzazepin-3(R)-yl]-3-amino-3-methylbutanamide
2. N-[1-[[2'-[(Methylaminocarbonyl)amino][1,1'-biphenyl]-4-yl]methyl]-2,3,4,5-tetrahydro-2-oxo-1H-1-benzazepin-3(R)-yl]-3-amino-3-methylbutanamide
3. N-[1-[[2'-[(Ethylaminocarbonyl)amino][1,1'-biphenyl]-4-yl]methyl]-2,3,4,5-tetrahydro-2-oxo-1H-1-benzazepin-3(R)-yl]-3-amino-3-methylbutanamide
4. N-[1-[[2'-[(2-Propylaminocarbonyl)amino][1,1'-biphenyl]-4-yl]methyl]-2,3,4,5-tetrahydro-2-oxo-1H-1-benzazepin-3(R)-yl]-3-amino-3-methylbutanamide
5. N-[1-[[2'-[(Aminocarbonyl)amino][1,1'-biphenyl]-4-yl]methyl]-2,3,4,5-tetrahydro-2-oxo-1H-1-benzazepin-3(R)-yl]-3-amino-3-methylbutanamide
6. N-[1-[[2'-[(Morpholinocarbonyl)amino][1,1'-biphenyl]-4-yl]methyl]-2,3,4,5-tetrahydro-2-oxo-1H-1-benzazepin-3(R)-yl]-3-amino-3-methylbutanamide
7. N-[1-[[2'-[(Piperazinocarbonyl)amino][1,1'-biphenyl]-4-yl]methyl]-2,3,4,5-tetrahydro-2-oxo-1H-1-benzazepin-3(R)-yl]-3-amino-3-methylbutanamide
8. N-[1-[[2'-[[(Hydroxyethylamino)carbonyl]amino][1,1'-biphenyl]-4-yl]methyl]-2,3,4,5-tetrahydro-2-oxo-1H-1-benzazepin-3(R)-yl]-3-amino-3-methylbutanamide
9. N-[1-[[2'-[[(2-Hydroxypropylamino)carbonyl]amino][1,1'-biphenyl]-4-yl]methyl]-2,3,4,5-tetrahydro-2-oxo-1H-1-benzazepin-3(R)-yl]-3-amino-3-methylbutanamide
10. N-[1-[[2'-[(Methylaminocarbonyl)oxy][1,1'-biphenyl]-4-yl]methyl]-2,3,4,5-tetrahydro-2-oxo-1H-1-benzazepin-3(R)-yl]-3-amino-3-methylbutanamide
11. N-[1-[[2'-[(Dimethylaminocarbonyl)amino][1,1'-biphenyl]-4-yl]methyl]-2,3,4,5-tetrahydro-2-oxo-1H-1-1-benzazepin-3(R)-yl]-3-amino-3-methylbutanamide
12. N-[1-[[2'-[[(2(R)-Hydroxypropylamino)carbonyl]amino][1,1'-biphenyl]-4-yl]methyl]-2,3,4,5-tetrahydro-2-oxo-1H-1-benzazepin-3(R)-yl]-3-amino-3-methylbutanamide
13. N-[1-[[2'-[[(2(S)-Hydroxypropylamino)carbonyl]amino][1,1'-biphenyl]-4-yl]methyl]-2,3,4,5-tetrahydro-2-oxo-1H-1-benzazepin-3(R)-yl]-3-amino-3-methylbutanamide
14. N-[1-[[2'-[[(1-Hydroxyprop-2(R)-ylamino)carbonyl]amino][1,1'-biphenyl]-4-yl]methyl]-2,3,4,5-tetrahydro-2-oxo-1H-1-benzazepin-3(R)-yl]-3-amino-3-methylbutanamide
15. N-[1-[[2'-[4-[(Methylaminocarbonyl)amino]phenoxy]][1,1'-biphenyl]-4-yl]methyl]-2,3,4,5-tetrahydro-2-oxo-1H-1-benzazepin-3(R)-yl]-3-amino-3-methylbutanamide
16. N-[1-[[2'-[2-[(Methylaminocarbonyl)amino]phenoxy]][1,1'-biphenyl]-4-yl]methyl]-2,3,4,5-tetrahydro-2-oxo-1H-1-benzazepin-3(R)-yl]-3-amino-3-methylbutanamide
17. N-[1-[[2'-[(Aminocarbonyl)amino][1,1'-biphenyl]-4-yl]methyl]-2,3,4,5-tetrahydro-2-oxo-1H-1-benzazepin-3(R)-yl]-3-(2(R)-hydroxypropyl)amino-3-methylbutanamide
18. N-[1-[[2'-[(Aminocarbonyl)amino][1,1'-biphenyl]-4-yl]methyl]-2,3,4,5-tetrahydro-2-oxo-1H-1-benzazepin-3(R)-yl]-3-[2(S),3-dihydroxypropyl]amino-3-methylbutanamide
19. N-[1-[[2'-[(Methylaminocarbonyl)amino][1,1'-biphenyl]-4-yl]methyl]-2,3,4,5-tetrahydro-2-oxo-1H-1-benzazepin-3(R)-yl]-3-(2(R)-hydroxypropyl)amino-3-methylbutanamide
20. N-[1-[[2'-[(Methylaminocarbonyl)amino][1,1'-biphenyl]-4-yl]methyl]-2,3,4,5-tetrahydro-2-oxo-1H-1-benzazepin-3(R)-yl]-3-(2(S)-hydroxypropyl)amino-3-methylbutanamide
21. N-[1-[[2'-[(Methylaminocarbonyl)amino][1,1'-biphenyl]-4-yl]methyl]-2,3,4,5-tetrahydro-2-oxo-1H-1-benzazepin-3(R)-yl]-3-[2(S),3-dihydroxypropyl]amino-3-methylbutanamide
22. N-[1-[[2'-[(Morpholinocarbonyl)amino][1,1'-biphenyl]-4-yl]methyl]-2,3,4,5-tetrahydro-2-oxo-1H-1-benzazepin-3(R)-yl]-3-(2(R)-hydroxypropyl)amino-3-methylbutanamide
23. N-[1-[[2'-[(Morpholinocarbonyl)amino][1,1'-biphenyl]-4-yl]methyl]-2,3,4,5-tetrahydro-2-oxo-1H-1-benzazepin-3(R)-yl]-3-[2(S),3-dihydroxypropyl]amino-3-methylbutanamide
24. N-[1-[[2'-[[(2-Hydroxyethylamino)carbonyl]amino][1,1'-biphenyl]-4-yl]methyl]-2,3,4,5-tetrahydro-2-oxo-1H-1-benzazepin-3(R)-yl]-3-(2(R)-hydroxypropyl)amino-3-methylbutanamide
25. N-[1-[[2'-[[(2-Hydroxyethylamino)carbonyl]amino][1,1'-biphenyl]-4-yl]methyl]-2,3,4,5-tetrahydro-2-oxo-1H-1-benzazepin-3(R)-yl]-3-(2(S)-hydroxypropyl)amino-3-methylbutanamide
26. N-[1-[[2'-[[(2-Hydroxyethylamino)carbonyl]amino][1,1'-biphenyl]-4-yl]methyl]-2,3,4,5-tetrahydro-2-oxo-1H-1-benzazepin-3(R)-yl]-3-[2(S),3-dihydroxypropyl]amino-3-methylbutanamide
27. N-[1-[[2'-[(Methylaminocarbonyl)amino][1,1'-biphenyl]-4-yl]methyl]-2,3,4,5-tetrahydro-2-oxo-1H-1-benzazepin-3(R)-yl]-2-amino-2-methylpropanamide 28. N-[1-[[2'-[(Aminocarbonyl)amino][1,1'-biphenyl]-4-yl]methyl]-2,3,4,5-tetrahydro-2-oxo-1H-1-benzazepin-3(R)-yl]-2-amino-2-methylpropanamide
29. N-[1-[[2'-[(Morpholinocarbonyl)amino][1,1'-biphenyl]-4-yl]methyl]-2,3,4,5-tetrahydro-2-oxo-1H-1-benzazepin-3(R)-yl]-2-amino-2-methylpropanamide
30. N-[1-[[2'-[(Piperazinocarbonyl)amino][1,1'-biphenyl]-4-yl]methyl]-2,3,4,5-tetrahydro-2-oxo-1H-1-benzazepin-3(R)-yl]-2-amino-2-methylpropanamide
31. N-[1-[[2'-[[(2-Hydroxyethylamino)carbonyl]amino][1,1'-biphenyl]-4-yl]methyl]-2,3,4,5-tetrahydro-2-oxo-1H-1-benzazepin-3(R)-yl]-2-amino-2-methylpropanamide
32. N-[1-[[2'-[(Methylaminocarbonyl)oxy][1,1'-biphenyl]-4-yl]methyl]-2,3,4,5-tetrahydro-2-oxo-1H-1-benzazepin-3(R)-yl]-2-amino-2-methylpropanamide
33. N-[1-[[2'-[[(Methoxycarbonylmethylamino)carbonyl]amino][1,1'-biphenyl]-4-yl]methyl]-2,3,4,5-tetrahydro-2-oxo-1H-1-benzazepin-3(R)-yl]-2-amino-2-methylpropanamide
34. N-[1-[[2'-[(Hydroxyaminocarbonyl)amino][1,1'-biphenyl]-4-yl]methyl]-2,3,4,5-tetrahydro-2-oxo-1H-1-benzazepin-3(R)-yl]-2-amino-2-methylpropanamide
35. N-[1-[[2'-[(Methoxycarbonyl)amino][1,1'-biphenyl]-4-yl]methyl]-7-fluoro-2,3,4,5-tetrahydro-2-oxo-1H-1-benzazepin-3(R)-yl]-3-amino-3-methylbutanamide
36. N-[1-[[2'-[(Methylaminocarbonyl)amino][1,1'-biphenyl]-4-yl]methyl]-7-fluoro-2,3,4,5-tetrahydro-2-oxo-1H-1-benzazepin-3(R)-yl]-3-amino-3-methylbutanamide
37. N-[1-[[2'-[(Methylaminocarbonyl)amino][1,1'-biphenyl]-4-yl]methyl]-7-trifluoromethyl-2,3,4,5-tetrahydro-2-oxo-1H-1-benzazepin-3(R)-yl]-3-amino-3-methylbutanamide
38. N-[1-[[2'-[(Morpholinocarbonyl)amino][1,1'-biphenyl]-4-yl]methyl]-7-trifluoromethyl-2,3,4,5-tetrahydro-2-oxo-1H-1-benzazepin-3(R)-yl]-3-amino-3-methylbutanamide
39. N-[1-[[2'-[[(2-Hydroxyethylamino)carbonyl]amino][1,1'-biphenyl]-4-yl]methyl]-7-trifluoromethyl-2,3,4,5,-tetrahydro-2-oxo-1H-1-benzazepin-3(R)-yl]-3-amino-3-methylbutanamide
40. N-[1-[[2'-[[(2-Hydroxyethylamino)carbonyl]amino][1,1,'-biphenyl]-4-yl]methyl]-7-fluoro-2,3,4,5-tetrahydro-2-oxo-1H-1-benzazepin-3(R)-yl]-3-amino-3-methylbutanamide
41. N-[1-[[2'-[(Methylaminocarbonyl)oxy][1,1'-biphenyl]-4-yl]methyl]-7-fluoro-2,3,4,5-tetrahydro-2-oxo-1H-1-benzazepin-3(R)-yl]-3-amino-3-methylbutanamide
42. N-[1-[[2'-[2-[(Methylaminocarbonyl)amino]phenoxy][1,1'-biphenyl]-4-yl]methyl]-7-trifluoromethyl-2,3,4,5-tetrahydro-2-oxo-1H-1-benzazepin-3(R)-yl]-3-amino-3-methylbutanamide
43. N-[1-[[2'-[(Methylaminocarbonyl)amino][1,1'-biphenyl]-4-yl]methyl]-7-fluoro-2,3,4,5-tetrahydro-2-oxo-1H-1-benzazepin-3(R)-yl]-3-(2(R)-hydroxypropyl)amino-3-methylbutanamide
44. N-[1-[[2'-[(Methylaminocarbonyl)amino][1,1'-biphenyl]-4-yl]methyl]-7-fluoro-2,3,4,5-tetrahydro-2-oxo-1H-1-benzazepin-3(R)-yl]-3-[2(S),3-dihydroxypropyl]amino-3-methylbutanamide
45. N-[1-[[2'-[(Morpholinocarbonyl)amino][1,1'-biphenyl]-4-yl]methyl]-7-fluoro-2,3,4,5-tetrahydro-2-oxo-1H-1-benzazepin-3(R)-yl]-3-(2(R)-hydroxypropyl)amino-3-methylbutanamide
46. N-[1-[[2'-[(Morpholinocarbonyl)amino][1,1'-biphenyl]-4-yl]methyl-7-fluoro-2,3,4,5-tetrahydro-2-oxo-1H-1-benzazepin-3(R)-yl]-3-[2(S),3-dihydroxypropyl]amino-3-methylbutanamide
47. N-[1-[[2'-[[(2-Hydroxyethylamino)carbonyl]amino][1,1'-biphenyl]-4-yl]methyl]-7-fluoro-2,3,4,5-tetrahydro-2-oxo-1H-1-benzazepin-3(R)-yl]-3-(2(R)-hydroxypropyl)amino-3-methylbutanamide
48. N-[1-[[2'-[(Methylaminocarbonyl)amino][1,1'-biphenyl]-4-yl]methyl]-7-fluoro-2,3,4,5-tetrahydro-2-oxo-1H-1-benzazepin-3(R)-yl]-2-amino-2-methylpropanamide
49. N-[1-[[2'-[(Morpholinocarbonyl)amino][1,1'-biphenyl]-4-yl]methyl]-7-fluoro-2,3,4,5-tetrahydro-2-oxo-1H-1-benzazepin-3(R)-yl]-2-amino-2-methylpropanamide
50. N-[1-[[2'-[(Piperazinocarbonyl)amino][1,1'-biphenyl]-4-yl]methyl]-7-fluoro-2,3,4,5-tetrahydro-2-oxo-1H-1-benzazepin-3(R)-yl]-2-amino-2-methylpropanamide
51. N-[1-[[2'-[[(2-Hydroxyethylamino)carbonyl]amino][1,1'-biphenyl]-4-yl]methyl]-7-fluoro-2,3,4,5-tetrahydro-2-oxo-1H-1-benzazepin-3(R)-yl]-2-amino-2-methylpropanamide
52. N-[1-[[2'-[(Methylaminocarbonyl)oxy][1,1'-biphenyl]-4-yl]methyl]-7-fluoro-2,3,4,5-tetrahydro-2-oxo-1H-1-benzazepin-3(R)-yl]-2-amino-2-methylpropanamide
53. N-[5-[[2'-[(Methoxycarbonyl)amino][1,1'-biphenyl]-4-yl]methyl]-2,3,4,5-tetrahydro-4-oxo-1,5-benzothiazepin-3(S)-yl]-3-amino-3-methylbutanamide
54. N-[5-[[2'-[(Methylaminocarbonyl)amino][1,1'-biphenyl]-4-yl]methyl]-2,3,4,5-tetrahydro-4-oxo-1,5-benzothiazepin-3(S)-yl]-3-amino-3-methylbutanamide
55. N-[5-[[2'-[(Morpholinocarbonyl)amino][1,1'-biphenyl]-4-yl]methyl]-2,3,4,5-tetrahydro-4-oxo-1,5-benzothiazepin-3(S)-yl]-3-amino-3-methylbutanamide
56. N-[5-[[2'-[[(2-Hydroxyethylamino)carbonyl]amino][1,1'-biphenyl]-4-yl]methyl]-2,3,4,5-tetrahydro-4-oxo-1,5-benzothiazepin-3(S)-yl]-3-amino-3-methylbutanamide
57. N-[5-[[2'-[(Methylaminocarbonyl)amino][1,1'-biphenyl]-4-yl]methyl]-2,3,4,5-tetrahydro-4-oxo-1,5-benzothiazepin-3(S)-yl]-3-(2(R)-hydroxypropyl)amino-3-methylbutanamide
58. N-[5-[[2'-[(Morpholinocarbonyl)amino][1,1'-biphenyl]-4-yl]methyl]-2,3,4,5-tetrahydro-4-oxo-1,5-benzothiazepin-3(S)-yl]-3-(2(R)-hydroxypropyl)amino-3-methylbutanamide
59. N-[5-[[2'-[[(2-Hydroxyethylamino)carbonyl]amino][1,1'-biphenyl]-4-yl]methyl]-2,3,4,5-tetrahydro-4-oxo-1,5-benzothiazepin-3(S)-yl]-3-(2(R)-hydroxypropyl)amino-3-methylbutanamide
60. N-[5-[[2'-[(Methylaminocarbonyl)amino][1,1'-biphenyl]-4-yl]methyl]-2,3,4,5-tetrahydro-4-oxo-1,5-benzothiazepin-3(S)-yl]-3-[2(S),3-dihydroxypropyl]amino-3-methylbutanamide Representative examples of the nomenclature employed are given below:

N-[1-[[2'-[(Methylaminocarbonyl)amino][1,1'-biphenyl]-4-yl]methyl]-2,3,4,5-tetrahydro-2-oxo-1H-1-benzazepin-3(R)-yl]-3-amino-3-methylbutanamide

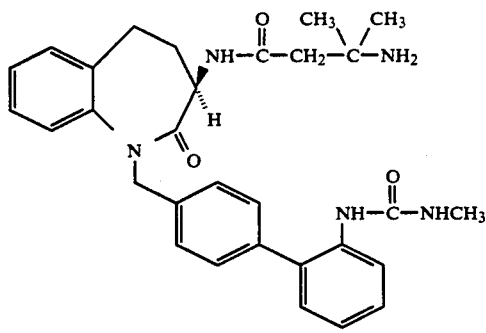

N-[1-[[2'-[(Methylaminocarbonyl)oxy][1,1'-biphenyl]-4-yl]methyl]-2,3,4,5-tetrahydro-2-oxo-1H-1-benzazepin-3(R)-yl]-3-amino-3-methylbutanamide

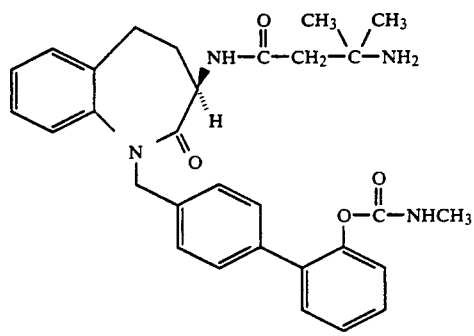

N-[1-[[2'-[(Methylaminocarbonyl)amino][1,1'-biphenyl]-4-yl]methyl]-2,3,4,5-tetrahydro-2-oxo-1H-1-benzazepin-3(R)-yl]-3(2(R)-hydroxypropyl)amino-3-methylbutanamide

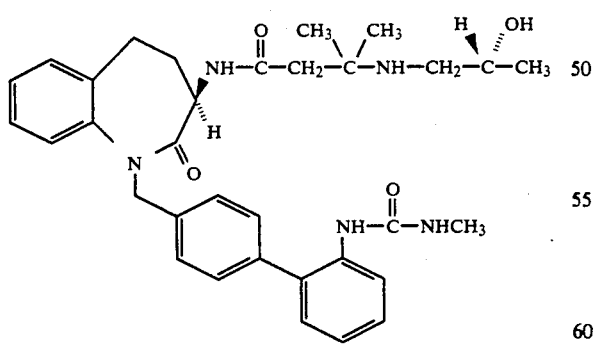

N-[5-[[2'-[(Methylaminocarbonyl)amino][1,1'-biphenyl]-4-yl]methyl]-2,3,4,5-tetrahydro-4-oxo-1,5-benzothiazepin-3(S)-yl]-3-amino-3-methylbutanamide

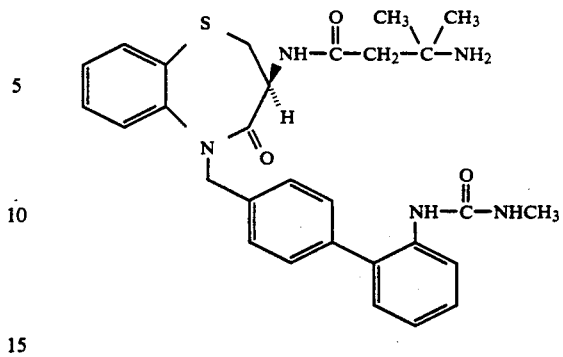

The compounds of the instant invention all have at least one asymmetric center as noted by the asterisk in the structural Formula I above. Additional asymmetric centers may be present on the molecule depending upon the nature of the various substituents on the molecule. Each such asymmetric center will produce two optical isomers and it is intended that all such optical isomers, as separated, pure or partially purified optical isomers or racemic mixtures thereof, be included within the ambit of the instant invention. In the case of the asymmetric center represented by the asterisk in Formula I, it has been found that the compound in which the 3-amino substituent is above the plane of the structure, as seen in Formula Ia, is more active and thus more preferred over the compound in which the 3-amino substituent is below the plane of the structure. In the substituent $(X)_n$, when n=0, the asymmetric center is designated as the R-isomer. When n=1, this center will be designated according to the R/S rules as either R or S depending upon the value of X.

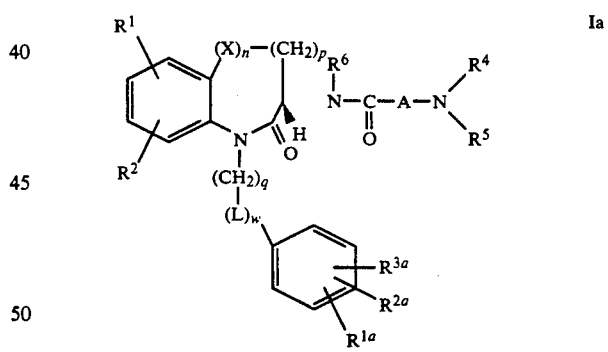

The instant compounds are generally isolated in the form of their pharmaceutically acceptable acid addition salts, such as the salts derived from using inorganic and organic acids. Examples of such acids are hydrochloric, nitric, sulfuric, phosphoric, formic, acetic, trifluoroacetic, propionic, maleic, succinic, malonic and the like. In addition, certain compounds containing an acidic function such as a carboxy can be isolated in the form of their inorganic salt in which the counterion can be selected from sodium, potassium, lithium, calcium, magnesium and the like, as well as from organic bases.

The compounds (I) of the present invention are prepared from aminolactam intermediates such as those of formula II. The preparation of these intermediates is described in the following reaction Schemes.

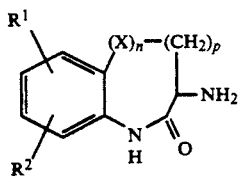

Benzo-fused lactams 3 wherein the lactam is a seven-membered ring are conveniently prepared from substituted tetralones 2 using known procedures. The substituted tetralones are, in some cases, commercially available or are prepared from a suitably substituted derivative of 4-phenylbutyric acid 1. Cyclization of 1 can be achieved by a number of methods well known in the literature including treatment with polyphosphoric acid at elevated temperatures as shown in Scheme 1.

Scheme 1

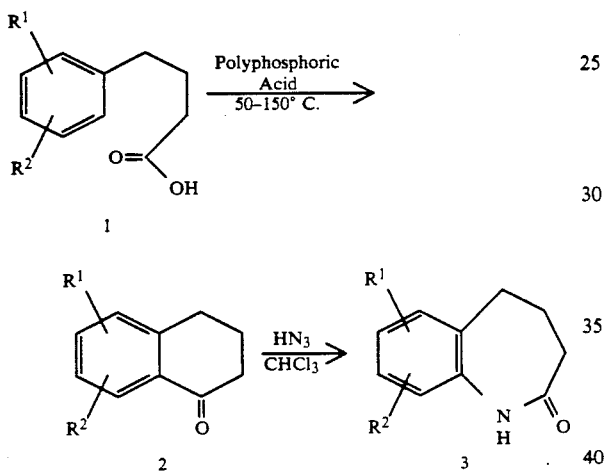

Conversion of substituted tetralones 2 to benzolactams 3 can be achieved by a number of methods familiar to those skilled in the art. A suitable method involves to use of hydrazoic acid (Schmidt reaction) to form the substituted benzolactam 3.

Benzo-fused lactams wherein the lactam is an eight-membered ring (6) are prepared as described by D. H. Jones, et al, J. Chem. Soc. C, 2176–2181 (1969) by an analogous series of transformations starting from a substituted derivative of 5-phenylpentanoic acid 4 as shown in Scheme 2.

Scheme 2

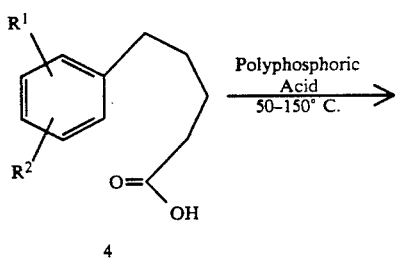

-continued
Scheme 2

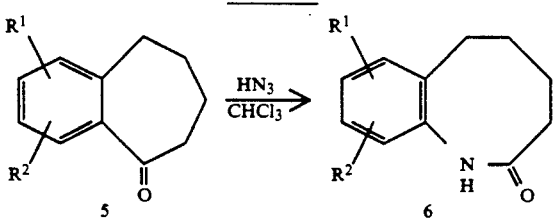

As shown in Scheme 3, 3-aminobenzolactam analogs wherein the lactam is a six-membered ring (11) are prepared from a substituted derivative of 2-nitrobenzyl chloride (or bromide) 7 by the method of A. L. Davis, et al, Arch. Biochem. Biophys, 102, 48–51 (1963) and references cited therein.

Scheme 3

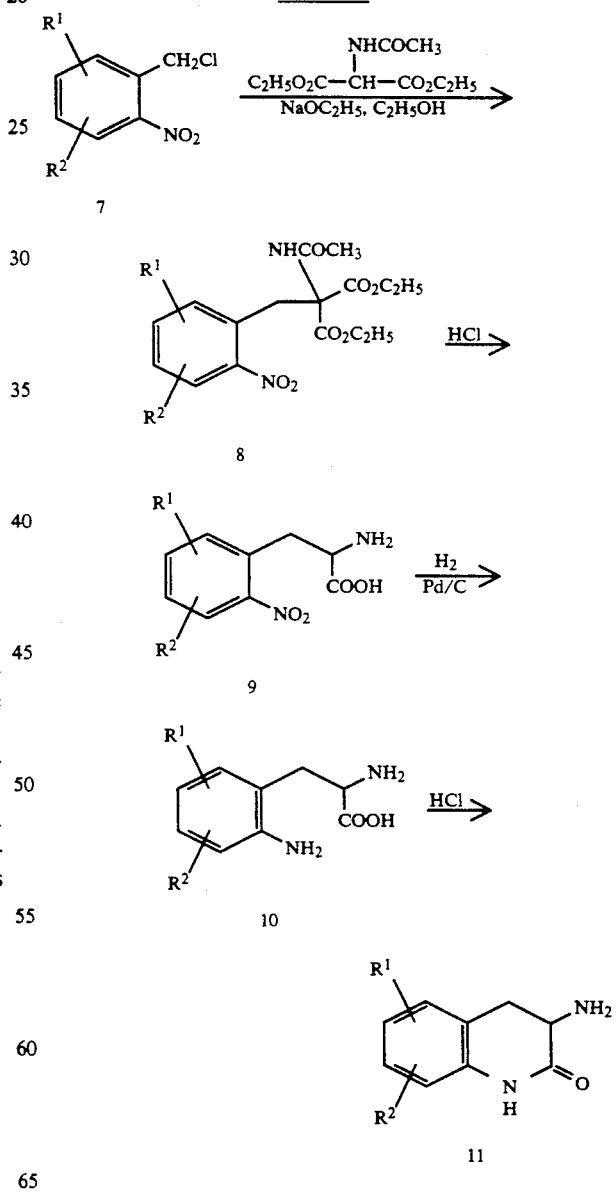

Conversion of substituted benzo-fused lactams to the requisite 3-amino derivatives can be achieved by a number of methods familiar to those skilled in the art, including those described by Watthey, et al, J. Med. Chem., 28, 1511-1516 (1985) and references cited therein. One common route proceeds via the intermediacy of a 3-halo (chloro, bromo or iodo) intermediate which is subsequently displaced by a nitrogen nucleophile, typically azide. A useful method of forming the 3-iodobenzolactam intermediates 12 involves treating the benzolactam with two equivalents each of iodotrimethylsilane and iodine at low temperature, as illustrated in Scheme 4 for the seven-membered ring analogs 3.

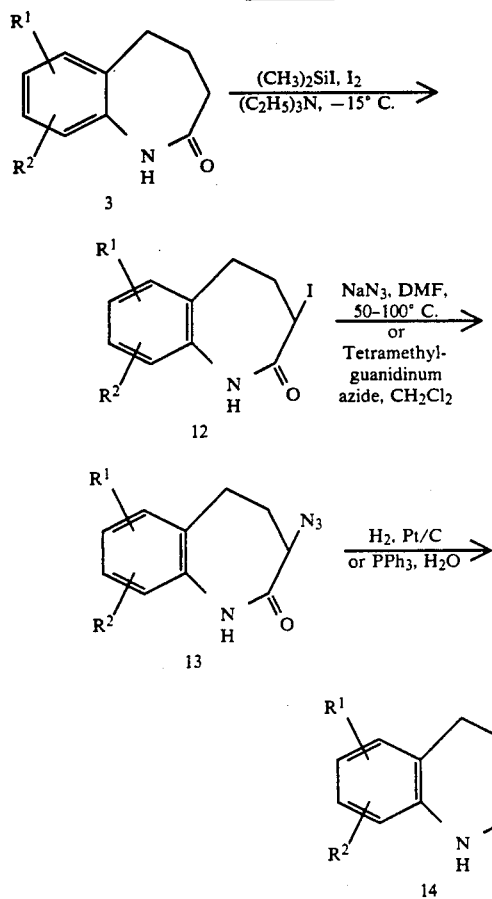

chemistry can be achieved in a number of ways including X-ray analysis of a suitable crystalline derivative.

A useful preparation of the chiral intermediate 19 is shown in Scheme 5.

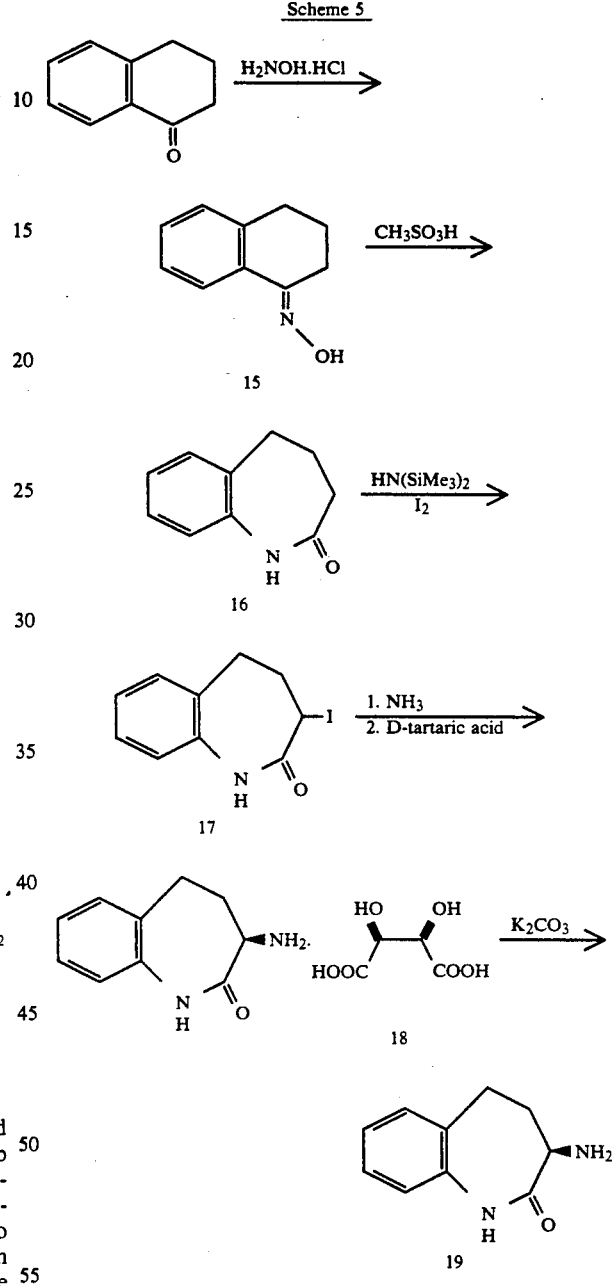

Elaboration of the iodo-benzolactams to the desired aminolactam intermediates II is achieved by a two-step procedure illustrated in Scheme 4. Typically, iodo-benzolactams 12 are treated with sodium azide in N,N-dimethylformamide at 50°-100° C. to give the 3-azido derivatives 13. Alternatively, tetramethylguanidinium azide in a solvent such as methylene chloride can be employed to achieve similar results. Hydrogenation with a metal catalyst, such as platinum on carbon, or alternatively, treatment with triphenylphosphine in wet toluene, results in formation of the amine derivative 14. Formation of the analogous derivatives of the eight-membered benzolactams is also achieved by the routes shown in Scheme 4.

Chiral aminobenzolactams are obtained by resolution of the racemates by classical methods familiar to those skilled in the art. For example, resolution can be achieved by formation of diastereomeric salts of the racemic amines with optically active acids such as D- and L-tartaric acid. Determination of absolute stereo- Conversion of 1-tetralone to the seven-membered benzolactam 16 is achieved by Beckman rearrangement of the intermediate oxime 15. Treatment of 16 with iodine and hexamethyldisilazane gives the 3-iodo drivative 17 which is sequentially treated with ammonia and D-tartaric acid to give the diastereomeric D-tartrate salt 18 after recrystallization. Liberation of the free amine 19 is achieved by neutralization of the D-tartrate salt with potassium carbonate followed by extractive isolation.

Intermediates of Formula II wherein X is a sulfur atom are prepared by methods described in the literature and known to those skilled in the art. As illustrated in Scheme 6, the seven-membered ring analog 27 is prepared from a protected derivative of cysteine 21 by the method of Slade, et al, J. Med. Chem., 28, 1517-1521 (1985) and references cited therein (CBz=benzyloxycarbonyl).

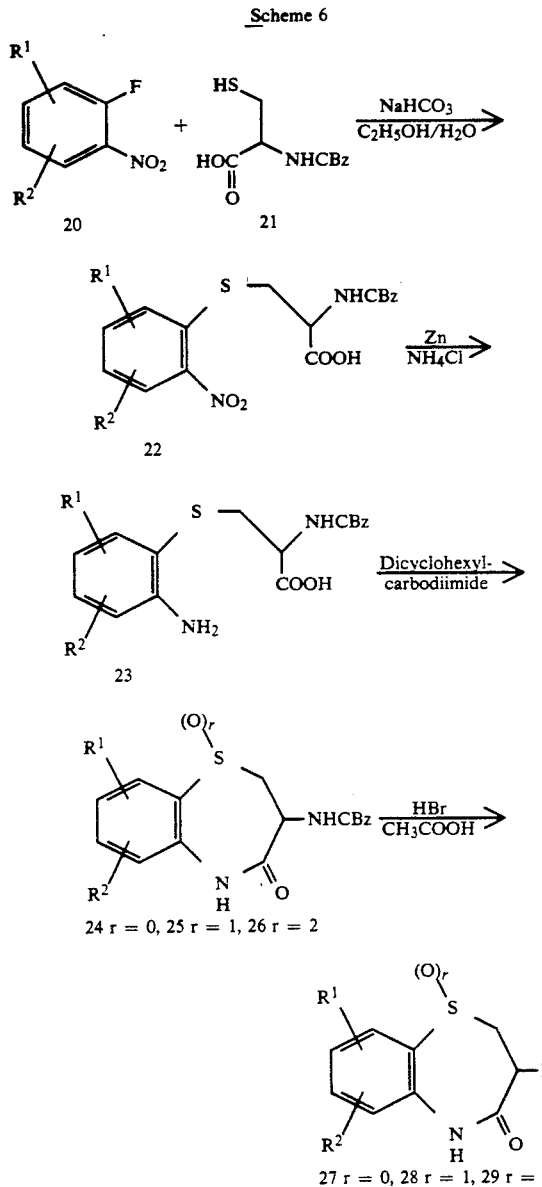

Sulfoxide and sulfone intermediates 28 and 29 are prepared by oxidation of 24 with various oxidants such as sodium periodate or meta-chloroperbenzoic acid. Eight-membered ring intermediates of Formula II wherein X is sulfur can be prepared by an analogous route starting from derivatives of homo-cysteine.

Intermediates of Formula II wherein X is an oxygen atom are prepared by methods described in the literature and known to those skilled in the art. For example, the seven-membered ring analog 26 can be prepared from a substituted derivative of 3-(2-nitrophenoxy)-propanoic acid 30 by the method of J. Ott, Arch. Pharm. (Weinheim, Ger.), 323(9), 601-603 (1990).

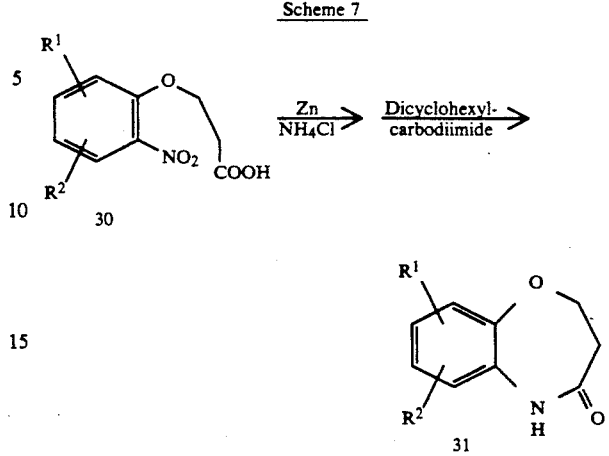

Six-membered ring analogs wherein X is oxygen (33) may be prepared by reaction of a substituted derivative of 2-aminophenol 32 with chloroacetyl chloride by the method of Huang and Chan, Synthesis, 10, 851 (1984) and references cited therein. Subsequent incorporation of an amino group at the 3 position of either 31 or 33 is achieved by the methods described in Scheme 4.

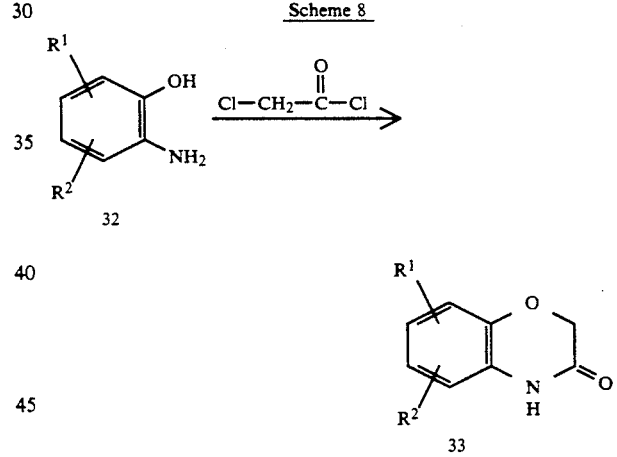

Seven-membered ring analogs of Formula II wherein X is C=O can be prepared from derivatives of tryptophan as described in the Australian Journal of Chemistry, 33, 633-640 (1980). Seven-membered ring analogs of Formula II wherein X is CH=CH can be prepared from the aforementioned analogs wherein X is C=O. Treatment of 34 with chemical reducing agents such as sodium borohydride in a polar solvent such as methanol or ethanol results in reduction to give the secondary alcohol derivative 35 (X=CHOH).

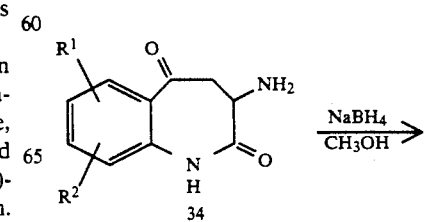

-continued

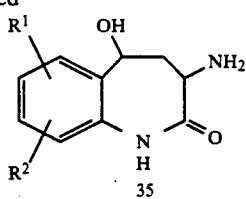

Dehydration of 35 can be achieved by several methods decribed in the literature and familiar to those skilled in the art. For example, treatment of 35 in an inert solvent, such as benzene, with a strong acid such as p-toluenesulfonic acid, will result in dehydration to the unsaturated analog 36.

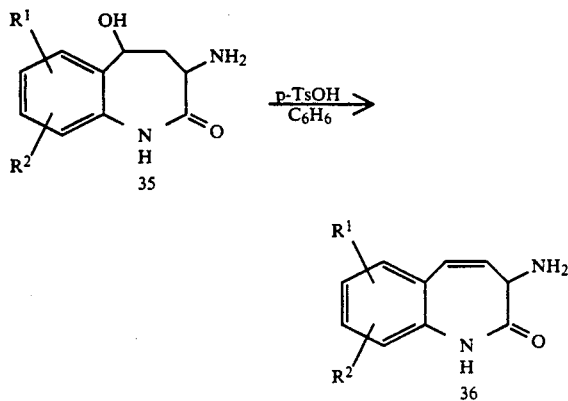

Intermediates of formula II can be further elaborated to new intermediates (formula III) which are substituted on the amino group (Scheme 9). Reductive alkylation of II with an aldehyde is carried out under conditions known in the art; for example, by catalytic hydrogenation with hydrogen in the presence of platinum, palladium or nickel catalysts or with chemical reducing agents such as sodium cyanoborohydride in an inert solvent such as methanol or ethanol.

Scheme 9

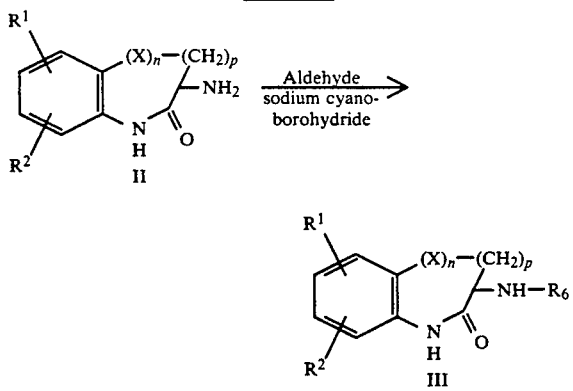

Attachment of the amino acid sidechain to intermediates of formula III is accomplished by the route shown in Scheme 10. Coupling is conveniently carried out by the use of an appropriately protected amino acid derivative, such as that illustrated by formula IV, and a coupling reagent such as benzotriazol-1-yloxytris(dimethylamino)phosphonium hexafluorophosphate ("BOP") in an inert solvent such as methylene chloride. Separation of unwanted side products, and purification of intermediates is achieved by chromatography on silica gel, employing flash chromatography (W. C. Still, M. Kahn and A. Mitra, J. Org. Chem., 43, 2923 (1978)) or by medium pressure liquid chromatography.

Scheme 10

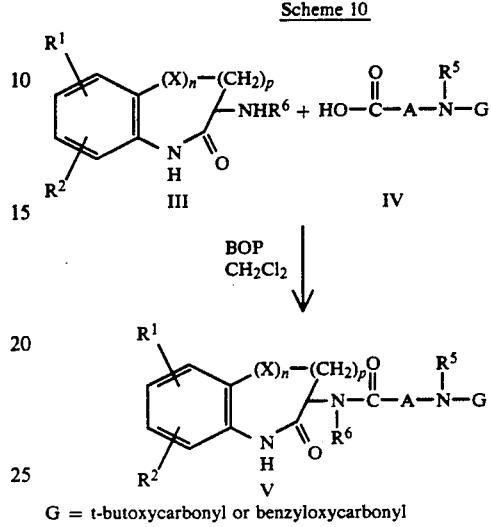

G = t-butoxycarbonyl or benzyloxycarbonyl

The protected amino acid derivatives IV are, in many cases, commercially available in t-butoxycarbonyl (BOC) or benzyloxycarbonyl (CBz) forms. A useful method to prepare the preferred sidechain 41 is shown in Scheme 11.

Scheme 11

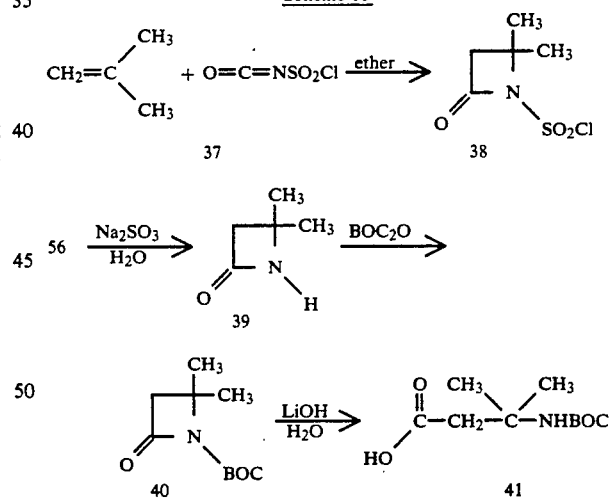

Reaction of isobutylene with N-chlorosulfonylisocyanate 37 in diethyl ether gives the azetidinone derivative 38. Removal of the chlorosulfonyl group with aqueous sodium sulfite followed by reaction with di-t-butyl-dicarbonate gives the BOC-protected intermediate 40. Alkaline hydrolysis gives the protected amino acid derivative 41 in good overall yield.

Intermediates of formula VII can be prepared as shown in Scheme 12 by treatment of the desired lactam intermediate V with an alkylating agent VI, wherein L is a good leaving group such as Cl, Br, I, O-methanesulfonyl or O-(p-toluenesulfonyl). Alkylation of intermediates of formula V is conveniently carried out in anhydrous dimethyl formamide (DMF) in the presence of bases such as sodium hydride or potassium t-butoxide for a period of 0.5 to 24 hours at temperatures of 20°-100° C. Substituents on the alkylating agent VI may need to be protected during alkylation. A description of such protecting groups may be found in: *Protective Groups in Organic Synthesis*, T. W. Greene, John Wiley and Sons, New York, 1981.

Alkylating agents VI are in some cases commercially available or may be prepared by methods described in the literature and familiar to one skilled in the art. Compounds of formula I where $R^{3a}$ or $R^{3b}$ is a carbamate, semicarbazide or urea derivative, wherein this functionality is attached to the phenyl ring by a nitrogen atom are prepared from intermediates 42, obtained by alkylation with a derivative of formula VI wherein $R^{3a}$ or $R^{3b}$ is a nitro group as shown in Scheme 13.

Scheme 12

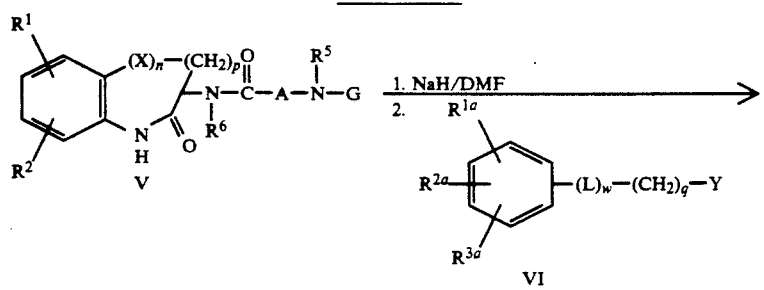

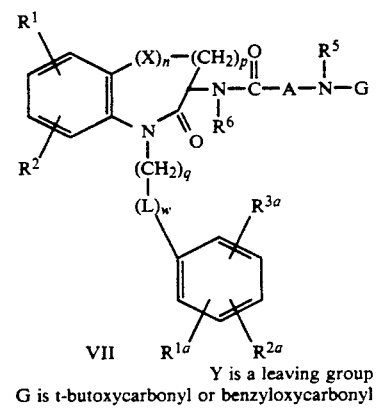

Y is a leaving group
G is t-butoxycarbonyl or benzyloxycarbonyl

Scheme 13

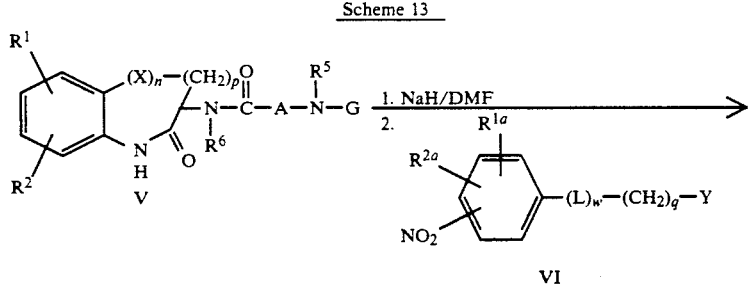

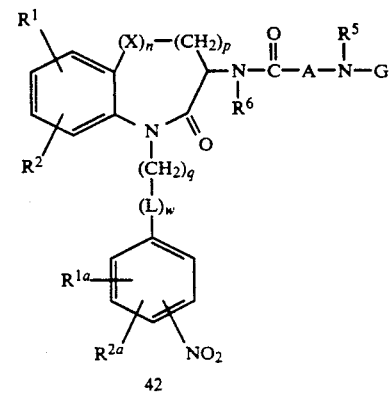

42

Y is a leaving group

Scheme 13 -continued

G is t-butoxycarbonyl or benzyloxycarbonyl

A useful method of synthesizing the preferred alkylating agent 46 is shown in reaction Scheme 14.

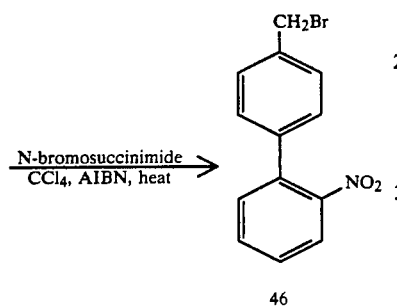

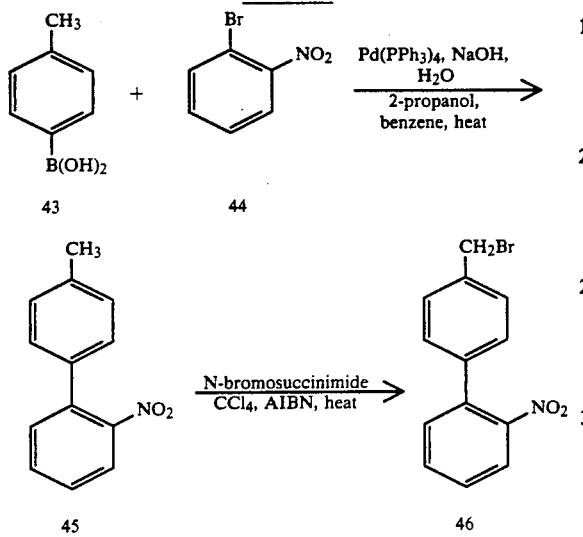

Reaction of 4-tolylboronic acid 43 with 2-bromonitrobenzene 44 in the presence of a transition metal catalyst such as (tetrakis)triphenylphosphine palladium (O) in a mixed solvent system containing aqueous sodium hydroxide, water, 2-propanol and benzene at elevated temperatures for several hours gives the coupled product 45 in good overall yield. Chromatographic purification and separation of unwanted by-products is conveniently performed on silica, eluting with common solvents such as hexane, ethyl acetate and methylene chloride. Conversion of 45 to the bromide derivative 46 is accomplished by treatment with N-bromosuccinimide in refluxing carbon tetrachloride in the presence of a radical initiator such as benzoyl peroxide or 2,2'-azobisisobutyronitrile (AIBN).

As shown in Scheme 15, reduction of the nitro group of 42 is achieved by hydrogenation in the presence of a metal catalyst, such as palladium on carbon, in a protic solvent such as methanol or ethanol. It may be appreciated by one skilled in the art that for certain compounds where catalytic hydrogenation is incompatible with existing functionality, alternative methods of reduction are indicated, such as chemical reduction with stannous chloride under acidic conditions. It should also be noted that the protecting group G in intermediate 42 must be compatible with the experimental conditions anticipated for reduction. For example, intermediates 42 wherein G is t-butoxycarbonyl (BOC) are stable to the conditions of catalytic reduction employed in the conversion to 47. Intermediates 47 may also be further elaborated to new intermediates 48 by reductive alkylation with an aldehyde by the aforementioned procedures.

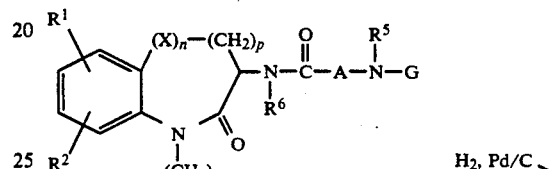

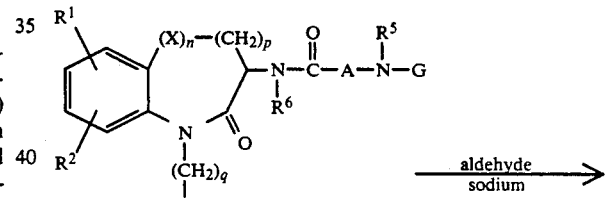

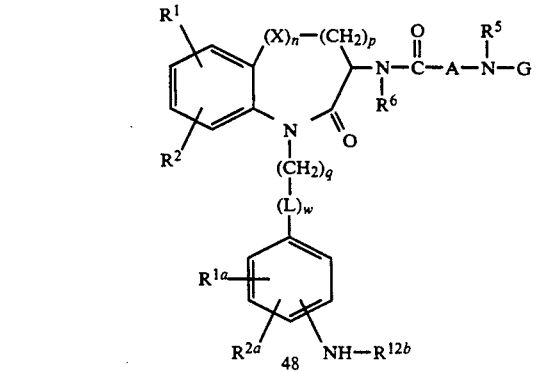

Elaboration of 47 to carbamate compounds 49 is achieved by reaction with the appropriate chloroformate reagent in pyridine or in methylene chloride with triethylamine as shown in Scheme 16.

Scheme 16

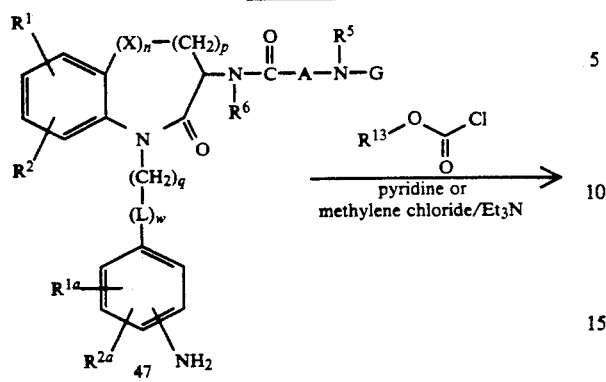

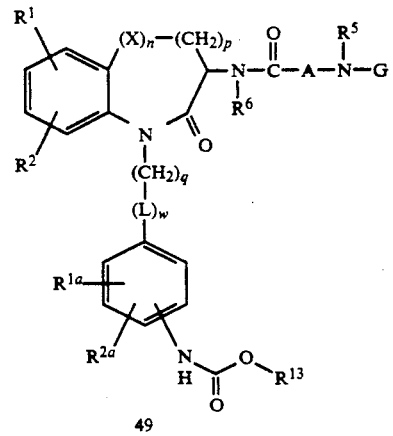

Transformation of amine intermediate 47 to urea derivatives is accomplished in several ways. Terminally disubstituted compounds can be obtained directly by reaction of 47 with a disubstituted carbamoyl chloride 50 in an inert solvent such as methylene chloride in the presence of triethylamine or 4-dimethylaminopyridine. In addition, mono-substituted compounds 53 wherein either $R^{4b}$ or $R^{12a}$ is hydrogen are obtained from 47 by reaction with an isocyanate 52 as shown in Scheme 17.

Scheme 17

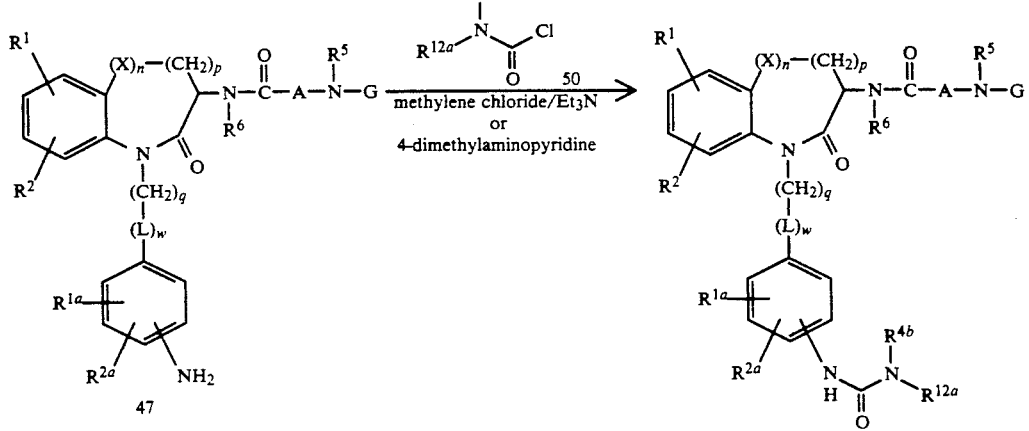

-continued
Scheme 17

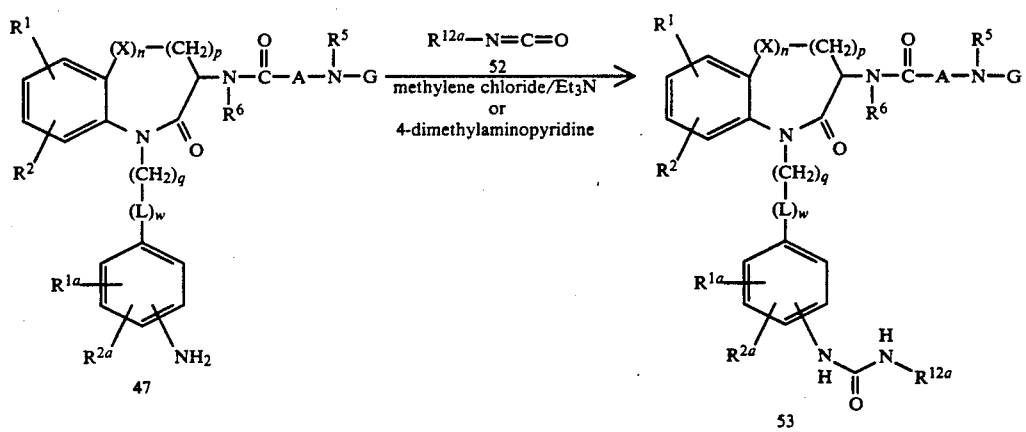

Alternatively, amine 47 is converted to an isocyanate 54 by treatment with phosgene or an equivalent reagent such as bis(trichloromethyl)carbonate (triphosgene) as indicated in Scheme 18. Subsequent reaction of 54 with primary or secondary amines in an inert solvent such as methylene chloride gives the corresponding urea derivates 51 in good yield. Isocyanate 54 is also converted to substituted semicarbazides 55 or hydroxy- or alkoxyureas 56 by reaction with substituted hydrazines or hydroxy- or alkoxylamines, respectively.

Scheme 18

-continued
Scheme 18

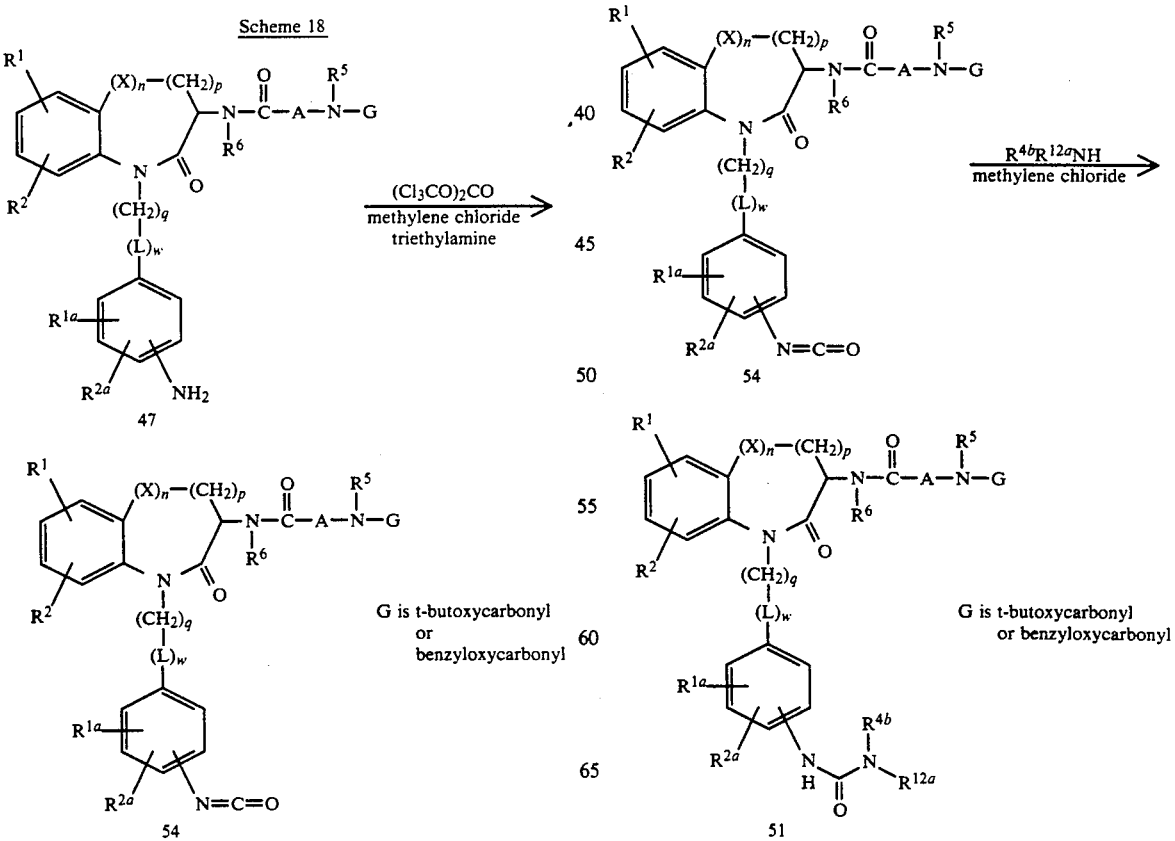

-continued

Scheme 18

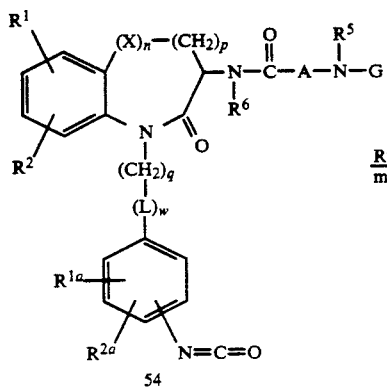

54

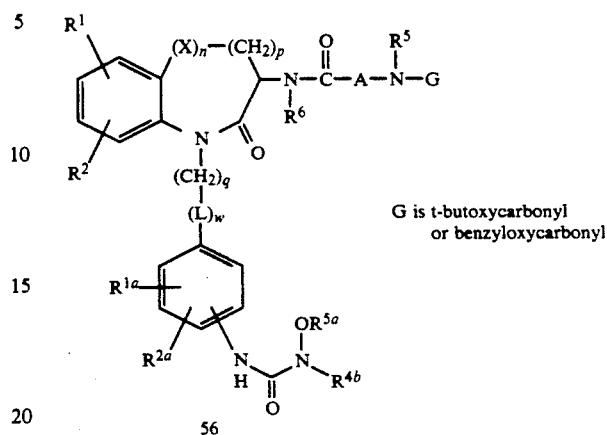

56

G is t-butoxycarbonyl or benzyloxycarbonyl

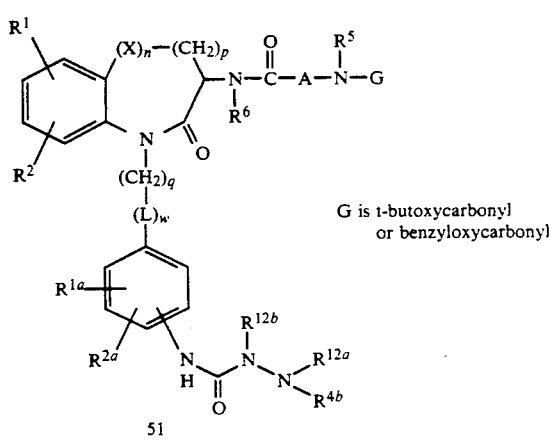

51

G is t-butoxycarbonyl or benzyloxycarbonyl

Compounds of formula I where $R^{3a}$ or $R^{3b}$ is a carbazate or carbamate derivative where attachment to the phenyl ring is through the oxygen atom of the carbazate or carbamate linkage are prepared from acetophenone intermediates 57 as indicated in Scheme 19.

Scheme 19

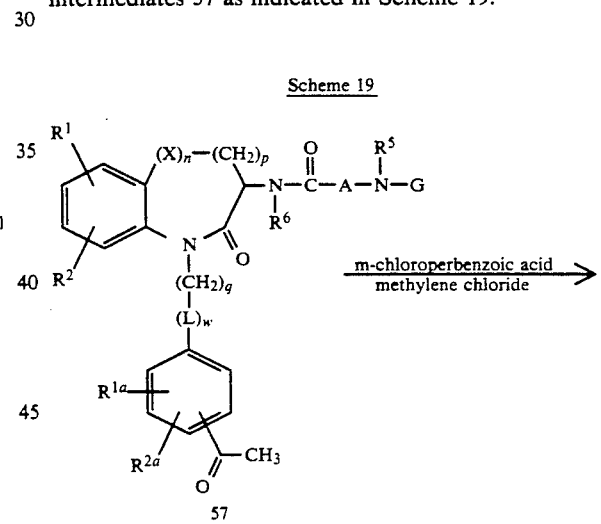

57

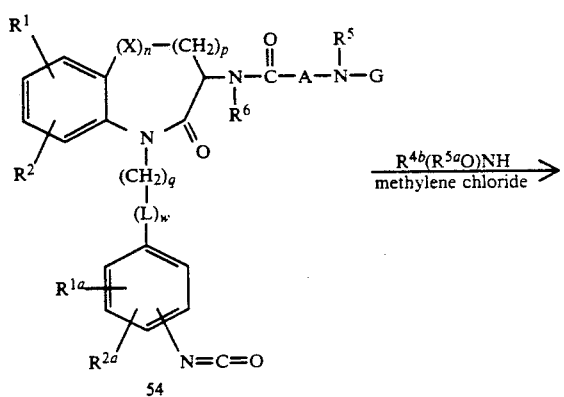

54

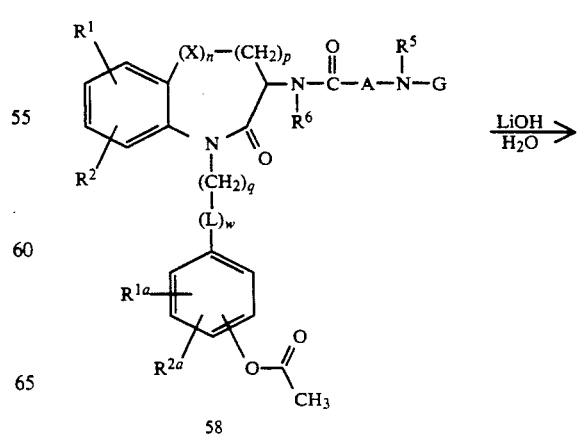

58

-continued

Scheme 19

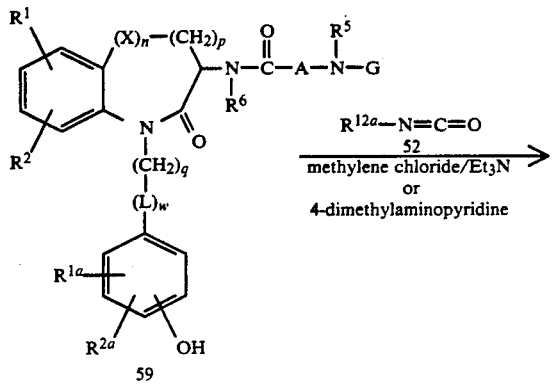

59

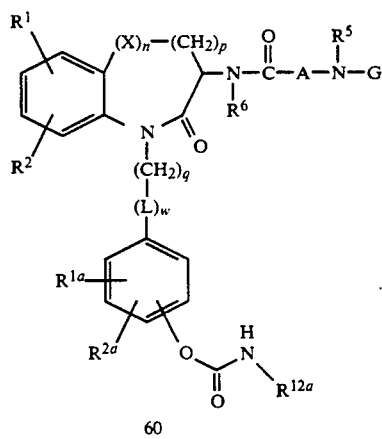

60

-continued
Scheme 19

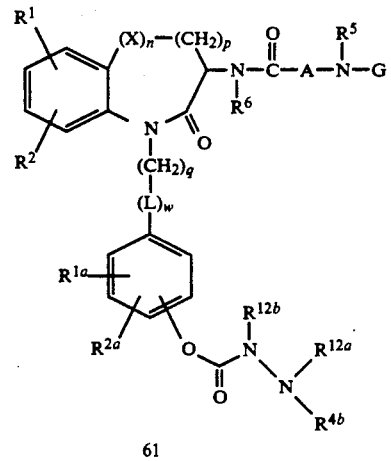

61

G is t-butoxycarbonyl or
benzyloxycarbonyl

Oxidative rearrangement of 57 through the use of a peroxy-carboxylic acid (Baeyer-Villager reaction) such as m-chloroperbenzoic acid gives the ester 58 which is hydrolyzed in the presence of a strong base such as sodium or lithium hydroxide to give phenol 59. Reaction of 59 with an isocyanate leads directly to carbamate analogs 60. Additionally, treatment of 59 with N,N'-carbonylidiimidazole in dimethylformamide can form an activated intermediate which will react with substituted hydrazine reagents to give carbazate products 61.

Conversion to the final products of formula I wherein $R^4$ is hydrogen, is carried out by simultaneous or sequential removal of all protecting groups from intermediate VII as illustrated in Scheme 20.

Scheme 20

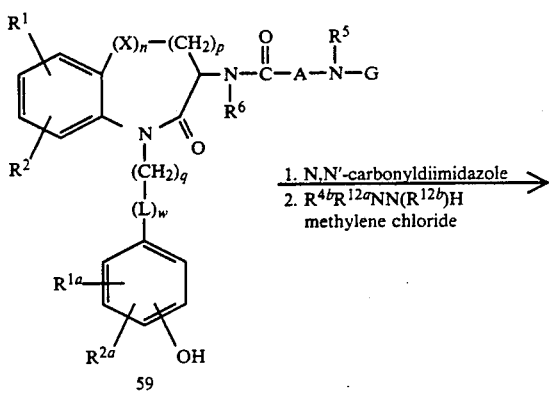

59

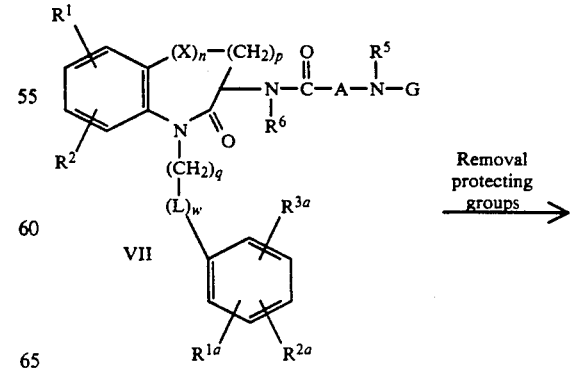

VII

Removal protecting groups

-continued
Scheme 20

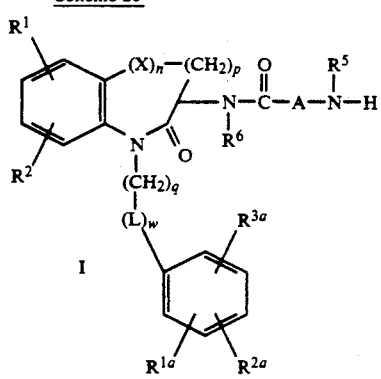

I

Removal of benzyloxycarbonyl groups can be achieved by a number of methods known in the art; for example, catalytic hydrogenation with hydrogen in the presence of platinum or palladium catalyst in a protic solvent such as methanol. In cases where catalytic hydrogenation is contraindicated by the presence of other potentially reactive functionality, removal of benzyloxycarbonyl groups can also be achieved by treatment with a solution of hydrogen bromide in acetic acid. Removal of t-butoxycarbonyl (BOC) protecting groups is carried out by treatment of a solution in a solvent such as methylene chloride or methanol, with a strong acid, such as hydrochloric acid or trifluoroacetic acid. Conditions required to remove other protecting groups which may be present can be found in *Protective Groups in Organic Synthesis* T. W. Greene, John Wiley and Sons, New York, 1981.

Compounds of formula I wherein $R^4$ and $R^5$ are each hydrogen can be further elaborated by reductive alkylation with an aldehyde by the aforementioned procedures or by alkylations such as by reaction with various epoxides. The products, obtained as hydrochloride or trifluoroacetate salts, are conveniently purified by reverse phase high performance liquid chromatography (HPLC) or by recrystallization.

It is noted that the order of carrying out the foregoing reaction schemes is not significant and it is within the skill of one skilled in the art to vary the order of reactions to facilitate the reaction or to avoid unwanted reaction products.

The growth hormone releasing compounds of Formula I are useful in vitro as unique tools for understanding how growth hormone secretion is regulated at the pituitary level. This includes use in the evaluation of many factors thought or known to influence growth hormone secretion such as age, sex, nutritional factors, glucose, amino acids, fatty acids, as well as fasting and non-fasting states. In addition, the compounds of this invention can be used in the evaluation of how other hormones modify growth hormone releasing activity. For example, it has already been established that somatostatin inhibits growth hormone release. Other hormones that are important and in need of study as to their effect on growth hormone release include the gonadal hormones, e.g., testosterone, estradiol, and progesterone; the adrenal hormones, e.g., cortisol and other corticoids, epinephrine and norepinephrine; the pancreatic and gastrointestinal hormones, e.g., insulin, glucagon, gastrin, secretin; the vasoactive intestinal peptides, e.g., bombesin; and the thyroid hormones, e.g., thyroxine and triiodothyronine. The compounds of Formula I can also be employed to investigate the possible negative or positive feedback effects of some of the pituitary hormones, e.g., growth hormone and endorphin peptides, on the pituitary to modify growth hormone release. Of particular scientific importance is the use of these compounds to elucidate the subcellular mechanisms mediating the release of growth hormone.

The compounds of Formula I can be administered to animals, including man, to release growth hormone in vivo. For example, the compounds can be administered to commercially important animals such as swine, cattle, sheep and the like to accelerate and increase their rate and extent of growth, and to increase milk production in such animals. In addition, these compounds can be administered to humans in vivo as a diagnostic tool to directly determine whether the pituitary is capable of releasing growth hormone. For example, the compounds of Formula I can be administered in vivo to children. Serum samples taken before and after such administration can be assayed for growth hormone. Comparison of the amounts of growth hormone in each of these samples would be a means for directly determining the ability of the patient's pituitary to release growth hormone.

Accordingly, the present invention includes within its scope pharmaceutical compositions comprising, as an active ingredient, at least one of the compounds of Formula I in association with a pharmaceutical carrier or diluent. Optionally, the active ingredient of the pharmaceutical compositions can comprise a growth promoting agent in addition to at least one of the compounds of Formula I or another composition which exhibits a different activity, e.g., an antibiotic or other pharmaceutically active material.

Growth promoting agents include, but are not limited to, TRH, diethylstilbesterol, theophylline, enkephalins, E series prostaglandins, compounds disclosed in U.S. Pat. No. 3,239,345, e.g., zeranol, and compounds disclosed in U.S. Pat. No. 4,036,979, e.g., sulbenox or peptides disclosed in U.S. Pat. No. 4,411,890.

A still further use of the disclosed novel benzo-fused lactam growth hormone secretagogues is in combination with other growth hormone secretagogues such as GHRP-6, GHRP-1 as described in U.S. Pat. Nos. 4,411,890; and publications WO 89/07110 and WO 89/07111 and B-HT920 or growth hormone releasing factor and its analogs or growth hormone and its analogs or somatomedins including IGF-1 and IGF-2.

As is well known to those skilled in the art, the known and potential uses of growth hormone are varied and multitudinous. Thus, the administration of the compounds of this invention for purposes of stimulating the release of endogenous growth hormone can have the same effects or uses as growth hormone itself. These varied uses of growth hormone may be summarized as follows: stimulating growth hormone release in elderly humans; Prevention of catabolic side effects of glucocorticoids, treatment of osteoporosis, stimulation of the immune system, treatment of retardation, acceleration of wound healing, accelerating bone fracture repair, treatment of growth retardation, treating renal failure or insufficiency resulting in growth retardation, treatment of physiological short stature, including growth hormone deficient children, treating short stature associated with chronic illness, treatment of obesity and growth retardation associated with obesity, treating growth retardation associated with Prader-Willi syndrome and Turner's syndrome; Accelerating the recovery and reducing hospitalization of burn patients; Treatment of intrauterine growth retardation, skeletal dysplasia, hypercortisolism and Cushings syndrome; Induction of pulsatile growth hormone release; Replacement of growth hormone in stressed patients; Treatment of osteochondrodysplasias, Noonans syndrome, schizophrenia, depression, Alzheimer's disease, delayed wound healing, and psychosocial deprivation; treatment of pulmonary dysfunction and ventilator dependency; Attenuation of protein catabolic response after a major operation; reducing cachexia and protein loss due to chronic illness such as cancer or AIDS. Treatment of hyperinsulinemia including nesidioblastosis; Adjuvant treatment for ovulation induction; To stimulate thymic development and prevent the age-related decline of thymic function; Treatment of immunosuppressed patients; Improvement in muscle strength, mobility, maintenance of skin thickness, metabolic homeostasis, renal hemeostasis in the frail elderly; Stimulation of osteoblasts, bone remodelling, and cartilage growth; Stimulation of the immune system in companion animals and treatment of disorders of aging in companion animals; Growth promotant in livestock; and stimulation of wool growth in sheep.

The compounds of this invention can be administered by oral, parenteral (e.g., intramuscular, intraperitoneal, intravenous or subcutaneous injection, or implant), nasal, vaginal, rectal, sublingual, or topical routes of administration and can be formulated in dosage forms appropriate for each route of administration.

Solid dosage forms for oral administration include capsules, tablets, pills, powders and granules. In such solid dosage forms, the active compound is admixed with at least one inert pharmaceutically acceptable carrier such as sucrose, lactose, or starch. Such dosage forms can also comprise, as is normal practice, additional substances other than inert diluents, e.g., lubricating agents such as magnesium stearate. In the case of capsules, tablets and pills, the dosage forms may also comprise buffering agents. Tablets and pills can additionally be prepared with enteric coatings.

Liquid dosage forms for oral administration include pharmaceutically acceptable emulsions, solutions, suspensions, syrups, the elixirs containing inert diluents commonly used in the art, such as water. Besides such inert diluents, compositions can also include adjuvants, such as wetting agents, emulsifying and suspending agents, and sweetening, flavoring, and perfuming agents.

Preparations according to this invention for parenteral administration include sterile aqueous or non-aqueous solutions, suspensions, or emulsions. Examples of non-aqueous solvents or vehicles are propylene glycol, polyethylene glycol, vegetable oils, such as olive oil and corn oil, gelatin, and injectable organic esters such as ethyl oleate. Such dosage forms may also contain adjuvants such as preserving, wetting, emulsifying, and dispersing agents. They may be sterilized by, for example, filtration through a bacteria-retaining filter, by incorporating sterilizing agents into the compositions, by irradiating the compositions, or by heating the compositions. They can also be manufactured in the form of sterile solid compositions which can be dissolved in sterile water, or some other sterile injectable medium immediately before use.

Compositions for rectal or vaginal administration are preferably suppositories which may contain, in addition to the active substance, excipients such as cocoa butter or a suppository wax.

Compositions for nasal or sublingual administration are also prepared with standard excipients well known in the art.

The dosage of active ingredient in the compositions of this invention may be varied; however, it is necessary that the amount of the active ingredient be such that a suitable dosage form is obtained. The selected dosage depends upon the desired therapeutic effect, on the route of administration, and on the duration of the treatment. Generally, dosage levels of between 0.0001 to 100 mg/kg. of body weight daily are administered to patients and animals, e.g., mammals, to obtain effective release of growth hormone.

The following examples are provided for the purpose of further illustration only and are not intended to be limitations of the disclosed invention.

EXAMPLE 1

N-[1-[[2'-[(Methoxycarbonyl)amino][1,1'-biphenyl]-4-yl]methyl]-2,3,4,5-tetrahydro-2-oxo-1H-1-benzazepin-3(R)-yl]-3-amino-3methylbutanamide, trifluoroacetate Step A: 1-Tetralone oxime To 4.6 L of water at room temperature in a 4-neck 50 L flask sitting in a steam bath apparatus equipped with an overhead stirrer, a temperature probe and reflux condenser was added 3.72 Kg (27.36 mol) of sodium acetate with stirring, followed by 1.9 Kg of hydroxylamine hydrochloride (27.36 mol). To this slurry at room temperature, 12 L of ethanol was added followed by 1.994 Kg (13.68 mol) of 1-tetralone. Additional ethanol (1.7 L) was used to rinse off the funnel and added to the reaction mixture. The resulting light orange slurry was heated to 75° C. over 40 minutes and maintained at 75°–85° C. for another 75 minutes. The reaction mixture was cooled with the aid of ice packed around the flask. When the internal temperature reached 32° C., the reaction mixture was pumped over 15 minutes into 60 L of ice contained in a 200 L vessel. The reaction vessel was washed with an additional 2 L of water which was added to the 200 L vessel. When the ice melted, the mixture was filtered through a filter pad and the wet cake washed with 4 L of water. The wet cake was suction dried for 1 hour then transferred to two trays and dried under vacuum at 40° C. for 2 days to give 2.094 Kg (13.01 mol, 95%) of product. $^1$H NMR (250 MHz, CDCl$_3$): 1.90 (m, 2H), 2.80 (t, 6 Hz, 2H), 2.88 (t, 6 Hz, 2H), 7.15–7.35 (m, 3H), 7.90 (d, 8 Hz, 1H), 8.9 (br s, 1H).

Step B: 2,3,4,5-Tetrahydro-1H-1-benzazepin-2-one

To 10 L of methanesulfonic acid in a 22 L 3-neck flask equipped with an overhead stirrer, a temperature probe, nitrogen inlet and reflux condenser, was added 2.6 Kg (18.61 mol) of phosphorus pentoxide. An additional 1.6 L of methanesulfonic acid was used to wash all the phosphorus pentoxide into the vessel. The mixture was heated at 90° C. for 2.5 hours then cooled to 50° C. using an ice bath and treated with 2.00 Kg (12.41 mol) of 1-tetralone oxime in several portions over 15 minutes. The mixture was heated at 63° C. for 10 minutes then slowly heated to 80° C. and kept at 80° C. for 3 hours. The reaction mixture was pumped into 70 L of ice then treated slowly with 11.25 L of 50% aqueous sodium hydroxide over 90 minutes at such a rate so as to maintain the temperature below 28° C. The mixture was filtered and 4 L of the filtrate was used to rinse the vessel. The wet cake (pink) was washed with 8 L of water then suction dried for 45 minutes and transferred to two trays and dried under vacuum at 40° C. for 2 days to give 1.9 Kg (11.79 mol, 95%) of product. $^1$H MNR (250 MHz,CDCl$_3$): 2.24 (m, 2H), 2.38 (t,6 Hz, 2H), 2.82 (t, 6 Hz, 2H), 7.03 (d, 8 Hz, 1H), 7,13 (m,1H), 7.24 (m, 2H), 8,63 (br s 1H).

Step C: 3-Iodo-2,3,4,5-tetrahydro-1H-benzazepin-2-one

A suspension of 1.8 Kg (11.17 mol) of 2,3,4,5-tetrahydro-1H-1-benzazepin-2-one in a mixture of 22.33 L of methylene chloride and 1.78 L (55.83 mol) of hexamethyldisilazane was heated at reflux for 10 minutes, then cooled to 30° C. and treated with 8.503 Kg (33.5 mmol) of iodine in one portion. The mixture was heated at reflux for 2.5 hours, then cooled to room temperature. Aqueous sodium sulfite containing 4.926 Kg of sodium sulfite in 44 L of water was cooled to 0° C. and into it was poured the reaction mixture in several portions with vigorous stirring while maintaining the temperature below 10° C. The reaction vessel was rinsed with 22.33 L of methylene chloride and the washing transferred to the quenching mixture. The quenching mixture was stirred vigorously and the layers allowed to separate. The aqueous layer was removed and reextracted with 22.33 L of methylene chloride. The combined organic layers were washed with 11 L of water and concentrated under vacuum to a final volume of approximately 5 L. The residue was treated with 55 L of toluene and concentrated under vacuum to a final volume of 10 L. The resulting slurry was isolated by filtration and the filter cake washed with an additional 5 L of toluene and dried under vacuum at ambient temperature for 24 hours to give 1.842 Kg (6.42 mol, 57%) of product. $^1$H NMR (200 MHz, CDCl$_3$): 2.6–2.8 (m, 3H), 2.93 (m, 1H), 4.64 (t, 8 Hz, 1H), 6.97 (d, 8 Hz, 1H), 7.10–7.35 (m, 3H), 7.55 (br s 1H).

Step D:
3(R)-Amino-2,3,4,5-tetrahydro-1H-1-benzazepin-2-one, D-tartaric acid salt 3-Iodo-2,3,4,5-tetrahydro-1H-1benzazepin-2-one (1.79 Kg, 6.24 mol) was slurried in 6.2 L of methanol and the slurry charged into an autoclave. Condensed ammonia (1.55 L) was added and the autoclave closed, with stirring, and heated to 100° C over 1 hour. Heating at 100° C. was continued for 2 hours then the autoclave was allowed to cool to room temperature over 1 hour, during which time the internal pressure was 150–155 psi. The reaction mixture was transferred to a polyethylene jug and the autoclave rinsed with 2×8 L of methanol. The washings were concentrated under vacuum at 30° C. then combined with the reaction mixture and concentrated to near dryness under vacuum at 30° C. The resulting residue was dissolved in 4 L of ethyl acetate then concentrated to dryness under vacuum at 30° C.

Sodium chloride (712 g) was dissolved in 2 L of water and 1.0 Kg of sodium carbonate was dissolved in 6 L of water. Two liters of the sodium carbonate solution was added to the concentrated residue and the resulting slurry transferred to an extracted flask. Another 2 L portion of the sodium carbonate solution was added to the residue flask and the solution transferred to the extraction flask. The remaining sodium carbonate solution was used in the same way. The sodium chloride solution was added to the sodium carbonate/aminolactam emulsion and the resulting mixture stirred for 10 minutes then extracted with four 6 L protions of methylene chloride. The combined methylene chloride layers were concentrated to dryness; the residue was treated with 2 L of 200 proof ethanol and the resulting slurry concentrated to dryness under vacuum to give 1.171 Kg of crude product.

The crude product was slurried in 8 L of ethanol and treated with 900 g of D-tartaric acid in one portion. Water (7 L) was added and the mixture heated to 77° C., then additional ethanol (45 L) was added and heating continued. The solution was cooled to 43° C. and treated with the seed slurry. (The seed slurry was prepared by the route described above starting with 10.50 g of crude product and 9.1 g of D-tartaric acid.) The solution was aged at room temperature for 48 hours. The slurry formed was removed by filtration and the wet cake washed with 1.8 L of ethanol. The resulting filter cake was suction dried with nitrogen bleeding for 20 hours, then transferred into a drying tray and dried under vacuum for 24 hours to give 354 g (1.085 mol, 17.4%) of the product. $^1$H NMR (250 MHz, CDCl$_3$): 2.13 (m, 1H), 2.51 (m, 2H), 2.73 (m, 2H), 3.68 (t, 6 Hz, 1H), 3.98 (s, 2H), 7.05 (d, 8 Hz, 1H), 7.16 (t, 8 Hz, 1H), 7.30 (m, 2H), 7.6 (br s, 5H), 10.26 (br s, 1H).

Step E:
3(R)-Amino-2,3,4,5-tetrahydro-1H-1-benzazepin-2-one

A solution of 229.23 g (0.700 mol) of 3(R)-amino-2,3,4,5-tetrahydro-1H-1-benzazepin-2-one, D-tartrate in 4.1 L of water was treated with 194 g (1.40 mol) of potassium carbonate. Subsequent portions of 100 g and 135 g of potassium carbonate were added until the pH was 10.5. The mixture was extracted with four 4 L portions of methylene chloride which were then combined and dried over magnesium sulfate. The aqueous layer was treated with 1.4 Kg of sodium chloride and reextracted with four 4 L portions of methylene chloride which were then combined and dried over magnesium sulfate. The two 16 L batches of extracts were combined, filtered and concentrated to dryness under vacuum to give 115.5 g of product which contained 1.6% of an impurity identified as 7-iodo-3(R)-amino-2,3,4,5-tetrahydro-1H-1-benzazepin-2-one.

A solution of 107.02 g (0.607 mol) of the intermediate obtained above in 1.712 L of ethanol was hydrogenated at room temperature and 40 psi over 4.00 g of 10% palladium on carbon for 4 hours. The catalyst was removed by filtration through solkaflok and the filtrate concentrated to dryness under vacuum to give 101.08 g (0.574 mol, 94.4%) of product.

Step F: 4,4-Dimethylazetidin-2-one

A 3-neck 3 L round bottom flask equipped with a magnetic stirrer, thermometer, cold finger condenser and nitrogen bubbler was charged with 1 L of ether. The flask was cooled to −65° C. and into it was condensed 500–600 mL of isobutylene. The cold finger condenser was replaced with a dropping funnel and 200 mL (325 g, 2.30 mol) of chlorosulfonyl isocyanate was added dropwise over 1.5 hours. The mixture was maintained at −65° C. for 1.5 hours then the dry ice/acetone cooling bath replaced with methanol/ice and the internal temperature slowly increased to −5° C. at which time the reaction initiated and the internal temperature rose to 15° C. with evolution of gas. The internal temperature remained at 15° C. for several minutes then dropped back down to −5° C. and the mixture stirred at −5° C. for 1 hour. The methanol/ice bath was removed and the reaction mixture warmed to room temperature and stirred overnight.

The reaction mixture was transferred to a 3-neck 12 L round bottom flask fitted with a mechanical stirrer and diluted with 2 L of ether. The well stirred reaction mixture was treated with 2 L of saturated aqueous sodium sulfite. After 1 hour, an additional 1 L of saturated aqueous sodium sulfite was added followed by sufficient sodium bicarbonate to adjust the pH to approximately 7. The mixture was stirred another 30 minutes then the layers allowed to separate. The ether layer was removed and the aqueous layer reextracted with 2×1 L of ether. The combined ether extracts were washed once with 500 mL of saturated aqueous sodium bicarbonate and once with 500 mL of saturated aqueous sodium chloride. The ether layer was removed, dried over magnesium sulfate, filtered and concentrated under vacuum to give 33 g of a pale yellow oil. The aqueous layer was made basic by the addition of solid sodium bicarbonate and extracted with 3×1 L of ether. The combined ether extracts were washed and dried as described above, then combined with the original 33 g of pale yellow oil and concentrated under vacuum to give 67.7 g of product. Further extraction of the aqueous layer with 4×1 L of methylene chloride and washing and drying as before gave an additional 74.1 g of product. Still further extraction of the aqueous layer with 4×1 L of methylene chloride gave an additional 21.9 g of product. The combined product (163.7 g, 1.65 mol, 72%) was used in Step G without purification. $^1$H NMR (200 MHz, CDCl$_3$): 1.45 (s, 6H), 2.75 (d, 3 Hz, 2H), 5.9 (br s, 1H).

Step G:
N-(t-Butoxycarbonyl)-4,4-dimethylazetidin-2-one

A 5 L, 3-neck round bottom flask equipped with a magnetic stirrer, thermometer, nitrogen bubbler and addition funnel was charged with 88.2 g (0.89 mol) of 4,4-dimethylazetidin-2-one (Step F), 800 mL of methylene chloride, 150 mL of triethylamine (1.08 mol) and 10.9 g (0.089 mol) of 4-dimethylaminopyridine. To the stirred solution, at room temperature was added dropwise over 15 minutes a solution of 235 g (1.077 mol) of di-t-butyl-dicarbonate in 300 mL of methylene chloride. The reaction mixture was stirred at room temperature overnight, then dikuted with 1 L of methylene chloride and washed with 500 mL of saturated aqueous ammonium chloride, 500 mL of water, and 500 mL of saturated aqueous sodium chloride. The organic layer was separated, dried over magnesium sulfate, filtered and concentrated under vacuum to afford 180.3 g of crude product as an orange solid. The material was used directly in Step H without purification. $^1$H NMR (200 MHz, CDCl$_3$): 1.50 (s, 9H), 1.54 (s, 6H), 2.77 (s, 2H).

Step H: 3-t-Butoxycarbonylamino-3-methylbutanoic acid

A 3 L, 3-neck round bottom flask equipped with a magnetic stirrer, thermometer, nitrogen bubbler and addition funnel was charged with 180.3 g (0.89 mol) of N-(t-butoxycarbonyl)-4,4-dimethylazetidin-2-one dissolved in 1 L of tetrahydrofuran. The solution was cooled to 0°-5° C. and treated dropwise with 890 mL of 1.0M aqueous lithium hydroxide over 30 minutes. The reaction mixture was stirred at 0°-5° C. for 2 hours, then diluted with 1 L of ether and 1 L of water. The layers were allowed to separate and the aqueous layer was reextracted with an additional 1 L of ether. The aqueous layer was acidified by the addition of 1 L of saturated aqueous sodium bisulfate, then extracted with 1×1 L and 2×500 mL of ether. The combined organic layer and ether extracts were washed with 500 mL of saturated aqueous sodium chloride, dried over magnesium sulfate and concentrated under vacuum to give 173 g of a yellow oil that solidified upon standing. The material was slurried with warm hexane, then filtered and dried under high vacuum to afford 168.5 g (0.775 mol, 87%) of product as a white solid. $^1$H NMR (200 MHz, CDCl$_3$): 1.39 (s, 6H), 1.44 (s, 9H), 2.72 (s, 2H). FAB-MS: calculated for C$_{10}$H$_{19}$NO$_4$ 217; found 218 (M+H, 54%).

Step I:
3-t-Butoxycarbonylamino-3-methyl-N-[2,3,4,5-tetrahydro-2-oxo-1H-1-benzazepin-3(R)-yl]butanamide A solution of 8.70 g (49.4 mmol) of 3(R)-amino-2,3,4,5-tetrahydro-1H-1-benzazepin-2-one (Step E) in 100 mL of methylene chloride was treated with 10.73 g (49.4 mmol) of 3-t-butoxycarbonylamino-3-methylbutanoic acid (Step H) and 13.8 mL of triethylamine (10.0 g, 99 mmol, 2 eq). The reaction flask was immersed in an ambient temperature water bath then 26 g of benzotriazol-1-yloxytris(dimethylamino)phosphonium hexafluorophosphate (59 mmol, 1.2 eq) was added all at once and the mixture stirred at room temperature for 2 hours. The reaction mixture was added to 300 mL of ethyl acetate and washed three times with 5% aqueous citric acid, twice with saturated aqueous sodium bicarbonate and once with saturated aqueous sodium chloride. The organic layer was removed, dried over magnesium sulfate, filtered and the filtrate concentrated under vacuum. The residue was purified by preparative high pressure liquid chromatography on silica, eluting with ethyl acetate/hexane (4:1), to afford 17.42 g (46.4 mmol, 94%) of the product as a white solid. $^1$H NMR (200 MHz, CDCl$_3$): 1.37 (s, 6H), 1.44 (s, 9H), 1.95 (m, 1H), 2.46 (d, 15 Hz, 1H), 2.59 (d, 15 Hz, 1H), 2.6–3.0, (m, 3H), 4.53 (m, 1H), 5.30 (br s, 1H), 6.72 (d, 7 Hz, 1H), 6.98 (d, 8 Hz, 1H), 7.1–7.3 (m, 3H), 7.82 (br s, 1H). FAB-MS: calculated for C$_{20}$H$_{29}$N$_3$O$_4$ 375; found 376 (M+H, 70%).

Step J: 4-Methyl-2'-nitro-1,1'-biphenyl

A vigorously stirred mixture of 4-tolylboronic acid (34 g, 0.25 mol) and 2-bromo-1-nitrobenzene (34 g, 0.168 mol) in a mixture of 5N sodium hydroxide (170 mL), water (57 mL), isopropanol (215 mL) and benzene (1080 mL) under a nitrogen atmosphere was treated with (tetrakis)triphenylphosphine palladium (0) (11.9 g). The stirred bilayer reaction mixture was heated at reflux for 3 hours. The cooled reaction mixture was filtered through Celite and the filter cake washed with fresh benzene. The organic layer was separated and washed with water (3×), dried over magnesium sulfate and filtered. The filtrate was evaporated under vacuum and the residue (46.1 g) purified by preparative high pressure liquid chromatography on silica gel, eluting with hexane/ethyl acetate (20:1) gave 28.05 g of the product. EI-MS: calculated for C$_{13}$H$_{11}$NO$_2$ 213; found 213 (M+). $^1$H NMR (400 MHz, CDCl$_3$): 2.38 (s, 3H), 7.20 (m, 4H), 7.43 (m, 2H), 7.59 (t, 1H), 7.8 (d, 1H).

Step K: 4-Bromomethyl-2'-nitro-1,1'-biphenyl

A solution of 4-methyl-2'-nitro-1,1'-biphenyl (Step J) (6.0 g, 28.2 mmol), N-bromosuccinimide (4.99 g, 28.2 mmol) and AIBN (653 mg) in 75 mL of carbon tetrachloride was heated at reflux until a negative potassium iodide test was obtained (1.5 h). The reaction mixture was cooled and filtered. The filtrate was evaporated under vacuum to yield 8.41 g of crude product. $^1$H NMR revealed the product composition was approximatly 75% monobromo and 10% dibromo, in addition to 15% of unreacted starting material. $^1$H NMR (200 MHz, CDCl$_3$): 4.53 (s, 2H), 7.2–7.7 (m, 7H), 7.85 (m, 1H). EI-MS: calculated for C$_{14}$H$_{10}$BrN 272; found 272,274 (M+).

Step L: 4-Hydroxymethyl-2'-nitro-1,1'-biphenyl

A solution of 4-bromomethyl-2'-nitro-1,1'-biphenyl (7.27 g, 24.8 mmol) in acetic acid (50 mL) was treated with potassium acetate (4.88 g, 49.1 mmol). The reaction mixture was heated at reflux for 2 hours. After cooling, the reaction mixture was filtered and the precipitate was washed with acetic acid (2×). The filtrate was evaporated under vacuum and the residue was triturated with ethyl ether. The ether layer was washed consecutively with water, saturated aqueous sodium bicarbonate (3×) and water. The organic layer was dried over magnesium sulfate, filtered and evaporated under vacuum. The residue was dissolved in methanol (50 mL) and treated with a 6N methanolic potassium hydroxide solution (5 mL). After stirring for 1 hour at room temperature, thin layer chromatography indicated the absence of starting material. The reaction mixture was acidified with acetic acid and evaporated under vacuum. The residue was washed free of acetic acid by washing an etheral solution with aqueous sodium bicarbonate and water. After drying over magnesium sulfate, the ethereal solution was evaporated under vacuum. The residue was purified by preparative high pressure liquid chromatography on silica gel, eluting with hexane/ethyl acetate (3:1) to give 2'-nitro-1,1'biphenyl-4-carboxaldehyde (620 mg) followed by 4-hydroxymethyl-2'-nitro-1,1'-biphenyl (3.06 g, 13.4 mmol, 54%).

Step M:
4-(Tetrahydropyranyloxy)methyl-2'-nitro-1,1'-biphenyl

A solution of 4-hydroxymethyl-2'-nitro-1,1'-biphenyl (3.06 g, 13.4 mmol) and 3,4-dihydropyran (1.8 mL, 20.1 mmol) in methylene chloride (50 mL) under a nitrogen atmosphere was treated with pyridinium p-toluenesulfonate (336 mg, 1.34 mmol). After stirring for 3 hours at room temperature, thin layer chromatography indicated that no starting material remained. The reaction mixture was diluted with ethyl ether (300 mL). The ether extracts were washed with saturated aqueous sodium chloride, dried over magnesium sulfate and filtered. The filtrate was evaporated under vacuum and the residue purified by preparative high pressure liquid chromatography on silica gel, eluting with hexane/ethyl acetate (10:1) to give 4.47 g of the product.

Step N:
4-(Tetrahydropyranyloxy)methyl-2'-amino-1,1'-biphenyl

A solution of 4-(tetrahydropyranyloxy)methyl-2'-nitro-1,1'-biphenyl (4.12 g, 13.2 mmol) in 100 mL of methanol was hydrogenated at 40 psi in the presence of 5% palladium on carbon. After 2 hours, uptake of hydrogen was complete. The reaction mixture was filtered through diatomacious earth, and the filter cake washed with methanol. The filtrate was evaporated under vacuum to yield 3.57 g of the product.

Step O:
4-Hydroxymethyl-2'-(methoxycarbonyl)amino-1,1'-biphenyl

A solution of (tetrahydropyranyloxy)methyl-2'-amino-1,1'-biphenyl (500 mg, 1.76 mmol) in pyridine (6 mL) was treated with methyl chloroformate (0.41 mL, 5.3 mmol). The reaction mixture was stirred at room temperature for 48 hours. The reaction mixture was evaporated under vacuum. The residue was taken up in ethyl ether and washed with water (3×). The ether layer was dried over magnesium sulfate, filtered and evaporated under vacuum to yield 547 mg of crude 4-(tetrahydropyranyloxy)methyl-2'-(methoxycarbonyl)amino-1,1'-biphenyl.

The crude 4-(tetrahydropyranyloxy)methyl-2'-(methoxycarbonyl)amino-1,1'-biphenyl (250 mg) dissolved in 4 mL of methanol was treated with 1 mL of 10% methanolic p-toluenesulfonic acid. The reaction mixture was stirred at room temperature for 1 hour. The reaction mixture was made basic by the addition of saturated aqueous sodium bicarbonate, then diluted with ethyl acetate. The organic layer was washed with water (2×), dried over magnesium sulfate and evaporated under vacuum. The residue was purified by preparative thin layer chromatography on silica gel, eluting with methylene chloride/methanol (100:3) to give 137 mg of the product. FAB-MS (Li+spike): calculated for C$_{15}$H$_{15}$NO$_3$ (257); found 264 (M+Li). $^1$H NMR (200 MHz, CDCl$_3$): 3.51 (s, 3H), 4.75 (s, 2H), 6.62 (br s, 1H), 7.14 (dd, 2H), 7.34 (dd, 1H), 7.4 (dd, 4H).

Step P:
4-Bromomethyl-2'-(methoxycarbonyl)amino-1,1'-biphenyl

A solution of 4-hydroxymethyl-2'-(methoxycarbonyl)amino-1,1'-biphenyl (239 mg, 0.93 mmol) in methylene chloride (4 mL) was treated with bromotrimethylsilane (3.0 mL, 22.7 mmol). The reaction mixture was stirred at room temperature for 18 hours. The reaction mixture was diluted with additional methylene chloride and washed with saturated aqueous sodium chloride. After drying over magnesium sulfate, the filtered organic layer was evaporated under vacuum The residue was purified by preparative thin layer chromatography on silica gel, eluting with methylene chloride/methanol (100:3) to give 190 mg of the product.

Step Q:
N-[1-[[2'-[(Methoxycarbonyl)amino][1,1'-biphenyl]-4-yl]methyl]-2,3,4,5-tetrahydro-2-oxo-1H-1-benzazepin-3(R)-yl]-3-t-butoxycarbonylamino-3-methylbutanamide A solution of 222 mg (0.594 mmol) of 3-t-butoxycarbonylamino-3-methyl-N-[2,3,4,5-tetrahydro-2-oxo-1H-1-benzazepin-3(R)-yl]-butanamide (Step I) in 6 mL of dry dimethylformamide was treated with 30 mg of 60% sodium hydride oil dispersion (18 mg NaH, 0.75 mmol, 1.3 eq). The reaction mixture was stirred at room temperature for 30 minutes. To the solution was added 190 mg (0.594 mmol) of solid 4-bromomethyl-2'-(methoxycarbonyl)amino-1,1'-biphenyl. After stirring at room temperature for 1 hour, the reaction mixture was diluted with ethyl acetate followed by 50 mL of water. The organic layer was washed with water (4×), dried over magnesium sulfate, filtered and evaporated under vacuum. The residue was purified by preparative thin layer chromatography on silica gel, eluting with methylene chloride/methanol (100:3) to give 231 mg (0.376 mmol, 63%) of the product. $^1$H NMR (400 MHz, CDCl$_3$): 1.23 (s, 3H), 1.33 (s, 3H), 1.39 (s, 9H), 1.85 (m, 1H), 2.40 (dd, 2H), 2.49 (m, 1H), 2.54 (m, 2H), 3.68 (s, 3H), 4.53 (m, 1H), 4.94 (d, 1H), 5.17 (d, 1H), 6.53 (br s, 1H), 6.66 (d, 1H), 7.2 (m, 12H), 8.09 (d, 1H).

Step R:

N-[1-[[2'-[(Methoxycarbonyl)amino][1,1'-biphenyl]-4-yl]methyl]-2,3,4,5-tetrahydro-2-oxo-1H-1-benzazepin-3(R)-yl]-3-amino-3-methylbutanamide, trifluoroacetate A solution of 86 mg (0.14 mmol) of the intermediate obtained in Step Q in 2 mL of methylene chloride was treated with 1.0 mL of trifluoroacetic acid. After stirring at room temperature for 1 hour, all volatiles were removed under vacuum and the residue purified by medium pressure liquid chromatography on C8, eluting with methanol/0.1% aqueous trifluoroacetic acid (60:40). The fractions containing the product were combined and solvents removed under vacuum. The residue was lyophilized from water to give 69 mg (0.13 mmol, 96%) of the title compound as a white solid. FAB-MS: calculated for C$_{30}$H$_{34}$N$_4$O$_4$ 514; found 515(M+H). $^1$H NMR (400 MHz, CD$_3$OD): 1.34 (s, 3H), 1.39 (s, 3H), 2.12 (m, 1H), 2.31 (m, 1H), 2.52 (dd, 2H), 2.6 (m, 2H), 3.54 (br s, 3H), 4.40 (dd, 1H), 5.02 (d, 1H), 5.28 (d, 1H), 7.30 (m, 12H), 7.54 (br s, 1H).

EXAMPLE 2

N-[1-[[2'-[(Methylaminocarbonyl)amino][1,1'-biphenyl]-4-yl]methyl]-2,3,4,5-tetrahydro-2-oxo-1H-1-benzazepin-3(R)-yl]-3-amino-3-methylbutanamide, trifluoroacetate Step A:

N-[1-[[(2'-Nitro)[1,1'-biphenyl]-4-yl]methyl]-2,3,4,5-tetrahydro-2-oxo-1H-1-benzazepin-3(R)-yl]-3-t-butoxycarbonylamino-3-methylbutanamide Prepared from 4-bromomethyl-2'-nitro-1,1'-biphenyl (Example 1, Step K) and 3-t-butoxycarbonylamino-3-methyl-N-[2,3,4,5-tetrahydro-2-oxo-1H-1-benzazepin-3(R)-yl]-butanamide (Example 1, Step I) by the procedure described in Example 1, Step Q. $^1$H NMR (400 MHz, CDCl$_3$): 1.34 (s, 6H), 1.41 (s, 9H), 1.83 (m, 1H), 2.35–2.70 (m, 5H), 4.50 (m, 1H), 4.84 (d, 15 Hz, 1H), 5.23 (d, 15 Hz, 1H), 5.27 (s, 1H), 6.64 (d, 7 Hz, 1H), 7.1–7.6 (m, 11H), 7.80 (d, 8 Hz, 1H). FAB-MS: calculated for C$_{33}$H$_{38}$N$_4$O$_6$ 586; found 587(M+H).

Step B:

N-[1-[[(2'-Amino)[1,1'-biphenyl]-4-yl]methyl]-2,3,4,5-tetrahydro-2-oxo-1H-1-benzazepin-3(R)-yl]-3-t-butoxycarbonylamino-3-methylbutanamide A solution of 7.79 g (13.23 mmol) of the intermediate obtained in Step A in 200 mL of methanol containing 0.9 g of 5% palladium on carbon was hydrogenated at 40 psi. When the uptake of hydrogen was complete, the catalyst was removed by filtration through Celite. The filtrate was concentrated under vacuum to yield 6.6 g (11.9 mmol, 90%) of product. FAB-MS: calculated for C$_{33}$H$_4$N$_4$O$_4$ 556; found 557(M+H). $^1$H NMR (400 MHz, CDCl$_3$): 1.32 (s, 6H), 1.39 (s, 9H), 1.87 (m, 1H), 2.51 (dd, 1H), 2.59 (m, 1H), 4.51 (m, 1H), 4.89 (d, 1H), 5.15 (d, 1H), 5.32 (br s, 1H), 6.71 (d, 1H), 6.81 (s, 1H), 7.21 (m, 10H).

Step C:

N-[1-[[2'-[(Methylaminocarbonyl)amino][1,1'-biphenyl]-4-yl]methyl]-2,3,4,5-tetrahydro-2-oxo-1H-1-benzazepin-3(R)-yl]-3-t-butoxycarbonylamino-3-methylbutanamide A solution of 88.4 mg (0.158 mmol) of the intermediate obtained in Step B in 4 mL of methylene chloride at room temperature was treated with 0.5 mL of methyl isocyanate (8.5 mmol). The reaction mixture was stirred at room temperature for 18 hours, when all starting material was consumed as indicated by thin layer chromatography. The reaction was evaporated under vacuum and the residue passed over silica gel. Elution with ethyl acetate/n-hexane (3:1) yielded 66 mg (0.11 mmol, 68%) of product. $^1$H NMR (400 MHz, CDCl$_3$): 1.21 (s, 3H), 1.23 (s, 3H), 1.39 (s, 9H), 1.89 (m, 1H), 2.49 (dd, H), 2.60 (m, 2H), 2.69 (s, 3H), 4.50 (m, 1H), 4.95 (d, 1H), 5.06 (d, 1H), 5.26 (br s, 1H), 6.24 (br s, 1H), 6.70 (d, 1H), 7.22 (m, 11H), 7.71 (d, 1H).

Step D:

N-[1-[[2'-[(Methylaminocarbonyl)amino][1,1'-biphenyl]-4-yl]methyl]-2,3,4,5-tetrahydro-2-oxo-1H-1-benzazepin-3(R)-yl]-3-amino-3-methylbutanamide, trifluoroacetate A solution of 66 mg (0.11 mmol) of the intermediate obtained in Step C in 2 mL of methylene chloride was treated with 2 mL of trifluoroacetic acid. The reaction mixture was stirred at room temperature for 1 hour, when thin layer chromatography indicated that no starting material remained. The reaction mixture was evaporated to dryness under vacuum and the residue purified by medium pressure liquid chromatography on C8, eluting with methanol/0.1% aqueous trifluoroacetic acid (60:40). Fractions containing the product were combined and evaporated under vacuum and the residue lyophilized from water to give 26 mg (0.051 mmol, 46%) of the title compound as a white solid. FAB-MS: calculated for C$_{30}$H$_{35}$N$_5$O$_3$ 513; found 536 (M+Na). $^1$H NMR (400 MHz, CD$_3$OD): 1.34 (s, 3H), 1.37 (s, 3H), 2.13 (m, 1H), 2.39 (m, 1H), 2.54 (dd, 1H), 2.63 (s, 3H), 3.29 (dd, 1H), 4.95 (d, 1H), 5.11 (d, 1H), 7.22 (m, 10H), 7.60 (d, 1H).

EXAMPLE 3

N-[1-[[2'-[(Ethylaminocarbonyl)amino][1,1'-biphenyl]-4-yl]methyl]-2,3,4,5-tetrahydro-2-oxo-1H-1-benzazepin-3(R)-yl]-3-amino-3-methylbutanamide, trifluoroacetate Step A:

N-[1-[[2'-[(Ethylaminocarbonyl)amino][1,1'-biphenyl]-4-yl]methyl]-2,3,4,5-tetrahydro-2-oxo-1H-1-1-benzazepin-3(R)-yl]-3-t-butoxycarbonylamino-3-methylbutanamide Prepared from N-[1-[[(2'-amino)[1,1'-biphenyl]-4-yl]methyl]-2,3,4,5-tetrahydro-2-oxo-1H-1-benzazepin-3(R)-yl]-3-t-butoxycarbonylamino-3-methylbutanamide (Example 2, Step B) and ethyl isocyanate by the procedure described in Example 2, Step C.

Step B:

N-[1-[[2'-[(Ethylaminocarbonyl)amino][1,1'-biphenyl]-4-yl]methyl]-2,3,4,5-tetrahydro-2-oxo-1H-1-benzazepin-3(R)-yl]-3-amino-3-methylbutanamide, trifluoroacetate Prepared from the intermediate obtained in Step A by the procedure described in Example 2, Step D. FAB-MS: calculated for C$_{31}$H$_{37}$N$_5$O$_3$ 527; found 550(M+Na). $^1$H NMR (400 MHz, DC$_3$OD): 1.04 (t, 3H), 1.34 (s, 3H), 1.38 (s, 3H), 2.14 (m, 1H), 2.34 (m, 1H), 2.52 (dd, 2H), 2.62 (m, 2H), 3.09 (q, 2H), 4.41 (dd, 1H), 5.01 (d, 1H), 5.24 (d, 1H), 7.24 (m, 11H), 7.60 (d, 1H).

EXAMPLE 4

N-[1-[[2'-[(2-Propylaminocarbonyl)amino][1,1'-biphenyl]-4-yl]methyl]-2,3,4,5-tetrahydro-2-oxo-1H-1-benzazepin-3(R)-yl]-3-amino-3-methylbutanamide, trifluoracetate

Step A:

N-[1-[[2'-[(2-Propylaminocarbonyl)amino]-[1,1'-biphenyl]-4-yl]methyl]-2,3,4,5-tetrahydro-2-oxo-1H-1-benzazepin-3(R)-yl]-3-t-butoxycarbonylamino-3-methylbutanamide Prepared from N-[1-[[(2'-amino)[1,1'-biphenyl]-4-yl]methyl]-2,3,4,5-tetrahydro-2-oxo-1H-1-benzazepin-3(R)-yl]-3-t-butoxycarbonylamino-3-methyl-butanamide (Example 2, Step B) and isopropyl isocyanate by the procedure described in Example 2, Step C. $^1$H NMR (400 MHz, CDCl$_3$): 1.06 (d, 3H) 1.07 (d, 3H), 1.32 (s, 3H), 1.39 (s, 9H), 1.88 (m, 1H), 2.48 (dd, 1H), 2.50 (m, 1H), 2.62 (m, 2H), 3.80 (m, 1H), 4.52 (m, 1H), 4.98 (d, 1H), 5.10 (d, 1H), 5.28 (br s, 1H), 6.08 (br s, 1H), 6.68 (br s, 1H), 7.22 (m, 11H), 7.70 (d, 1H).

Step B:

N-[1-[[2'-[(2-Propylaminocarbonyl)amino][1,1'-biphenyl]-4-yl]methyl]-2,3,4,5-tetrahydro-2-oxo-1H-1-benzazepin-3(R)-yl]-3-amino-3-methylbutanamide, trifluoroacetate Prepared from the intermediate obtained in Step A by the procedure described in Example 2, Step D. FAB-MS: calculated for C$_{32}$H$_{39}$N$_5$O$_3$ 541; found 541(M+). $^1$H NMR (400 MHz, CD$_3$OD): 1.05 (dd, 6H), 1.34 (s, 3H), 1.37 (s, 3H), 2.5 (m, 1H), 2.34 (m, 1H), 2.5 (m, 1H), 2.64 (m, 2H), 3.73 (m, 1H), 4.41 (dd, 1H), 5.02 (d, 1H), 5.24 (d, 1H), 7.3 (m, 12H), 7.63 (d, 1H).

EXAMPLE 5

N-[1-[[2'-[(Aminocarbonyl)amino][1,1'-biphenyl]-4-yl]methyl]-2,3,4,5-tetrahydro-2-oxo-1H-1-benzazepin-3(R)-yl]-3-amino-3-methylbutanamide, trifluoroacetate

Step A:

N-[1-[[2'-[(Aminocarbonyl)amino][1,1'-biphenyl]-4-yl]methyl]-2,3,4,5-tetrahydro-2-oxo-1H-1-benzazepin-3(R)-yl]-3-t-butoxycabonylamino-3-methylbutanamide A solution of 445 mg (0.80 mmol) of N-[1-[[(2'-amino)[1,1'-biphenyl]-4-yl]methyl]-2,3,4,5-tetrahydro-2-oxo-1H-1-benzazepin-3-(R)-yl]-3-t-butoxycarbonylamino-3-methylbutanamide (Example 2, Step B) in 3 mL of methylene chloride under a nitrogen atmosphere was treated with 4 mL (29.5 mmol) of trimethylsilyl isocyanate. The reaction mixture was stirred at room temperature for 18 hours. The reaction mixture was evaporated under vacuum and the residue was passed over silica gel. Elution with ethyl acetate/hexanes (4:1) yielded 211 mg (0.35 mmol, 44%) of product. FAB-MS: calculated for C$_{34}$H$_{41}$N$_5$O$_5$ 599: found 622 (M+Na). $^1$H NMR (400 MHz, CDCl$_3$): 1.31 (s, 3H), 1.38 (s, 3H), 1.39 (s, 9H), 1.90 (m, 1H), 2.48 (dd, 2H), 2.60 (m, 2H), 4.48 (m, 1H), 4.95 (d, 1H), 5.08 (d, 1H), 5.28 (br, s, 1H), 6.66 (br s, 1H), 6.78 (d, 1H), 7.22 (m, 11H), 7.72 (d, 1H).

Step B:

N-[1-[[2'-[(Aminocarbonyl)amino][1,1'-biphenyl]-4-yl]methyl]-2,3,4,5-tetrahydro-2-oxo-1H-1-benzazepin-3(R)-yl]-3-amino-3-methylbutanamide, trifluoroacetate The title compound was prepared from the intermediate obtained in Step A by the procedure described in Example 2, Step D. FAB-MS: calculated for C$_{29}$H$_{33}$N$_5$O$_3$ 499; found 500(M+H). $^1$H NMR (400 MHz, CD$_3$OD): 1.34 (s, 3H), 1.37 (s, 3H), 2.14 (m,1H), 2.34 (m, 1H), 2.50 (dd, 1H), 2.65 (m, 2H), 4.42 (dd, 1H), 5.02 (d, 1H), 5.25 (d, 1H), 7.27 (m, 10, H), 7.60 (d, 1H).

EXAMPLE 6

N-[1-[[2'-[(Morpholinocarbonyl)amino][1,1'-biphenyl]-4-yl]methyl]-2,3,4,5-tetrahydro-2-oxo-1H-1-benzazepin-3(R)-yl]-3-amino-3-methylbutanamide, trifluoroacetate

Step A:

N-[1-[[(2'-Isocyanato)[1,1'-biphenyl]-4-yl]methyl]-2,3,4,5-tetrahydro-2-oxo-1H-1-benzazepin-3(R)-yl]-3-t-butoxycarbonylamino-3-methylbutanamide A solution of 2.0 g (3.6 mmol) of N-[1-[[(2'-amino)[1,1'-biphenyl]-4-yl]methyl]-2,3,4,5-tetrahydro-2-oxo-1H-1-benzazepin-3(R)-yl]-3-t-butoxycarbonylamino-3-methylbutanamide (Example 2, Step B) and 2.0 mL of triethylamine (14 mmol) in 40 mL of methylene chloride under a nitrogen atmosphere was cooled to −10° C. and treated with 2.12 g (7.15 mmol) of triphosgene in one portion. An exotherm occurred. The reaction was stirred at room temperature for 1.5 hours when no starting amine was detected by thin layer chromatography on silica (hexane/ethyl acetate (1:1)). The reaction mixture was diluted with 40 mL of hexane and filtered. The filtrate was passed over 150 g of silica gel and eluted with hexane/ethyl acetate (1:1) to give 1.65 g (2.84 mmol), 79%) of the product. $^1$H NMR (400 MHz, CDCl$_3$): 1.34 (s, 6H), 1.39 (s, 9H), 1.84 ((m, 1H), 2.40 (m, 1H), 2.49 (dd, 1), 2.52 (m, 1H), 4.51 (m, 1H), 4.88 (d, 1H), 5.25 (d, 1H), 5.34 (br s, 1H), 6.71 (d, 1H), 7.20 (m, 12H).

Step B:

N-[1-[[2'-[(Morpholinocarbonyl)amino][1,1'-biphenyl]-4-yl]methyl]-2,3,4,5-tetrahydro-2-oxo-1H-1-benzazepin-3(R)-yl]-3-amino-3-methylbutanamide, trifluoroacetate A solution of 100 mg (0.17 mmol) of the intermediate obtained in Step A in 2 mL of methylene chloride was treated with 0.017 mL of morpholine (0.19 mmol). The reaction mixture was stirred at room temperature for 1 hour when thin layer chromatography showed no remaining isocyanate. To the reaction mixture was added 1 mL of trifluoroacetic acid. The reaction mixture was stirred at room temperature for 0.5 hours. The reaction mixture was evaporated under vacuum and the residue purified by preparative medium pressure reverse phase liquid chromatography on C8, eluting with methanol/0.1% aqueous trifluoroacetic acid (65:35). The fractions containing the product were combined and evaporated under vacuum and the residue was lyophilized from water to afford 88 mg (0.15 mmol, 88%) of the title compound as a white solid. FAB-MS: calculated for C$_{33}$H$_{39}$N$_5$O$_4$ 569; found 592 (M+Na). $^1$H NMR (400 MHz, CD$_3$OD): 1.35 (s, 3H), 1.39 (s, 3H), 2.12 (m, 1H), 2.35 (m, 1H), 2.52 (dd, 2H), 2.60 (m, 2H), 3.25 (m, 4H), 3.54 (m, 4H), 4.40 (dd, 1H), 4.95 (d, 1H), 5.30 (d, 1H), 7.3 (m, 12H).

EXAMPLE 7

N-[1-[[(2'-[(Piperazinocarbonyl)amino][1,1'-biphenyl]-4-yl]methyl]-2,3,4,5-tetrahydro-2-oxo-1H-1-benzazepin-3(R)-yl]-3-amino-3-methylbutanamide, trifluoroacetate The title compound was prepared from N-[1-[[(2'-isocyanato)[1,1'-biphenyl]-4-yl]methyl]-2,3,4,5-tetrahydro-2-oxo-1H-1-benzazepin-3(R)-yl]-3-t-butozycarbonylamino-3-methylbutanamide and piperazine by the methods described in Example 6. FAB-MS: calculated for $C_{33}H_{40}N_6O_3$ 568; found 593 (M+Na). $^1$H NMR (400 MHz, CD$_3$OD): 1.27 (s, 3H), 1.30 (s, 3H), 2.07 (m, 1H), 2.30 (m, 1H), 2.4 (dd, 2H), 2.59 (m, 2H), 3.20 (dd, 4H), 3.30 (dd, 4H), 4.40 (dd, 1H), 4.90 (d, 1H), 5.33 (d, 1H), 7.30 (m, 12H).

EXAMPLE 8

N-[1-[[2'-[[(2-Hydroxyethylamino)carbonyl]amino][1,1'-biphenyl]-4-yl]methyl]-2,3,4,5-tetrahydro-2-oxo-1H-1-benzazepin-3(R)-yl]-3-amino-3-methylbutanamide, trifluoroacetate

Step A:
N-[1-[[2'-Hydroxyethylamino)carbonyl]amino][1,1'-biphenyl]-4-yl]methyl]-2,3,4,5-tetrahydro-2-oxo-1H-1-benzazepin-3(R)-yl]-3-t-butoxycarbonylamino-3-methylbutanamide Prepared from N-[1-[[(2'-isocyanato)[1,1'-biphenyl]-4-yl]methyl]-2,3,4,5-tetrahydro-2-oxo-1H-1-benzazepin-3(R)-yl]-3-t-butoxycarbonylamino-3-methylbutanamide and ethanolamine by the procedure described in Example 6, Step A. FAB-MS: calculated for $C_{36}H_{45}N_5O_6$ 643; found 666 (M+Na). $^1$H NMR (400 MHz, CDCl$_3$): 1.29 (s, 3H), 1.31 (s, 3H), 1.38 (s, 9H), 1.90 (m, 1H), 2.5 (dd, 2H), 2.58 (m, 2H), 2.7 (m, 1H), 3.21 (t, 2H), 3.54 (m, 2H), 4.49 (m, 1H), 4.88 (d, 1H), 5.10 (d, 1H), 6.81 (d, 1H), 7.21 (m, 11H), 7.74 (d, 1H).

Step B:
N-[1-[[2'-[[(2-Hydroxyethylamino)carbonyl]amino][1,1'-biphenyl]-4-yl]methyl]-2,3,4,5-tetrahydro-2-oxo-1H-1-benzazepin-3(R)-yl]-3-amino-3-methylbutanamide, trifluoroacetate Prepared from the intermediate obtained in Step A by the procedure described in Example 6, Step B. FAB-MS: calculated for $C_{31}H_{37}N_5O_4$ 543: found 545. $^1$H NMR (400 MHz, CD$_3$OD): 1.34 (s, 3H), 1.37 (s, 3H), 2.14 (m, 1H), 2.34 (m, 1H), 2.52 (dd, 2H), 2.64 (m, 2H), 3.20 (t, 2H), 3.51 (t, 2H), 4.41 (dd, 1H), 5.02 (d, 1H), 5.20 (d, 1H), 7.24 (m, 11H), 7.62 (d, 1H).

EXAMPLE 9

N-[1-[[2'-[[(2-Hydroxypropylamino)carbonyl]amino][1,1'-biphenyl]-4-yl]methyl]-2,3,4,5-tetrahydro-2-oxo-1H-1-benzazepin-3(R)-yl]-3-amino-3-methylbutanamide, trifluoroacetate The title compound was prepared from N-[1-[[(2'-isocyanato)[1,1'-biphenyl]-4-yl]methyl]-2,3,4,5-tetrahydro-2-oxo-1H-1-benzazepin-3(R)-yl]-3-t-butoxycarbonylamino-3-methylbutanamide and 1-amino-2-propanol by the procedures described in Example 6. FAB-MS: calculated for $C_{32}H_{39}N_5O_4$ 557; found 580 (M+Na). $^1$H NMR (400 MHz, CD$_3$OD): 1.00 (d, 3H), 1.34 (s, 3H), 1.37 (s, 3H), 2.14 (m, 1H), 2.34 (m, 1H), 2.52 (dd, 2H), 2.68 (m, 2H), 3.01 (dd, 1H), 4.41 (dd, 1H), 5.02 (d, 1H), 5.21 (d, 1H), 7.25 (m, 11H), 7.62 (d, 1H).

EXAMPLE 10

N-[1-[[2'-[[(3-Hydroxypropylamino)carbonyl]amino][1,1'-biphenyl]-4-yl]methyl]-2,3,4,5-tetrahydro-2-oxo-1H-1-benzazepin-3(R)-yl]-3-amino-3-methylbutanamide, trifluoroacetate The title compound was prepared from N-[1-[[(2'-isocyanato)[1,1'-biphenyl]-4-yl]methyl]-2,3,4,5-tetrahydro-2-oxo-1H-1-benzazepin-3(R)-yl]-3-t-butoxycarbonylamino-3-methylbutanamide and 3-amino-1-propanol by the procedures described in Example 6. FAB-MS: calculated for $C_{32}H_{39}N_5O_4$ 557; found 580 (M+Na). $^1$H NMR (400 MHz, CD$_3$OD): 1.34 (s, 3H), 1.38 (s, 3H), 1.60 (m, 2H), 2.18 (m, 1H), 2.35 (m, 1H), 2.52 (dd, 2H), 2.65 (m, 3H), 3.39 (m, 2H), 3.52 (m, 2H), 4.42 (dd, 1H), 5.04 (d, 1H), 5.21 (d, 1H), 7.28 (m, 11H), 7.59 (d, 1H).

EXAMPLE 11

N-[1-[[2'-[[(2,3-Dihydroxypropylamino)carbonyl]amino]-[1,1'-biphenyl]-4-yl]methyl]-2,3,4,5-tetrahydro-2-oxo-1H-1-benzazepin-3(R)-yl]-3-amino-3-methylbutanamide, trifluoroacetate The title compound was prepared from N-[1-[[(2'-isocyanato)[1,1'-biphenyl]-4-yl]methyl]-2,3, 4,5-tetrahydro-2-oxo-1H-1-benzazepin-3(R)-yl]-3-t-butoxy-carbonylamino-3-methylbutanamide and 3-amino-1,2-propanediol by the procedures described in Example 6. FAB-MS: calculated for $C_{32}H_{39}N_5O_4$ 557; found 580(M+Na). $^1$H NMR (400 MHz, CD$_3$OD): 1.34 (s, 3H), 1.37 (s, 3H), 2.14 (m, 1H), 2.34 (m, 1H), 2.51 (dd, 1H), 2.66 (m, 2H), 3.09 (m, 1H), 3.2 (m, 2H), 3.42 (m, 2H), 3.59 (m, 1H), 4.41 (dd, 1H), 5.05 (d, 1H), 5.17 (d, 1H), 7.25, (m, 10H), 7.59 (d, 1H).

EXAMPLE 12

N-[1-[[2'-[(Methylaminocarbonyl)oxy][1,1'-biphenyl]-4-yl]methyl]-2,3,4,5-tetrahydro-2-oxo-1H-1-benzazepin-3(R)-yl]-3-amino-3-methylbutanamide, trifluoroacetate

Step A: 4-Methylphenyltrimethylstannane 41.4L of 1.0M p-tolylmagnesium bromide in diethyl ether (41.4 mol) was added dropwise, maintaining the temperature below −5° C., over 4 hours to a solution of 546 g (2.79 mol) of trimethyltin chloride in tetrahydrofuran (4 L) under nitrogen at −10° C. The suspension was allowed to warm slowly to room temperature over 12 hours then saturated ammonium chloride solution (1 L) was added followed by sufficient water (approximately 1 L) to dissolve the precipitate. The solution was extracted with ether-hexane (1:1) (1×4 L, 3×2 L). The combined organic phases were washed with brine, dried over magnesium sulfate and the solvents removed under vacuum. Purification by flash chromatography on silica gel eluting with hexane/ethyl acetate (95:5) gave a pale yellow oil containing white crystals of 4,4'-dimethylbiphenyl which were removed by filtration to leave 711.3 g (100%) of product. $^1$H NMR (300 MHz, CDCl$_3$): 0.30 (s, 9H), 2.34 (s, 3H), 7.19 (d, 7.7 Hz, 2H), 7.40 (d, 7.7 Hz, 2H).

Step B: 4-Methyl-2'-acetyl-1,1'-biphenyl

A vigorously stirred solution of 13.25 g (66 mmol) of 2'-bromoacetophenone and 22.8 g (89 mmol) of 4-methylphenyltrimethylstannane in 190 mL of dimethylformamide under a nitrogen atmosphere was treated with 8.64 g (12 mmol) of bis(triphenylphosphine)palladium(II) chloride and the resulting mixture heated at 150° C. for 6 hours. The reaction mixture was cooled, poured into water (1000 mL) and the resultant suspension extracted with ethyl ether. The combined extracts were washed with water (4×), dried over magnesium sulfate and evaporated under vacuum. The residue was purified by preparative high pressure liquid chromatography on silica gel, eluting with hexane/ethyl acetate (10:1) to give 9.8 g (47 mmol, 71%) of product as an oil. EI-MS: calculated for $C_{15}H_{14}O$ 210: found 210 (M+). $^1$H NMR (200 MHz, CDCl$_3$): 1.98 (s, 3H), 2.37 (s, 3H), 7.20 (s, 4H), 7.3–7.5 (m, 4H).

Step C: 4-Methyl-2'-hydroxy-1,1'-biphenyl

A solution of 4.2 g (20.0 mmol) of 4-methyl-2'-acetyl-1-1'-biphenyl (Step B) in methylene chloride under a nitrogen atmosphere was treated with 8.98 g of 85% m-chloro perbenzoic acid. The resultant suspension was cooled to 0° C. and treated dropwise with 1.54 mL of trifluoroacetic acid over a 10 minute period. The reaction mixture was stirred at room temperature for 16 hours. The reaction mixture was diluted with 50 mL of methylene chloride and the solution was washed successively with 50 mL of 10% sodium sulfite, 50 mL of saturated aqueous potassium carbonate and water (3×50 mL). The organic layer was removed and dried over magnesium sulfate, then evaporated under vacuum to yield 4.1 g of an oil. The oil was dissolved in 20 mL of methanol and treated with 2.0 mL of 5N aqueous sodium hydroxide. The reaction mixture was stirred at room temperature for 1 hour. The pH of the solution was adjusted to 5-6 with acetic acid. After the methanol was removed under vacuum, the residue was taken up in ether, washed with water, dried over magnesium sulfate, filtered and evaporated under vacuum to yield 3.0 g of crude product which was purified by preparative high pressure liquid chromatography on silica, eluting with hexane/ethyl acetate (10:1). In this manner, 1.85 g (10.0 mmol, 50%) of the product was obtained as an oil. $^1$H NMR (200 MHz, CDCl$_3$): 2.40 (s, 3H), 5.22 (br s, 1H), 6.96 (m, 2H), 7.2–7.4 (m, 6H). EI-MS: calculated for $C_{13}H_{12}O$ 184; found 184 (M+, 100%).

Step D: 4-Methyl-2'-acetoxy-1,1'-biphenyl

A solution of 1.0 g (5.4 mmol) of 4-methyl-2'-hydroxy-1,1'-biphenyl in 2.0 mL of pyridine was treated with 2 mL of acetic anhydride. The reaction mixture was stirred at room temperature for 5 hours. The solvent was removed under vacuum to yield 1.11 g (4.9 mmol, 90%) of the product as an oil. $^1$H NMR (200 MHz, CDCl$_3$): 2.07 (s, 3H), 2.36 (s, 3H), 7.07 (dd; 3, 8 Hz; 1H), 7.15 (d, 8 Hz, 2H), 7.2–7.4 (m, 5H).

Step E: 4'-Bromomethyl-2-acetoxy-1,1'-biphenyl

Prepared from 4-methyl-2'-acetoxy-1,1'-biphenyl by the procedure described in Example 1, Step K. $^1$H NMR (200 MHz, CDCl$_3$): 2.05 (s, 3H), 4.50 (s, 2H), 7.08 (m, 1H), 7.20–7.45 (m, 7H).

Step F: N-[1-[[2'-(Acetoxy)[1,1'-biphenyl]-4-yl]methyl]-[2,3,4,5-tetrahydro-2-oxo-1H-1-benzazepin-3(R)-yl]-3-t-butoxycarbonylamino-3-methylbutanamide Prepared from 4-bromomethyl-2'-acetoxy-1,1'-biphenyl and 3-t-butoxycarbonylamino-3-methyl-N-[2,3,4,5-tetrahydro-2-oxo-1H-1-benzazepin-3(R)-yl]butanamide (Example, 1, Step I) by the procedure described in Example 1, Step Q. $^1$H NMR (200 MHz, CDCl$_3$): 1.38 (s, 6H), 1.45 (s, 1.45 (s, 9H), 1.85 (m, 1H), 2.02 (s, 3H), 2.35–2.65 (m, 5H), 4.52 (m, 1H), 4.84 (d, 15 Hz, 1H), 5.30 (d, 15 Hz, 1H), 6.71 (d, 7 Hz, 1H), 7.1–7.4 (m, 12H).

Step G: N-[1-[[(2'-Hydroxy)[1,1'-biphenyl]-4-yl]methyl]-2,3,4,5-tetrahydro-2-oxo-1H-1-benzazepin-3(R)-yl]-3-t-butoxycarbonylamino-3-methylbutanamide A solution of 469 mg (0.87 mmol) of the intermediate obtained in Step F in 25 mL of methanol at room temperature was treated with 5 mL of aqueous 5N sodium hydroxide. After stirring at room temperature for 1 hour, the reaction mixture was evaporated under vacuum and the residue dissolved in methylene chloride, dried over magnesium sulfate and filtered. The filtrate was evaporated under vacuum to yield 450 mg of crude product which was used in the next step without purification.

Step H: N-[1-[[2'-[(Methylaminocarbonyl)oxy][1,1'-biphenyl]-4-yl]methyl]-2,3,4,5-tetrahydro-2-oxo-1H-1-benzazepin-3(R)-yl]-3-t-butoxycarbonylamino-3-methylbutanamide A solution of 100 mg (approx. 0.2 mmol) of the crude intermediate obtained in Step G in 5 mL of methylene chloride was treated with 1.0 mL of methyl isocyanate (17 mmol) and 0.1 mL of 1,8-diazabicyclo[5.4.0]undec-7-ene under a nitrogen atmosphere. The reaction mixture was stirred at room temperature for 10 minutes and then evaporated under vacuum to give 146 mg ofo crude product. $^1$H NMR (400 MHz, CDCl$_3$): 1.32 (s, 3H), 1.33 (s, 3H), 1.39 (s, 9H), 2.12 (m, 1H), 2.33 (m, 1H), 2.52 (dd, 1H), 2.57 (m, 2H), 2.59 (s, 3H), 4.38 (dd, 1H), 4.8 (d, 1H), 5.26 (d, 1H), 7.10 (d, 1H), 7.36 (m, 11H).

Step I: N-[1-[[2'-[(Methylaminocarbonyl)oxy][1,1'-biphenyl]-4-yl]methyl]-2,3,4,5-tetrahydro-2-oxo-1H-1-benzazepin-3(R)-yl]-3-amino-3-methylbutanamide, trifluoroacetate A solution of 72 mg of the crude intermediate obtained in Step H in 3.5 mL of methylene chloride was treated with 1.0 mL of trifluoroacetic acid. After stirring at room temperature for 15 minutes, the reaction mixture was evaporated under vacuum and the residue purified by reverse phase medium pressure liquid chromatography on C8, eluting with methanol/0.1% aqueous trifluoroacetic acid (60:40). Fractions containing the product were combined, solvents removed under vacuum and the residues lyophilized from water to give 34 mg (0.066 mmol) of the title compound as a white solid. FAB-MS: calculated for $C_{30}H_{34}N_4O_4$ 514; found 537 (M+Na). $^1$H NMR (400 MHz, CD$_3$OD): 1.34 (s, 3H), 1.38 (s, 3H), 2.12 (m, 1H), 2.33 (m, 1H), 2.52 (dd, 1H), 2.57 (m, 2H), 2.59 (s, 3H), 4.38 (dd, 1H), 4.8 (d, 1H), 5.26 (d, 1H), 7.10 (d, 1H), 7.36 (m, 11H).

EXAMPLE 13

N-[1-[[2'-[(Methylaminocarbonyl)amino][1,1'-biphenyl]-4-yl]methyl]-2,3,4,5-tetrahydro-2-oxo-1H-1-benzazepin-3(R)-yl]-3-amino-3-methylbutanamide, trifluoroacetate

Step A:
N-[1-[[(2'-Isothiocyanato)[1,1'-biphenyl]-4-yl]methyl]-2,3,4,5-tetrahydro-2-oxo-1H-1-benzazepin-3(R)-yl]-3-t-butoxycarbonylamino-3-methylbutanamide, and
N-[1-[[2'-[(Methylaminothiocarbonyl)amino][1,1'-biphenyl]-4-yl]methyl]-2,3,4,5-tetrahydro-2-oxo-1H-1-benzazepin-3(R)-yl]-3-t-butoxycarbonylamino-3-methyl-butanamide A solution of 300 mg (0.60 mmol) of N-[1-[[(2'-amino)[1,1'-biphenyl]-4-yl]methyl]-2,3,4,5-tetrahydro-2-oxo-1H-1-benzazepin-3(R)-yl]-3-t-butoxycarbonylamino-3-methylbutanamide (Example 2, Step B) and 1.8 g of methyl isothiocyanate (25 mmol) in 15 mL of benzene under a nitrogen atmosphere was heated at reflux for 24 hours. The reaction mixture was evaporated under vacuum and the residue purified by preparative thin layer chromatography on silica gel, eluting with ethyl acetate/hexane (3:1) to give 69 mg of a faster moving product identified as N-[1-[[(2'-isothiocyanato)[1,1'-biphenyl]-4-yl]methyl]-2,3,4,5-tetrahydro-2-oxo-1H-1-benzazepin-3(R)-yl]-3-t-butoxycarbonylamino-3-methylbutanamide. FAB-MS: calculated for $C_{34}H_{38}N_4O_4S$ 598; found 621 (M+Na). $^1$H NMR (400 MHz, CDCl$_3$): 1.35 (s, 3H), 1.36 (s, 3H), 1.40 (s, 9H), 1.84 (m, 1H), 2.48 (dd, 2H), 2.52 (m, 3H), 4.50 (m, 1H), 4.86 (d, 1H), 5.29 (d, 1H), 6.68 (d, 1H), 7.14 (m, 1H), 7.30 (M, 11H).

The slower moving band yielded 122 mg of material identified as N-[1-[[2'-[(methylaminothiocarbonylamino][1,1'-biphenyl]-4-yl]methyl]-2,3,4,5-tetrahydro-2-oxo-1H-1-benzazepin-3(R)-yl]-3-t-butoxycarbonylamino-3-methylbutanamide. FAB-MS: calculated for $C_{35}H_{43}N_5O_4S$ 629: found 652 (M+Na). $^1$H NMR (400 MHz, CDCl$_3$): 1.32 (s, 3H), 1.33 (s, 3H), 1.40 (s, 9H), 1.85 (m, 1H), 2.48 (dd, 2H), 2.55 (m, 3H), 2.95 (s, 3H), 4.50 (m, 1H), 4.88 (s, 1H), 5.20 (s, 1H), 6.68 (d, 1H), 7.22 (m, 12H).

Step B:
N-[1-[[2'-[(Methylaminothiocarbonyl)amino][1,1'-biphenyl]-4-yl]methyl]-2,3,4,5-tetrahydro-2-oxo-1H-1-benzazepin-3(R)-yl]-3-amino-3-methylbutanamide, trifluoroacetate A solution of 122 mg (0.19 mmol) of N-[1-[[2'-[(methylaminothiocarbonyl)amino][1,1'-biphenyl]-4-yl]methyl]-2,3,4,5-tetrahydro-2-oxo-1H-1-benzazepin-3(R)-yl]-3-t-butoxycarbonylamino-3-methylbutanamide in 3 mL of methylene chloride was treated with 1.0 mL of trifluoroacetic acid. After 1 hour thin layer chromatography indicated that no starting material was present. Solvents were removed under vacuum and the residue purified by reverse phase medium pressure liquid chromatography on C8, eluting with methanol/0.1% aqueous trifluoroacetic acid (60:40). The fractions containing the product were combined, solvents evaporated under vacuum and the residue was lyophilized from water to give 84 mg (0.16 mmol, 84%) of the title compound as a white solid. FAB-MS: calculated for $C_{30}H_{35}N_4O_2$ 529 found: 531. $^1$H NMR (400 MHz, CD$_3$OD): 1.32 (s, 3H), 1.38 (s, 3H), 2.11 (m, 1H), 2.30 (m, 1H), 2.53 (dd, 2H), 2.70 (m, 2H), 2.72 (s, 3H), 4.4 (dd, 1H), 4.89 (d, 1H), 5.81 (d, 1H), 7.3 (m, 12H).

EXAMPLE 14

N-[1-[[2'-[(Aminothiocarbonyl)amino][1,1'-biphenyl]-4-yl]methyl]-2,3,4,5-tetrahydro-2-oxo-1H-1-benzazepin-3(R)-yl]-3-amino-3-methylbutanamide, trifluoroacetate A solution of 100 mg (0.17 mmol) of N-[1-[[(2'-isothiocyanato)[1,1'-biphenyl]-4-yl]methyl]-[2,3,4,5-tetrahydro-2-oxo-1H-1-benzazepin-3(R)-yl]-3-t-butoxycarbonylamino-3-methylbutanamide (Example 13, Step A) in 5 mL of methanol was treated with gaseous anhydrous ammonia for 5 minutes. Thin layer chromatography revealed no starting isothiocyanate was present. The reaction mixture was evaporated under vacuum and the residue was dissolved in 3 mL of methylene chloride and treated with 1 mL of trifluoroacetic acid. After 1 hour at room temperature the reaction mixture was evaporated under vacuum and the residue purified by reverse phase medium pressure liquid chromatography on C8, eluting with methanol/0.1% aqueous trifluoroacetic acid (60:40). Fractions containing the product were combined, solvents removed under vacuum and the residue lyophilized from water to give 53 mg of the title compound as a white solid. FAB-MS: calculated for $C_{29}H_{33}N_5O_2S$ 515; found 516 (M+H). $^1$H NMR (400 MHz, CD$_3$OD): 1.34 (s, 3H), 1.38 (s, 3H), 2.12 (m, 1H), 2.30 (m, 1H), 2.54 (dd, 2H), 2.60 (m, 2H), 4.42 (dd, 1H), 4.92 (d, 1H), 5.26 (d, 1H), 7.30 (m, 12H).

EXAMPLE 15

N-[1-[[2'-[(Dimethylaminocarbonyl)amino][1,1'-biphenyl]-4-yl]methyl]-2,3,4,5-tetrahydro-2-oxo-1H-1-benzazepin-3(R)-yl]-3-amino-3-methylbutanamide, trifluoroacetate

Step A:
4-(Tetrahydropyranyloxy)methyl-2'-isocyanato-1,1'-biphenyl

A solution of 200 mg (0.70 mmol) of 4-(tetrahydropyranyloxy)methyl-2'-amino-1,1'-biphenyl (Example 1, Step N) and 0.40 mL of triethylamine in 10 mL of methylene chloride under a nitrogen atmosphere was treated with triphosgene (420 mg, 0.24 mmol). The reaction mixture was stirred at room temperature for 30 minutes when thin layer chromatography on silica (hexane/ethyl acetate; 2:1) revealed no remaining amine. The reaction mixture was evaporated under vacuum to yield the crude product which was used in the next step without purification.

Step B:
4-Hydroxymethyl-2'-(dimethylaminocarbonyl)amino-1,1'-biphenyl

A solution of the crude intermediate from Step A in 4 mL of methanol was treated with 4 mL of 40% aqueous dimethylamine. After stirring at room temperature for 15 minutes, the reaction mixture was evaporated under vacuum and the residue dissolved in 4 mL of methanol and treated with 1 mL of 10% methanolic p-toluenesulfonic acid. After 15 minutes at room temperature, the reaction mixture was treated with saturated aqueous sodium bicarbonate. The mixture was diluted with water then extracted with methylene chloride. The organic layer was dried and evaporated under vacuum; the residue was purified by preparative thin layer chromatography on silica gel, eluting with hexane/ethyl acetate (2:1) to afford 133 mg of product.

Step C:
4-Bromomethyl-2'-(dimethylaminocarbonyl)amino-1,1'-biphenyl

A solution of the intermediate obtained in Step B in 4 mL of methylene chloride was treated with 0.16 mL (1.21 mmol) of trimethylsilylbromide. The reaction mixture was stirred at room temperature for 18 hours. The reaction mixture was diluted with methylene chloride then washed with aqueous saturated sodium chloride (2×). The organic layer was dried over magnesium sulfate, filtered and evaporated under vacuum to yield 133 mg of crude product. $^1$H NMR (400 Hz, CDCl$_3$): 2.78 (s, 6H), 4.5 (s, 2H), 6.4 (br s, 1H), 7.08 (t, 1H), 7.16 (dd, 1H), 7.34 (m, 4H), 7.49 (d, 1H), 8.10 (d, 1H).

Step D:
N-[1-[[2'-[(Dimethylaminocarbonyl)amino][1,1'-biphenyl]-4-yl]methyl]-2,3,4,5-tetrahydro-2-oxo-1H-1-benzazepin-3(R)-yl]-3-amino-3-methylbutanamide, trifluoroacetate A solution of 147 mg (0.39 mmol) of 3-t-butoxycarbonylamino-3-methyl-N-[2,3,4,5-tetrahydro-2-oxo-1H-1-benzazepin-3(R)-yl]-butanamide (Example 1, Step I) in 5 mL of dry dimethylformamide was treated with 20 mg of 60% sodium hydride/oil dispersion (12 mg NaH, 0.5 mmol, 1.3 eq.). The reaction mixture was stirred at room temperature for 30 minutes then 133 mg of 4-bromomethyl-2'-(dimethylaminocarbonyl)amino-1,1'-biphenyl was added. After stirring at room temperature for 2 hours, the reaction mixture was diluted with ethyl acetate. The mixture was washed with water (4×) and the organic layer dried over magnesium sulfate, filtered and evaporated under vacuum. The residue was dissolved in 4 mL of methylene chloride and treated with 1 mL of trifluoroacetic acid. After stirring at room temperature for 1.5 hours, solvents were removed under vacuum and the residue purified by reverse phase medium pressure liquid chromatography on C8, eluting with methanol/0.1% aqueous trifluoroacetic acid (65:35). Fractions containing the product were combined, solvents removed under vacuum and the residue lyophilized from water to give 116 mg of the title compound as a white solid. FAB-MS: calculated for C$_{31}$H$_{37}$N$_5$O$_3$ 527; found 529. $^1$H NMR (400 MHz, CD$_3$OD): 1.34 (s, 3H), 1.40 (s, 3H), 2.15 (m, 1H), 2.34 (m, 1H), 2.54 (dd, 2H), 2.59 (m, 2H), 2.78 (s, 6H), 4.44 (dd, 1H), 4.88 (d, 1H), 5.38 (d, 1H), 7.28 (m, 11H), 7.49 (d, 1H).

EXAMPLE 16

N-[1-[[2'-[[(1,3-Dihydroxyprop-2-yl)aminocarbonyl]amino][1,1'-biphenyl]-4-yl]methyl]-2,3,4,5-tetrahydro-2-oxo-1H-1-benzazepin-3(R)-yl]-3-amino-3-methylbutanamide, trifluoroacetate

Step A:
N-[1-[[2'-[(1,3-Dihydroxyprop-2-yl)aminocarbonyl]amino][1,1'-biphenyl]-4-yl]methyl]-2,3,4,5-tetrahydro-2-oxo-1H-1-benzazepin-3(R)-yl]-3-t-butoxycarbonylamino-3-methylbutanamide A solution of 125 mg (0.23 mmol) of N-[1-[(2'-amino)[1,1'-biphenyl]-4-yl]methyl]-2,3,4,5-tetrahydro-2-oxo-1H-1-benzazepin-3(R)-yl]-3-t-butoxycarbonylamino-3-methylbutanamide (Example 2, Step B) and 0.10 mL (0.72 mmol) of triethylamine in 5 mL of methylene chloride under a nitrogen atmosphere was cooled to −10° C. and treated with 133 mg (0.45 mmol) of triphosgene. The reaction mixture was allowed to warm to room temperature and stirred for 1 hour. The reaction mixture was recooled to −10° C. and additional triethyl amine (0.30 mL, 0.23 mmol) was added. The reaction mixture was treated with serinol hydrochloride (280 mg, 2.20 mmol) in one portion. The reaction mixture was stirred at room temperature when thin layer chromatography (hexane/ethyl acetate: 1:1) indicated no remaining isocyanate. The reaction mixture was evaporated under vacuum to give the crude product.

Step B:
N-[1-[[2'-[[(1,3-Dihydroxyprop-2-yl)aminocarbonyl]amino][1,1'-biphenyl]-4-yl]methyl]-2,3,4,5-tetrahydro-2-oxo-1H-1-benzazepin-3(R)-yl]-3-amino-3-methylbutanamide, trifluoroacetate A solution of the crude intermediate obtained in Step A in 5 mL of methylene chloride was treated with 2 mL of trifluoroacetic acid. After stirring at room temperature for 1 hour, the reaction mixture was evaporated under vacuum and the residue purified by reverse phase medium pressure liquid chromatography on C8, eluting with methanol/0.1% aqueous trifluoroacetic acid (55:45). Fractions containing the product were combined, solvents removed under vacuum and the residue lyophilized from water to give 66 mg (0.096 mmol, 42% over two steps) of the title compound as a white solid. FAB-MS: calculated for C$_{32}$H$_{39}$N$_5$O$_5$ 573; found 596 (M+Na). $^1$H NMR (400 MHz, CD$_3$OD): 1.34 (s, 3H), 1.37 (s, 3H), 2.14 (m, 1H), 2.30 (m, 1H), 2.48 (dd, 2H), 2.69 (m, 2H), 3.52 (m, 4H), 3.70 (m, 1H), 4.40 (dd, 1H), 5.05 (d, 1H), 5.20 (d, 1H), 7.25 (m, 11H), 7.62 (d, 1H).

EXAMPLE 17

N-[1-[[2'-[[(2(R)-Hydroxypropylamino)carbonyl]amino][1,1'-biphenyl]-4-yl]methyl]-2,3,4,5-tetrahydro-2-oxo-1H-1-benzazepin-3(R)-yl]-3-amino-3-methylbutanamide, trifluoroacetate The title compound was prepared from N-[1-[[(2'-isocyanato)[1,1'-biphenyl]-4-yl]methyl]-2,3,4,5-tetrahydro-2-oxo-1H-1-benzazepin-3(R)-yl]-3-t-butoxycarbonylamino-3-methylbutanamide and (R)-(−)-1-amino-2-propanol by the methods described in Example 6. FAB-MS: calculated for C$_{32}$H$_{39}$N$_5$O$_4$ 557; found 580 (M+Na). $^1$H NMR (400 MHz, CD$_3$OD): 1.09 (d, 3H), 1.34 (s, 3H), 1.37 (s, 3H), 2.15 (m, 1H), 2.35 (m, 1H), 2.52 (dd, 2H), 2.65 (m, 2H), 2.95 (dd, 1H), 3.16 (dd, 1H), 3.75 (m, 1H), 4.82 (dd, 1H), 5.02 (d, 1H), 5.20 (d, 1H), 7.27 (m, 11H), 7.61 (d, 1H).

EXAMPLE 18

N-[1-[[2'-[[(2(S)-Hydroxypropylamino)carbonyl]amino][1,1'-biphenyl]-4-yl]methyl]-2,3,4,5-tetrahydro-2-oxo-1H-1-benzazepin-3(R)-yl]-3-amino-3-methylbutanamide, trifluoroacetate The title compound was prepared from N-[1-[[(2'-isocyanato)[1,1'-biphenyl]-4-yl]methyl]-2,3,4,5-tetrahydro-2-oxo-1H-1-benzazepin-3(R)-yl]-3-t-butoxycarbonylamino-3-methylbutanamide and (S)-(+)-1-amino-2-propanol by the methods described in Example 6. FAB-MS: calculated for C$_{32}$H$_{39}$N$_5$O$_4$ 557; found 581 (M+Na). $^1$H NMR (400 MHz, CD$_3$OD): 1.09 (d, 3H), 1.34 (s, 3H), 1.37 (s, 3H), 2.15 (m, 1H), 2.45 (m, 1H), 2.55 (dd, 2H), 2.68 (m, 2H), 3.02 (dd, 1H), 3.16 (dd, 1H), 3.75

(m, 1H), 4.41 (dd, 1H), 5.06 (d, 1H), 5.22 (d, 1H), 7.27 (m, 11H), 7.62 (d, 1H).

EXAMPLE 19

N-[1-[[2'-[[[(1-Hydroxyprop-2(R)-yl)amino]carbonyl]amino][1,1'-biphenyl]-4-yl]methyl]-2,3,4,5-tetrahydro-2-oxo-1H-1-benzazepin-3(R)-yl]-3-amino-3-methylbutanamide, trifluoroacetate The title compound was prepared from N-[1-[[(2'-isocyanato)[1,1'-biphenyl]-4-yl]methyl]-2,3,4,5-tetrahydro-2-oxo-1H-1-benzazepin-3(R)-yl]-3-t-butoxycarbonylamino-3-methylbutanamide and (R)-2-amino-1-propanol by the methods described in Example 6. FAB-MS: calculated for $C_{32}H_{39}N_5O_4$ 557; found 580 (M+Na). $^1$H NMR (400 MHz, CD$_3$OD): 1.07 (d, 3H), 1.34 (s, 3H), 1.37 (s, 3H), 2.15 (m, 1H), 2.35 (m, 1H), 2.51 (dd, 1H), 3.41 (m, 2H), 3.75 (m, 1H), 4.41 (dd, 1H), 5.03 (d, 1H), 5.21 (d, 1H), 7.25 (m, 11H), 7.64 (d, 1H).

EXAMPLE 20

N-[1-[[2'-[(Hydrazinocarbonyl)amino][1,1'-biphenyl]-4-yl]methyl]-2,3,4,5-tetrahydro-2-oxo-1H-1-benzazepin-3(R)-yl]-3-amino-3-methylbutanamide, trifluoroacetate The title compound was prepared from N-[1-[[(2'-isocyanato)[1,1'-biphenyl]-4-yl]methyl]-2,3,4,5-tetrahydro-2-oxo-1H-1-benzazepin-3(R)-yl]-3-t-butoxycarbonylamino-3-methylbutanamide and anhydrous hydrazine by the methods described in Example 6. FAB-MS: calculated for $C_{29}H_{35}N_6O_3$ 514: found 537 (M+Na). $^1$H NMR (400 MHz, CD$_3$OD): 1.35 (s, 3H), 1.38 (s, 3H), 2.29 (m, 1H), 2.35 (m, 1H), 2.57 (dd, 1H), 2.62 (m, 2H), 4.46 (dd, 1H), 5.30 (d, 1H), 7.29 (m, 10H), 7.73 (d, 1H).

EXAMPLE 21

N-[1-[[2'-[(2,2-Dimethylhydrazinocarbonylamino][1,1'-biphenyl]-4-yl]methyl]-2,3,4,5-tetrahydro-2-oxo-1H-1-benzazepin-3(R)-yl]-3-amino-3-methylbutanamide, trifluoroacetate The title compound was prepared from N-[1-[[(2'-isocyanato)[1,1'-biphenyl]-4-yl]methyl]-2,3,4,5-tetrahydro-2-oxo-1H-1-benzazepin-3(R)-yl]-3-t-butoxycarbonylamino-3-methylbutanamide and 1,1-dimethylhydrazine by the methods described in Example 6. FAB-MS: calculated for $C_{31}H_{38}N_6O_3$ 542; found 565 (M+Na). $^1$H NMR (400 MHz, CD$_3$OD): 1.34 (s, 3H), 1.38 (s, 3H), 2.14 (m, 1H), 2.30 (s, 6H), 2.36 (m, 1H), 2.52 (dd, 1H), 2.64 (m, 2H), 4.28 (dd, 1H), 5.00 (dd, 1H), 5.30 (dd, 1H), 7.26 (m, 10H), 7.90 (d, 1H).

EXAMPLE 22

N-[1-[[2'-[[(Carboxymethylamino)carbonyl]amino][1,1'-biphenyl]-4-yl]methyl]-2,3,4,5-tetrahydro-2-oxo-1H-1-benzazepin-3(R)-yl]-3-amino-3-methylbutanamide, trifluoroacetate Step A:
N-[1-[[2'-[[(t-Butoxycarbonylmethylamino)carbonyl]amino][1,1'-biphenyl]-4-yl]methyl]-2,3,4,5-tetrahydro-2-oxo-1H-1-benzazepin-3(R)-yl]-3-t-butoxycarbonylamino-3-methylbutanamide Prepared from N-[1-[[(2'-amino)[1,1'-biphenyl]-4-yl]methyl]-2,3,4,5-tetrahydro-2-oxo-1H-1-benzazepin-3-(R)-yl]-3-t-butoxycarbonylamino-3-methylbutanamide (Example 2, Step B) and glycine t-butyl ester hydrochloride by the procedure described in Example 16, Step A.

Step B:
N-[1-[[2'-[[(Carboxymethylamino)carbonyl]amino][1,1'-biphenyl]-4-yl]methyl]-2,3,4,5-tetrahydro-2-oxo-1H-1-benzazepin-3(R)-yl]-3-amino-3-methylbutanamide, trifluoroacetate, and
N-[1-[[2'-[[(Methoxycarbonylmethylamino)carbonyl]amino][1,1'-biphenyl]-4-yl]methyl]-2,3,4,5-tetrahydro-2-oxo-1H-1-benzazepin-3(R)-yl]-3-amino-3-methylbutanamide, trifluoroacetate, A solution of the crude intermediate obtained in Step A in 4 mL of methylene chloride was treated with 2 mL of trifluoroacetic acid. After stirring at room temperature for 1 hour, the reaction mixture was evaporated under vacuum and the residue purified by reverse phase medium pressure liquid chromatography on C8, eluting with methanol/0.1% aqueous trifluoroacetic acid (55:45). The early fractions containing the product were combined, solvents removed under vacuum and the residue was lyophilized from water to give 60 mg of the title compound as a white solid. FAB-MS: calculated for $C_{31}H_{35}N_5O_5$ 557: found 558 (M+H). $^1$H NMR (400 MHz, CD$_3$OD:) 1.34 (s, 3H), 1.38 (s, 3H), 2.15 (m, 1H), 2.34 (m, 1H), 2.52 (dd, 2H), 2.68 (m, 2H), 3.84 (s, 2H), 4.42 (s, 1H), 5.05 (d, 1H), 5.20 (d, 1H), 7.25 (m, 11H), 7.64 (d, 1H).

Later fractions were combined, solvents removed under vacuum and the residue lyophilized from water to give 18 mg of N-[1-[[2'-[[(methoxycarbonylmethylamino)carbonyl]amino][1,1'-biphenyl]-4-yl]methyl]-2,3,4,5-tetrahydro-2-oxo-1H-1-benzazepin-3(R)-yl]-3-amino-3-methylbutanamide, trifluoroacetate. FAB-MS: calculated for $C_{32}H_{37}N_5O_5$ 571; found 594 (M+Na). $^1$H NMR (400 MHz, CD$_3$OD): 1.34 (s, 3H), 1.39 (s, 3H), 2.15 (m, 1H), 2.35 (m, 1H), 2.52 (dd, 2H), 2.66 (m, 2H), 2.71 (s, 3H), 2.87 (s, 2H), 4.42 (dd, 1H), 5.05 (d, 1H), 5.22 (d, 1H), 7.28 (m, 11H), 7.61 (d, 1H).

EXAMPLE 23

N-[1-[[2'-[[(Methoxycarbonylmethylamino)carbonyl]amino][1,1'-biphenyl]-4-yl]methyl]-2,3,4,5-tetrahydro-2-oxo-1H-1-benzazepin-3(R)-yl]-3-amino-3-methylbutanamide, trifluoroacetate The title compound was prepared from N-[1-[[2'-[-(t-butoxycarbonylmethylamino)carbonyl]amino][1,1'-biphenyl]-4-yl]methyl]-2,3,4,5-tetrahydro-2-oxo-1H-1-benzazepin-3(R)-yl]-3-t-butoxycarbonylamino-3-methylbutanamide by the procedure described in Example 22, Step B. FAB-MS: calculated for $C_{32}H_{37}N_5O_5$ 571; found 594 (M+Na). $^1$H NMR (400 MHz, CD$_3$OD): 1.34 (s, 3H), 1.39 (s, 3H), 2.15 (m, 1H), 2.35 (m, 1H), 2.52 (dd, 2H), 2.66 (m, 2H), 2.71 (s, 3H), 2.87 (s, 2H), 4.42 (dd, 1H), 5.05 (d, 1H), 5.22 (d, 1H), 7.28 (m, 11H), 7.61 (d, 1H).

EXAMPLE 24

N-[1-[[2'-[(Benzylaminocarbonyl)amino][1,1'-biphenyl]-4-yl]methyl]-2,3,4,5-tetrahydro-2-oxo-1H-1-benzazepin-3(R)-yl]-3-amino-3-methylbutanamide, trifluoroacetate The title compound was prepared from N-[1-[[(2'-isocyanato)[1,1'-biphenyl]-4-yl]methyl]-2,3,4,5-tetrahydro-2-oxo-1H-1-benzazepin-3(R)-yl]-3-t-butoxy-carbonylamino-3-methylbutanamide and benzyl amine by the procedures described in Example 6. $^1$H NMR (400 MHz, CD$_3$OD): 1.34 (s,3H), 1.37 (s,3H), 2.13 (m,1H), 2.33 (m,1H), 2.45–2.70 (m,4H), 4.28 (s,2H), 4.42

(dd,1H), 5.00 (d,1H), 5.25 (d,1H), 7.1–7.4 (m,16H), 7.62 (d,1H). FAB-MS: calculated for $C_{36}H_{39}N_5O_3$, 589; found 590 (M+H).

EXAMPLE 25

N-[1-[[2'-[(Phenylaminocarbonyl)amino][1,1'-biphenyl]-4-yl]methyl]-2,3,4,5-tetrahydro-2-oxo-1H-1-benzazepin-3(R)-yl]-3-amino-3-methylbutanamide, trifluoroacetate The title compound was prepared from N-[1-[[(2'-isocyanato)[1,1'-biphenyl]-4-yl]methyl]-2,3,4,5-tetrahydro-2-oxo-1H-1-benzazepin-3(R)-yl]-3-t-butoxycarbonylamino-3-methylbutanamide and aniline by the procedures described in Example 6. FAB-MS: calculated for $C_{35}H_{37}N_5O_3$, 578; found 598 (M+Na). $^1$H NMR (400 MHz,CD$_3$OD): 1.32 (s,3H), 1.35 (s,3H), 2.11 (m,1H), 2.30 (m,1H), 2.52 (m,2H), 2.65 (m,1H), 4.40 (dd,1H), 5.03 (d,1H), 5.21 (d,1H), 6.99 (m,2H), 7.15–7.45 (m,9H), 7.74 (d,1H).

EXAMPLE 26

N-[1-[[2'-[(Hydroxyaminocarbonyl)amino][1,1'-biphenyl]-4-yl]methyl]-2,3,4,5-tetrahydro-2-oxo-1H-1-benzazepin-3(R)-yl]-3-amino-3-methylbutanamide, trifluoroacetate The title compound was prepared from N-[1-[[(2'-isocyanato)[1,1'-biphenyl]-4-yl]methyl]-2,3,4,5-tetrahydro-2-oxo-1H-1-benzazepin-3(R)-yl]-3-t-butoxycarbonylamino-3-methylbutanamide and O-(trimethylsilyl)hydroxylamine by the procedures described in Example 6. FAB-MS: calculated for $C_{29}H_{33}N_5O_4$ 515: found 538 (M+Na). $^1$H NMR (400 MHz, CD$_3$OD): 1.26 (s, 1H), 1.28 (s, 3H), 2.11 (m, 1H), 2.32 (m, 1H), 2.52 (dd, 2H), 2.60 (m, 2H), 4.40 (dd, 1H), 5.0 (d, 1H), 5.24 (d, 1H), 7.25 (m, 11H), 8.0 (d, 1H).

EXAMPLE 27

N-[1-[[2'-[4-[(Methylaminocarbonyl)amino]phenoxy][1,1'-biphenyl]-4-yl]methyl]-2,3,4,5-tetrahydro-2-oxo-1H-1-benzazepin-3(R)-yl]-3-amino-3-methylbutanamide, trifluoroacetate

Step A: 4-Methyl-2'-(4-nitrophenoxy)-1,1'-biphenyl

A solution of 184 mg (1.0 mmol) of 4-methyl-2'-hydroxy-1,1'-biphenyl (Example 12, Step C) in 3 mL of dimethylformamide was treated with 55 mg of 60% sodium hydride (33 mg NaH, 1.4 mmol). The reaction mixture was stirred at room temperature for 30 minutes then treated with 169 mg (1.19 mmol) of 1-fluoro-4-nitrobenzene. The reaction mixture was heated at 100° C. for 2 hours. The reaction mixture was cooled, poured into 50 mL of water and the resultant mixture was extracted with ethyl ether. The combined extracts were washed with water, dried over magnesium sulfate, filtered and evaporated under vacuum. The residue was chromatographed on silica, eluting with hexane/ethyl acetate (10:1) to give 271 mg (0.89 mmol, 88%) of the product. FAB-MS: calculated for $C_{19}H_{15}NO_2$ 305: found 306 (M+H). $^1$H NMR (200 MHz,CDCl$_3$): 2.28 (s,3H), 6.82 (d,2H), 7.19 (d,3H), 7.2–7.5 (m,5H), 8.05 (d,2H).

Step B: 4-Bromomethyl-2'-(4-nitrophenoxy)-1,1'-biphenyl

Prepared from 4-methyl-2'-(4-nitrophenoxy)-1,1'-biphenyl by the procedure described in Example 1, Step K. $^1$H NMR (200 MHz, CDCl$_3$): 4.43 (s,2H), 6.83 (d,8 Hz,2H), 7.09 (d,8 Hz,1H), 7.3–7.5 (m,7H), 8.04 (d,8 Hz,2H).

Step C: N-[1-[[2'-(4-Nitrophenoxy)[1,1'-biphenyl]-4-yl]methyl]-2,3,4,5-tetrahydro-2-oxo-1H-benzazepin-3(R)-yl]amino]-3-t-butoxycarbonylamino-3-methylbutanamide Prepared from 4-bromomethyl-2'-(4-nitrophenoxy)-1,1'-biphenyl and 3-t-butoxycarbonylamino-3-methyl-N-[2,3,4,5-tetrahydro-2-oxo-1H-1-benzazepin-3(R)-yl]-butanamide (Example 1, Step I) by the procedure described in Example 1, Step Q. $^1$H NMR (200 MHz, CDCl$_3$): 1.32 (s,6H), 1.38 (s,9H), 1.78 (m,1H), 2.3–2.7 (m,5H), 4.47 (m,1H), 4.75 (d,15 Hz,1H), 5.13 (d,15 Hz,1H), 6.63 (d,7 Hz,1H), 6.75 (d,8 Hz,2H), 7.05–7.50 (m,11H), 7.97 (s,1H), 7.98 (d,8 Hz,2H).

Step D: N-[1-[[2'-(4-Aminophenoxy)[1,1'-biphenyl]-4-yl]methyl]-2,3,4,5-tetrahydro-2-oxo-1H-benzazepin-3(R)-yl]amino]-3-t-butoxycarbonylamino-3-methylbutanamide A solution of 282 mg (0.415 mmol) of the intermediate obtained in Step C in 30 mL of methanol was hydrogenated at 40 psi in the presence of 5% palladium on carbon. After uptake of hydrogen was complete, the mixture was filtered through Celite and the filtrate was evaporated under vacuum to yield 264 mg of product.

Step E: N-[1-[[2'-[4-[(Methylaminocarbonyl)amino]phenoxy][1,1'-biphenyl]-4-yl]methyl]-2,3,4,5-tetrahydro-2-oxo-1H-1-benzazepin-3(R)-yl]-3-t-butoxycarbonylamino-3-methylbutanamide A solution of 264 mg (0.40 mmol) of the intermediate obtained in Step D in 5 mL of methylene chloride under a nitrogen atmosphere was treated with 0.90 mL (15 mmol) of methyl isocyanate. The reaction mixture was stirred at room temperature for 18 hours, then all volatiles were removed under vacuum and the residue purified by chromatography on silica gel, eluting with ethyl acetate/hexane (3:1) to give 287 mg (0.40 mmol, 100%) of product. $^1$H NMR (400 MHz, CD$_3$OD): 1.24 (s,3H), 1.31 (s,6H), 1.39 (s,9H), 2.00 (m,1H), 2.30 (m,1H), 2.42 (m,3H), 2.50 (dd,1H), 2.73 (s,3H), 4.32 (dd,1H), 4.82 (d,1H), 5.24 (d,1H), 6.70 (m,2H), 6.95 (d,1H), 7.2 (m,13H).

Step F: N-[1-[[2'-[4-[(Methylaminocarbonyl)amino]phenoxy][1,1'-biphenyl]-4-yl]methyl]-2,3,4,5-tetrahydro-2-oxo-1H-1-benzazepin-3(R)-yl]-3-amino-3-methylbutanamide, trifluoroacetate A solution of 287 mg (0.40 mmol) of the intermediate obtained in Step E in 3 mL of methylene chloride was treated with 1.5 mL of trifluoroacetic acid. The reaction mixture was stirred at room temperature for 1 hour then evaporated under vacuum and the residue purified by reverse phase medium pressure liquid chromatography on C8, eluting with methanol/0.1% aqueous trifluoroacetic acid (50:50). Fractions containing the product were combined, solvents removed under vacuum and the residue lyophilized from water to give 165 mg (0.23 mmol, 57%) of the title compound as a white solid. FAB-MS: calculated for $C_{36}H_{39}N_5O_4$ 605; found 628 (M+Na). $^1$H NMR (400 MHz, CD$_3$OD): 1.33 (s,3H), 1.36 (s,3H), 2.06 (m,1H), 2.26 (m,1H), 2.48 (m,4H), 2.74 (s,3H), 4.36 (dd,1H), 4.8 (d,1H), 5.17 (d,1H).

EXAMPLE 28

N-[1-[[2'-[2-[(Methylaminocarbonyl)amino]phenoxy][1,1'-biphenyl]-4-yl]methyl]-2,3,4,5-tetrahydro-2-oxo-1H-1-benzazepin-3(R)-yl]-3-amino-3-methylbutanamide, trifluoroacetate

Step A: 4-Methyl-2'-(2-nitrophenoxy)-1,1'-biphenyl

Prepared from 4-methyl-2'-hydroxy-1,1'-biphenyl (Example 12, Step C) and 1-fluoro-2-nitrobenzene by the procedure described in Example 27, Step A. $^1$H NMR (200 MHz, CDCl$_3$): 2.30 (s,3H), 6.74 (dd;2,8 Hz;1H), 6.9–7.5 (m,10H), 7.84 (dd;2, 8 Hz;1H).

Step B: 4-Bromomethyl-2'-(2-nitrophenoxy)-1,1'-biphenyl

Prepared from 4-methyl-2'-(2-nitrophenoxy)-1,1'-biphenyl by the procedure described in Example 1, Step K. $^1$H NMR (400 MHz, CD$_3$OD): 4.52 (s,2H), 7.4 (m,11H), 7.86 (d,1H).

Step C: N-[1-[[2'-(2-Nitrophenoxy)[1,1'-biphenyl]-4-yl]methyl]-2,3,4,5-tetrahydro-2-oxo-1H-benzazepin-3(R)-yl]amino]-3-t-butoxycarbonylamino-3-methylbutanamide Prepared from 4-bromomethyl-2'-(2-nitrophenoxy)-1,1'-biphenyl and 3-t-butoxycarbonylamino-3-methyl-N-[2,3,4,5-tetrahydro-2-oxo-1H-1-benzazepin-3(R)-yl]butanamide (Example 1, Step I) by the procedure described in Example 1, Step Q. $^1$H NMR (200 MHz, CDCl$_3$): 1.32 (s,6H), 1.38 (s,9H), 1.78 (m,1H), 2.3–2.7 (m,5H), 4.47 (m,1H), 4.75 (d,15 Hz,1H), 5.13 (d,15 Hz,1H), 6.63 (d,7 Hz,1H), 6.75 (d,8 Hz,2H), 7.05–7.50 (m,/11H), 7.97 (s,1H), 7.98 (d,8 Hz,2H).

Step D: N-[1-[[2'-(2-Aminophenoxy)[1,1'-biphenyl]-4-yl]methyl]-2,3,4,5-tetrahydro-2-oxo-1H-benzazepin-3(R)-yl]amino]-3-t-butoxycarbonylamino-3-methylbutanamide Prepared from the intermediate obtained in Step C by the procedure described in Example 27, Step D.

Step E: N-[1-[[2'-[2-[(Methylaminocarbonyl)amino]phenoxy][1,1'-biphenyl]-4-yl]methyl]-2,3,4,5-tetrahydro-2-oxo-1H-1-benzazepin-3(R)-yl]-3-t-butoxycarbonylamino-3-methylbutanamide Prepared from the intermediate obtained in Step D by the procedure described in Example 27, Step E.

Step F: N-[1-[[2'-[2-[(Methylaminocarbonyl)amino]phenoxy][1,1'-biphenyl]-4-yl]methyl]-2,3,4,5-tetrahydro-2-oxo-1H-1-benzazepin-3(R)-yl]-3-amino-3-methylbutanamide, trifluoroacetate The title compound was prepared from the intermediate obtained in Step E by the procedure described in Example 27, Step F. FAB-MS: calculated for C$_{36}$H$_{39}$N$_5$O$_4$ 605; found 628 (M+Na). $^1$H NMR (400 MHz, CD$_3$OD): 1.38 (s, 3H), 1.42 (s, 3H), 2.08 (m, 1H), 2.38 (m, 3H), 2.54 (dd, 2H), 2.8 (s, 3H), 4.39 (dd, 1H), 4.85 (d, 1H), 5.3 (d, 1H), 6.51 (d, 1H), 5.8 dt, 1H), 6.84 (dt, 1H), 7.00 (dd, 1H), 7.34 (m, 12H), 8.94 (dd, 1H).

EXAMPLE 29

N-[1-[[2'-[(Methylaminocarbonyl)amino][1,1'-biphenyl]-4-yl]methyl]-2,3,4,5-tetrahydro-2-oxo-1H-1-benzazepin-3(R)-yl]-3-(2(R)-hydroxypropyl)amino-3-methylbutanamide, trifluoroacetate

Step A: N-[1-[[2'-[(Methylaminocarbonyl)amino][1,1'-biphenyl]-4-yl]methyl]-2,3,4,5-tetrahydro-2-oxo-1H-1-benzazepin-3(R)-yl]-3-(2(R)-benzyloxypropyl)amino-3-methylbutanamide, trifluoroacetate To a solution of 250 mg (0.399 mmol) of N-[1-[[2'-[(methylaminocarbonyl)amino][1,1'-biphenyl]-4-yl]methyl]-2,3,4,5-tetrahydro-2-oxo-1H-1-benzazepin-3(R)-yl]-3-amino-3-methylbutanamide, trifluoroacetate (Example 2) in 12 mL of methanol was added 1.35 g of powdered 4A molecular sieves followed by 713 mg (4.34 mmol) of (R)-2-benzyloxypropanal (prepared from ethyl-D-lactate according to the procedure of Hanessian and Kloss, Tetrahedron Lett. 1985, 26, 1261–1264.) in 2 mL of dry methanol. After adjusting the pH of the suspension to 5.5 with glacial acetic acid, the reaction mixture was stirred at room temperature for 3 hours. Dropwise, 2.5 mL of 1.0M sodium cyanoborohydride in tetrahydrofuran was added and the reaction mixture stirred at room temperature for 18 hours. The reaction mixture was filtered and the filtrate treated with 2.0 mL of trifluoroacetic acid (CAUTION! evolution of hydrogen cyanide). After stirring for 10 minutes, all volatiles were removed under vacuum and the residue chromatographed on silica gel, eluting with methylene chloride/methanol/concentrated ammonium hydroxide (90:5:1) to yield 225 mg (0.339 mmol, 85%) of product. FAB-MS with Li: calculated for C$_{40}$H$_{47}$N$_5$O$_4$ 661: found 668 (M+Li), 662 (M+1). $^1$H NMR (400 MHz, CD$_3$OD): 1.19 (d, 3H), 1.19 (s, 3H), 1.21 (s, 3H), 2.05 (m, 1H), 2.3 (m, 1H), 2.4 (m, 2H), 2.20 (s, 3H), 2.3 (m, 2H), 3.64 (m, 1H), 4.40 (dd, 1H), 4.58 (s, 1H), 4.62 (d, 1H), 5.05 (d, 1H), 5.14 (d, 1H), 7.23 (m, 16H), 7.66 (d, 1H).

Step B: N-[1-[[2'-[(Methylaminocarbonyl)amino]1,1'-biphenyl]-4-yl]methyl]-2,3,4,5-tetrahydro-2-oxo-1H-1-benzazepin-3(R)-yl]-3-(2(R)-hydroxypropyl)amino-3-methylbutanamide, trifluoroacetate A solution of 225 mg (0.339 mmol) of the intermediate obtained in Step A in 5 mL of methanol containing 0.2 mL of trifluoroacetic acid was hydrogenated at ambient temperature and 40 psi for 24 hours over 500 mg of 30% palladium on carbon. The reaction mixture was filtered through Celite and the filtrate was evaporated under vacuum and the residue purified by reverse phase medium pressure liquid chromatography on C8, eluting with methanol/0.1% aqueous trifluoroacetic acid (65:35). Fractions containing the product were combined, solvents removed under vacuum and the residue lyophilized from water to give 160 mg (0.23 mmol, 69%) of the title compound as a white solid. FAB-MS: calculated for C$_{33}$H$_{41}$N$_5$O$_4$ 571: found 572 (M+H). $^1$H NMR (400 MHz, CDCl$_3$): 1.20 (d, 1H), 1.36 (s, 3H), 1.37 (s, 3H), 2.15 (m, 1H), 2.34 (m, 1H), 2.34 (m, 1H), 2.62 (dd, 2H), 2.63 (s, 3H), 2.68 (m, 2H), 2.80 (dd, 1H), 3.09 (dd, 1H), 3.90 (m, 1H), 4.40 (dd, 1H), 5.08 (d, 1H), 5.16 (d, 1H), 7.22 (m, 11H), 7.62 (d, 1H).

EXAMPLE 30

N-[1-[[2'-[(Morpholinocarbonyl)amino][1,1'-biphenyl]-4-yl]methyl]-2,3,4,5-tetrahydro-2-oxo-1H-1-benzazepin-3(R)-yl]-3-(2(R)-hydroxypropyl)amino-3-methylbutanamide, trifluoroacetate Prepared from N-[1-[[2'-[(morpholinocarbony)amino][1,1'-biphenyl]-4-yl]methyl]-2,3,4,5-tetrahydro-2-oxo-1H-1-benzazepin-3(R)-yl]-3-amino-3-methylbutanamide, trifluoroacetate (Example 6) and (R)-2-benzyloxypropanal by the procedure described in Example 29. FAB-MS: calculated for $C_{36}H_{45}N_5O_5$ 627: found 650 (M+Na). $^1$H NMR (400 MHz, CDCl$_3$): 1.20 (d,3H), 1.36 (s,3H), 1.39 (s,3H), 2.14 (m,1H), 2.34 (m,1H), 2.62 (dd,2H), 2.66 (m,2H), 2.7 (dd,1H), 3.09 (dd,1H), 3.25 (m,4H), 3.63 (m,4H), 3.83 (m,1H), 4.39 (m,1H), 5.05 (d,1H), 5.20 (d,1H), 7.29 (m,12H).

EXAMPLE 31

N-[1-[[2'-[[(2-Hydroxyethylamino)carbonyl]amino][1,1'-biphenyl]-4-yl]methyl]-2,3,4,5-tetrahydro-2-oxo-1H-1-benzazepin-3(R)-yl]-3-(2(R)-hydroxypropyl)amino-3-methylbutanamide, trifluoroacetate Prepared from N-[1-[[2'-[[(2-hydroxyethylamino)carbonyl]amino][1,1'-biphenyl]-4-yl]methyl]-2,3,4,5-tetrahydro-2-oxo-1H-1-benzazepin-3(R)-yl]-3-amino-3-methylbutanamide, trifluoroacetate (Example 8) and (R)-2-benzyloxypropanal by the procedure described in Example 29. FAB-MS: calculated for $C_{34}H_{43}N_5O_5$ 601: found 602 (M+1). $^1$H NMR (400 MHz, CD$_3$OD): 1.20 (d,3H), 1.36 (s,3H), 1.38 (s,3H), 2.18 (m,1H), 2.35 (m,1H), 2.62 (dd,2H), 2.68 (m,2H), 2.78 (dd,1H), 3.09 (dd,1H), 3.2 (t,2H), 3.52 (t,2H), 3.93 (m,1H), 4.40 (dd,1H), 5.12 (d,1H), 5.18 (d,1H), 7.28 (m,11H), 7.65 (d,1H).

EXAMPLE 32

N-[1-[[2'-[(Methylaminocarbonyl)amino][1,1'-biphenyl]-4-yl]methyl]-2,3,4,5-tetrahydro-2-oxo-1H-1-benzazepin-3(R)-yl]-3-[2(S),3-dihydroxypropyl]amino-3-methylbutanamide, trifluoroacetate To a stirred solution of 368 mg (0.716 mmol) of N-[1-[[2'-[(methylaminocarbonyl)amino][1,1'-biphenyl]-4-yl]methyl]-2,3,4,5-tetrahydro-2-oxo-1H-1-benzazepin-3(R)-yl]-3-amino-3-methylbutanamide, trifluoroacetate (Example 2) in 12 mL of dry methanol under nitrogen was added 1.35 g of powdered 4A molecular sieves followed by a solution of 0.4 g of D-glyceraldehyde acetonide (used crude as prepared according to the procedure of Hertel, L. W.; Grossman, C. S.; Kroin, J. S. Synth. Comm. 1991, 21, 151–154.) in 1 mL of dry methanol. The pH of the mixture was carefully adjusted to 5.5 with glacial acetic acid and triethylamine. The reaction was stirred at room temperature for 2 hours at which time 3.0 mL of a 1.0M solution of sodium cyanoborohydride in tetrahydrofuran was added dropwise by syringe. The reaction mixture was stirred at room temperature for 18 hours, then filtered and the filtrate treated with 9 mL of trifluoroacetic acid and 9 mL of water. After 1 hour, the reaction mixture was evaporated under vacuum and the residue purified by reverse phase medium pressure liquid chromatography on C8, eluting with methanol/0.1% aqueous trifluoroacetic acid (60:40). Fractions containing the product were combined, solvents removed under vacuum and the residue lyophilized from water to give 167 mg of the title compound as a white solid. FAB-MS: calculated for $C_{33}H_{41}N_5O_5$ 587: found 589. $^1$H NMR (400 MHz, CD$_3$OD): 1.37 (s,3H), 1.39 (s,3H), 2.15 (m,1H), 2.35 (m,1H), 2.55–2.75 (m,4H), 2.64 (s,3H), 2.95 (dd,1H), 3.18 (dd,1H), 3.54 (m,2H), 3.83 (m,1H), 4.42 (dd,1H), 5.08 (d,1H), 5.16 (d,1H), 7.1–7.4 (m,11H), 7.61 (d,1H).

EXAMPLE 33

N-[1-[[2'-[(Aminocarbonyl)amino][1,1'-biphenyl]-4-yl]methyl]-2,3,4,5-tetrahydro-2-oxo-1H-1-benzazepin-3(R)-yl]-3-[2(S),3-dihydroxypropyl]amino-3-methylbutanamide, trifluoroacetate The title compound was prepared from N-[1-[[2'-[(aminocarbonyl)amino][1,1'-biphenyl]-4-yl]methyl]-2,3,4,5-tetrahydro-2-oxo-1H-1-benzazepin-3(R)-yl]-3-amino-3-methylbutanamide, trifluoroacetate (Example 5) and D-glyceraldehyde acetonide according to the procedure described in Example 32. FAB-MS: calculated for $C_{32}H_{41}N_5O_4$ 559: found 561. $^1$H NMR (400 MHz, CD$_3$OD): 1.36 (s, 1H), 1.38 (s, 3H), 2.15 (m, 1H), 2.34 (m, 1H), 2.62 (dd, 2H), 2.68 (m, 2H), 2.95 (dd, 1H), 3.18 (dd, 1H), 3.52 (m, 2H), 3.82 (m, 1H), 4.40 (dd, 1H), 5.05 (d, 1H), 5.06 (d, 1H), 7.52 (m, 11H), 7.60 (d, 1H).

EXAMPLE 34

N-[1-[[2'-[[(2-Hydroxyethylamino)carbonyl]amino][1,1'-biphenyl]-4-yl]methyl]-2,3,4,5-tetrahydro-2-oxo-1H-1-benzazepin-3(R)-yl]-3-[2(S), 3-dihydroxypropyl]amino-3-methylbutanamide, trifluoroacetate The title compound was prepared from N-[1-[[2'-[[(2-hydroxyethylamino)carbonyl]amino][1,1'-biphenyl]-4-yl]methyl]-2,3,4,5-tetrahydro-2-oxo-1H-1-benzazepin-3(R)-yl]-3-amino-3-methylbutanamide, trifluoroacetate (Example 8) and D-glyceraldehyde acetonide according to the procedure described in Example 32.

EXAMPLE 35

Utilizing the procedures described in Examples 1 to 34 and general methods of organic synthesis described in the chemical literature and familiar to one skilled in the art, the following compounds of Formula 1 can be prepared from the appropriately substituted starting materials and reagents.

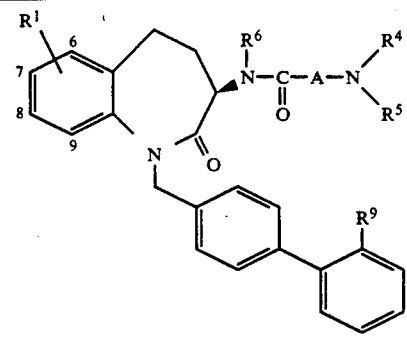

| R¹ | R⁹ | A | R⁴ | R⁵ | R⁶ |
|---|---|---|---|---|---|
| H | -NH-C(=O)-NHCH₃ | -CH₂-C(CH₃)₂- | -CH₂-CH(OH)-CH(OH)-CH₂OH | H | H |
| H | -NH-C(=O)-NHCH₃ | -CH₂-C(CH₃)₂- | -CH₂CH₂OH | H | H |
| H | -NH-C(=O)-NHCH₃ | -CH₂-C(CH₃)₂- | -CH₂C(OH)(CH₃)₂ | H | H |
| H | -NH-C(=O)-NHCH₃ | -CH₂-C(CH₃)₂- | -CH₂CH(OH)CH₃ | H | H |
| H | -NH-C(=O)-NHCH₃ | -CH₂-C(CH₃)₂- | -CH₂-C₆H₅ | H | H |
| H | -NH-C(=O)-NHCH₃ | -CH₂-C(CH₃)₂- | -CH₂CH₂CH₃ | H | H |
| H | -NH-C(=O)-NHCH₃ | -CH₂-C(CH₃)₂- | -CH₂CH(OH)CH₃ | H | CH₃ |
| 6-F | -NH-C(=O)-NHCH₃ | -CH₂-C(CH₃)₂- | H | H | H |
| 7-F | -NH-C(=O)-NHCH₃ | -CH₂-C(CH₃)₂- | H | H | H |
| 7-CF₃ | -NH-C(=O)-NHCH₃ | -CH₂-C(CH₃)₂- | H | H | H |
| 7-OCH₃ | -NH-C(=O)-NHCH₃ | -CH₂-C(CH₃)₂- | H | H | H |
| 7-OH | -NH-C(=O)-NHCH₃ | -CH₂-C(CH₃)₂- | H | H | H |
| 7-SCH₃ | -NH-C(=O)-NHCH₃ | -CH₂-C(CH₃)₂- | H | H | H |
| 7-S(O)CH₃ | -NH-C(=O)-NHCH₃ | -CH₂-C(CH₃)₂- | H | H | H |
| 8-OCH₃ | -NH-C(=O)-NHCH₃ | -CH₂-C(CH₃)₂- | H | H | H |
| 8-F | -NH-C(=O)-NHCH₃ | -CH₂-C(CH₃)₂- | H | H | H |

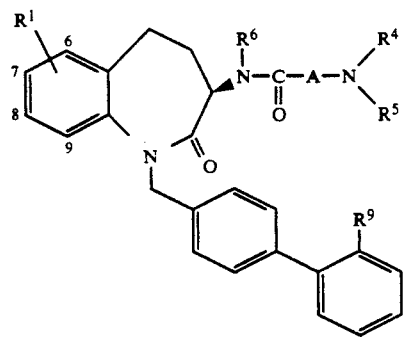

| R¹ | R⁹ | A | R⁴ | R⁵ | R⁶ |
|---|---|---|---|---|---|
| 8-Cl | −NH−C(=O)−NHCH₃ | −CH₂−C(CH₃)(CH₃)− | H | H | H |
| 8-I | −NH−C(=O)−NHCH₃ | −CH₂−C(CH₃)(CH₃)− | H | H | H |
| H | −NH−C(=O)−NHCH₃ | −C(CH₃)(CH₃)− | H | H | H |
| H | −NH−C(=O)−NHCH₃ | −C(H)(CH₃)− | H | H | H |
| H | −NH−C(=O)−NHCH₃ | −C(CH₃)(H)− | H | H | H |
| H | −NH−C(=O)−NHCH₃ | −C(H)(CH₂OH)− | H | H | H |
| H | −NH−C(=O)−NHCH₃ | −C(CH₃)(CH₂OH)− | H | H | H |
| H | −NH−C(=O)−NHCH₃ | −C(H)(CH₃)− | CH₃ | H | H |
| H | −NH−C(=O)−NHCH₃ | −CH₂−C(CH₃)(CH₂OH)− | H | H | H |
| H | −NH−C(=O)−NHCH₃ | −CH₂−C(HOCH₂)(CH₃)− | H | H | H |
| H | −NH−C(=O)−NHCH₃ | −CH₂−C(HOCH₂)(CH₃)− | −CH₂CH(OH)CH₃ | H | H |
| H | −NH−C(=O)−NHCH₃ | −CH₂−C(HOCH₂)(CH₃)− | −CH₂CH(OH)CH₂OH | H | H |
| H | −NH−C(=O)−NHCH₃ | −C(H)(CH₂−C₆H₅)− | H | H | H |
| H | −NH−C(=O)−NHCH₃ | −C(H)(CH₂-indolyl)− | H | H | H |

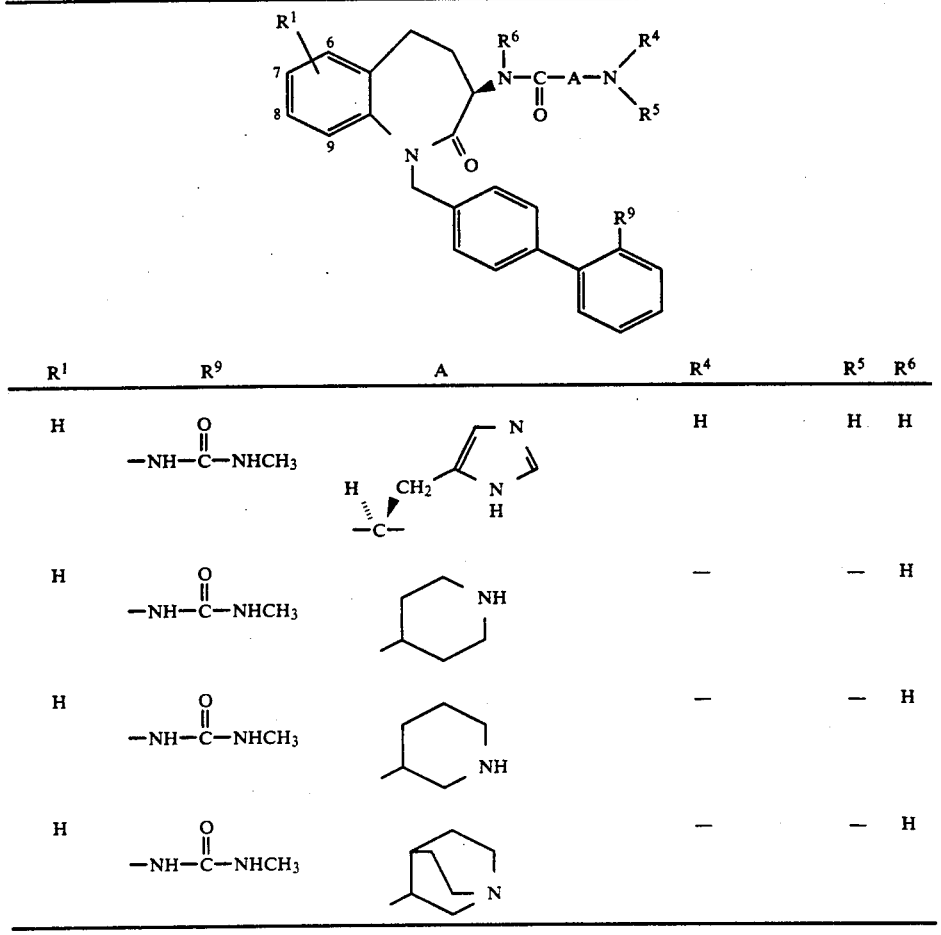
EXAMPLE 36
Utilizing the procedures described in Examples 1 to 34 and general methods of organic synthesis described in the chemical literature and familiar to one skilled in the art, the following compounds of Formula I can be prepared from the appropriately substituted starting materials and reagents.
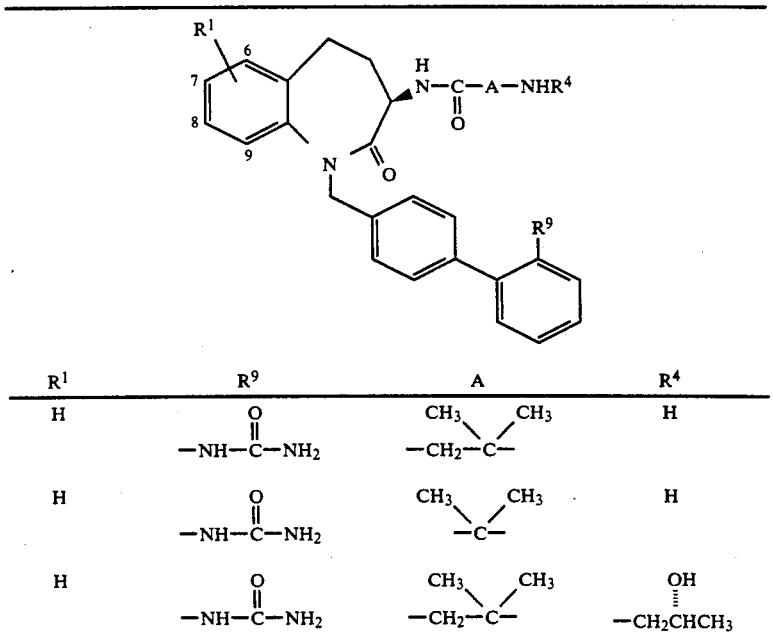

-continued

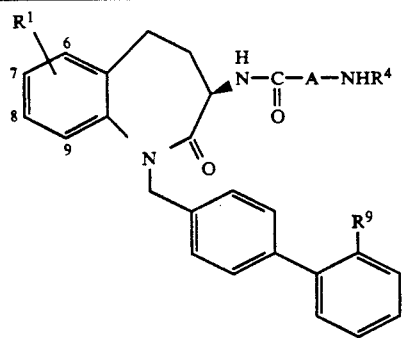

| R¹ | R⁹ | A | R⁴ |
|---|---|---|---|
| H | −NH−C(=O)−NHCH₃ | −CH₂−C(CH₃)(CH₃)− | −CH₂CHCH₃ with OH |
| H | −NH−C(=O)−NHCH₂CH₂OH | −CH₂−C(CH₃)(CH₃)− | −CH₂CH₂CHCH₃ with OH |
| H | −NH−C(=O)−NHCH₃ | −CH₂−C(CH₃)(CH₃)− | −CH₂CHCH₂OH with OH |
| H | −NH−C(=O)−NHCH₃ | −CH₂−C(CH₃)(CH₃)− | −CH₂CHCH₃ with F |
| 7-F | −NH−C(=O)−NHCH₃ | −CH₂−C(CH₃)(CH₃)− | −CH₂CHCH₃ with OH |
| 7-CF₃ | −NH−C(=O)NHCH₃ | −CH₂−C(CH₃)(CH₃)− | −CH₂CHCH₃ with OH |
| 7-OCH₃ | −NH−C(=O)−NHCH₃ | −CH₂−C(CH₃)(CH₃)− | −CH₂CHCH₃ with OH |
| 7-SCH₃ | −NH−C(=O)−NHCH₃ | −CH₂−C(CH₃)(CH₃)− | −CH₂CHCH₃ with OH |
| 7-F | −NH−C(=O)−NHCH₃ | −C(H)(CH₃)− | H |
| 7-F | −NH−C(=O)−NHCH₃ | −C(H)(CH₂OH)− | H |
| 7-F | −NH−C(=O)−NHCH₃ | −C(CH₃)(CH₂OH)− | H |
| 7-F | −NH−C(=O)−NHCH₃ | −CH₂−C(HOCH₂)(CH₃)− | H |
| 7-F | −NH−C(=O)−NHCH₃ | −CH₂−C(HOCH₂)(CH₃)− | −CH₂CHCH₃ with OH |
| 7-CF₃ | −NH−C(=O)−NHCH₃ | −CH₂−C(HOCH₂)(CH₃)− | −CH₂CHCH₂OH with OH |
| 6-F | −NH−C(=O)−NHCH₃ | −CH₂−C(HOCH₂)(CH₃)− | −CH₂CH₂CHCH₃ with OH |

EXAMPLE 37

Utilizing the procedures described in Examples 1 to 34 and general methods of organic synthesis described in the chemical literature and familiar to one skilled in the art, the following compounds of Formula I can be prepared from the appropriately substituted starting materials and reagents.

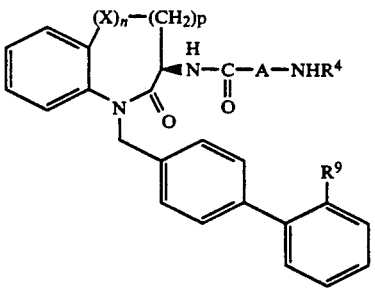

| X | n | p | R$^9$ | A | R$^4$ |
|---|---|---|---|---|---|
| — | 0 | 3 | —NH—C(=O)—NHCH$_3$ | —CH$_2$—C(CH$_3$)(CH$_3$)— | H |
| — | 0 | 3 | —NH—C(=O)—NHCH$_3$ | —CH$_2$—C(CH$_3$)(CH$_3$)— | OH, —CH$_2$CHCH$_3$ |
| — | 0 | 1 | —NH—C(=O)—NHCH$_3$ | —CH$_2$—C(CH$_3$)(CH$_3$)— | H |
| — | 0 | 1 | —NH—C(=O)—NHCH$_3$ | —CH$_2$—C(CH$_3$)(CH$_3$)— | OH, —CH$_2$CHCH$_3$ |
| — | 0 | 0 | —NH—C(=O)—NHCH$_3$ | —CH$_2$—C(CH$_3$)(CH$_3$)— | H |
| — | 0 | 0 | —NH—C(=O)—NHCH$_3$ | —CH$_2$—C(CH$_3$)(CH$_3$)— | OH, —CH$_2$CHCH$_3$ |
| C=O | 1 | 1 | —NH—C(=O)—NHCH$_3$ | —CH$_2$—C(CH$_3$)(CH$_3$)— | OH, —CH$_2$CHCH$_3$ |
| CHOH | 1 | 1 | —NH—C(=O)—NHCH$_3$ | —CH$_2$—C(CH$_3$)(CH$_3$)— | OH, —CH$_2$CHCH$_3$ |
| S | 1 | 0 | —NH—C(=O)—NHCH$_3$ | —CH$_2$—C(CH$_3$)(CH$_3$)— | H |
| S | 1 | 0 | —NH—C(=O)—NHCH$_3$ | —C(CH$_3$)(CH$_3$)— | H |
| S | 1 | 0 | —NH—C(=O)—NHCH$_3$ | —CH$_2$—C(CH$_3$)(CH$_3$)— | OH, —CH$_2$CHCH$_3$ |
| SO | 1 | 0 | —NH—C(=O)—NHCH$_3$ | —CH$_2$—C(CH$_3$)(CH$_3$)— | H |
| SO | 1 | 0 | —NH—C(=O)—NHCH$_3$ | —C(CH$_3$)(CH$_3$)— | H |
| SO | 1 | 0 | —NH—C(=O)—NHCH$_3$ | —CH$_2$—C(CH$_3$)(CH$_3$)— | OH, —CH$_2$CHCH$_3$ |
| S | 1 | 2 | —NH—C(=O)—NHCH$_3$ | —CH$_2$—C(CH$_3$)(CH$_3$)— | H |

-continued

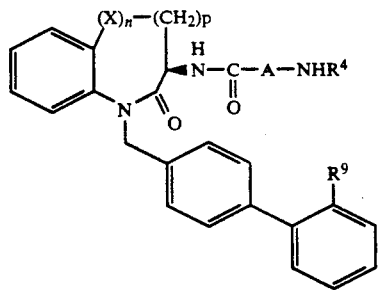

| X | n | p | R⁹ | A | R⁴ |
|---|---|---|---|---|---|
| S | 1 | 2 | -NH-C(O)-NHCH₃ | -C(CH₃)₂- | H |
| S | 1 | 2 | -NH-C(O)-NHCH₃ | -CH₂-C(CH₃)₂- | -CH₂CH(OH)CH₃ |
| S | 1 | 2 | -NH-C(O)-NHCH₃ | -CH-C(CH₃)₂- | H |
| S | 1 | 2 | -NH-C(O)-NHCH₃ | -C(CH₃)₂- | H |
| S | 1 | 2 | -NH-C(O)-NHCH₃ | -CH₂-C(CH₃)₂- | -CH₂CH(OH)CH₃ |
| O | 1 | 1 | -NH-C(O)-NHCH₃ | -CH₂-C(CH₃)₂- | H |
| O | 1 | 1 | -NH-C(O)-NHCH₃ | -C(CH₃)₂- | H |
| O | 1 | 1 | -NH-C(O)-NHCH₃ | -CH₂-C(CH₃)₂- | -CH₂CH(OH)CH₃ |

EXAMPLE 38

Utilizing the procedures described in Examples 1 to 34 and general methods of organic synthesis described in the chemical literature and familiar to one skilled in the art, the following compounds of Formula I can be prepared from the appropriately substituted starting materials and reagents.

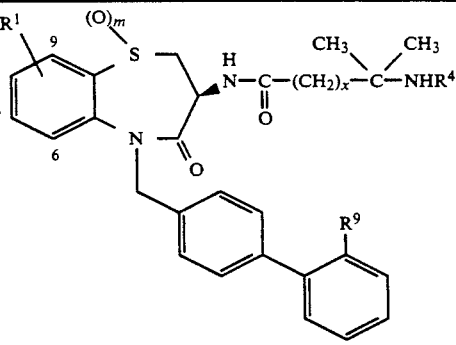

| R¹ | x | m | R⁹ | R⁴ |
|---|---|---|---|---|
| H | 1 | 0 | -NH-C(O)-NHCH₃ | -CH₂CH(OH)CH₃ |
| H | 1 | 0 | -NH-C(O)-NHCH₃ | -CH₂CH(OH)CH₃ |

-continued

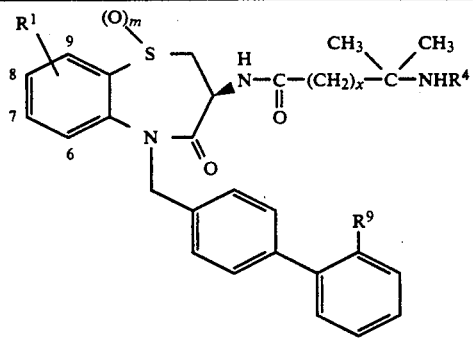

| R¹ | x | m | R⁹ | R⁴ |
|---|---|---|---|---|
| H | 1 | 0 | —NH—C(=O)—NHCH₃ | —CH₂CH(OH)CH₂OH |
| H | 0 | 0 | —NH—C(=O)—NHCH₃ | H |
| H | 0 | 0 | —NH—C(=O)—NHCH₃ | —CH₂CH₂CH(OH)CH₃ |
| H | 1 | 1 | —NH—C(=O)—NHCH₃ | —CH₂CH(OH)CH₃ |
| H | 1 | 1 | —NH—C(=O)—NHCH₃ | —CH₂CH(OH)CH₂OH |
| H | 1 | 1 | —NH—C(=O)—NHCH₃ | —CH₂CH(OH)CH₃ |
| H | 1 | 1 | —NH—C(=O)—NHCH₃ | —CH₂CH₂CH(OH)CH₃ |
| H | 1 | 0 | —NH—C(=O)—NHCH₃ | —CH₂CH(OCH₃)CH₃ |
| 8-F | 1 | 0 | —NH—C(=O)—NHCH₃ | —CH₂CH(OH)CH₃ |
| 8-CF₃ | 1 | 0 | —NH—C(=O)—NHCH₃ | —CH₂CH(OH)CH₃ |
| 8-OCH₃ | 1 | 0 | —NH—C(=O)—NHCH₃ | —CH₂CH(OH)CH₃ |
| 8-SCH₃ | 1 | 0 | —NH—C(=O)—NHCH₃ | —CH₂CH(OH)CH₃ |
| 9-F | 1 | 0 | —NH—C(=O)—NHCH₃ | —CH₂CH(OH)CH₃ |
| 8-F | 1 | 0 | —NH—C(=O)—NHCH₃ | —CH₂C(OH)(CH₃)₂ |
| 8-F | 1 | 0 | —NH—C(=O)—NHCH₃ | —CH₂CH(OH)CH(OH)CH₂OH |

-continued

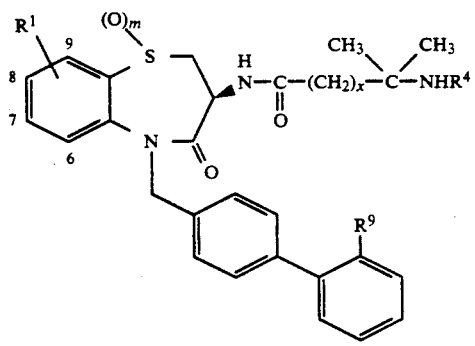

| R¹ | x | m | R⁹ | R⁴ |
|---|---|---|---|---|
| H | 1 | 0 | —NH—C(=O)—NHCH₂CH₂OH | H |
| H | 1 | 0 | —NH—C(=O)—NHCH₂CH₂OH | —CH₂CH(OH)CH₃ |
| H | 1 | 1 | —NH—C(=O)—NHCH₂CH₂OH | —CH₂CH(OH)CH₃ |
| H | 1 | 0 | —NH—C(=O)—NHCH₂CH₂OH | —CH₂CH(OH)CH₂OH |
| H | 1 | 0 | —NH—C(=O)—NHCH₂CH₂OH | —CH₂CH₂CH(OH)CH₃ |
| H | 0 | 0 | —NH—C(=O)—NHCH₂CH₂OH | —CH₂CH₂CH(OH)CH₃ |
| H | 1 | 0 | —NH—C(=O)—NHCH₂CH₂OH | —CH₂—CH(OH)—CH(OH)—CH₂OH |
| 8-F | 1 | 0 | —NH—C(=O)—NHCH₂CH₂OH | —CH₂CH(OH)CH₃ |
| 8-CF₃ | 1 | 0 | —NH—C(=O)—NHCH₂CH₂OH | —CH₂CH(OH)CH₃ |
| 8-OCH₃ | 1 | 0 | —NH—C(=O)—NHCH₂CH₂OH | —CH₂CH(OH)CH₃ |
| 8-F | 1 | 1 | —NH—C(=O)—NHCH₂CH₂OH | —CH₂CH(OH)CH₃ |

What is claimed is:
1. A compound having the formula:

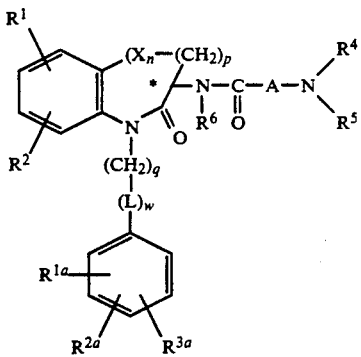

where
L is

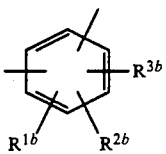

n is 0 or 1;
p is 0 to 3;
q is 0 to 4;
w is 0 or 1;
X is C=O or

m is 0 to 2;
$R^1$, $R^2$, $R^{1a}$, $R^{2a}$, $R^{1b}$, and $R^{2b}$ are independently hydrogen, halogen, $C_1$-$C_7$ alkyl, $C_1$-$C_3$ perfluoroalkyl, $C_1$-$C_3$ perfluoroalkoxy, —S(O)$_m$R$^{7a}$, cyano, nitro, R$^{7b}$O(CH$_2$)$_v$—, R$^{7b}$COO(CH$_2$)$_v$—, R$^{7b}$OCO(CH$_2$)$_v$—, R$^4$R$^5$N(CH$_2$)$_v$—, R$^{7b}$CON(R$^4$)(CH$_2$)$_v$—, R$^4$R$^5$NCO(CH$_2$)$_v$—, phenyl or substituted phenyl where the substituents are from 1 to 3 of halogen, $C_1$-$C_6$ alkyl, $C_1$-$C_6$ alkoxy, or hydroxy;
$R^{7a}$ and $R^{7b}$ are independently hydrogen, $C_1$-$C_3$ perfluoroalkyl, $C_1$-$C_6$ alkyl, substituted $C_1$-$C_6$ alkyl, where the substituents are phenyl or substituted phenyl; phenyl or substituted phenyl where the phenyl substituents are from 1 to 3 of halogen, $C_1$-$C_6$ alkyl, $C_1$-$C_6$ alkoxy, or hydroxy and v is 0 to 3;
$R^{3a}$ and $R^{3b}$ are independently hydrogen, $R^9$, $C_1$-$C_6$ alkyl substituted with $R^9$, phenyl substituted with $R^9$, or phenoxy substituted with $R^9$ with the proviso that either $R^{3a}$ or $R^{3b}$ must be a substituent other than hydrogen;
$R^9$ is:
R$^{4b}$R$^{12a}$NCON(R$^{12b}$)(CH$_2$)$_v$—,
R$^{4b}$R$^{12a}$NCSN(R$^{12b}$)(CH$_2$)$_v$—,
R$^{4b}$R$^{12a}$NN(R$^{12b}$)CSN(R$^{12c}$)(CH$_2$)$_v$—,
R$^{4b}$R$^{12a}$NN(R$^{12b}$)CON(R$^{12c}$)(CH$_2$)$_v$—,
R$^{4b}$R$^{12a}$NN(R$^{12b}$)COO(CH$_2$)$_v$—, R$^{4b}$R$^{12a}$NCOO(CH$_2$)$_v$— or R$^{13}$OCON(R$^{12b}$)(CH$_2$)$_v$—,
where v is 0 to 3;
$R^{12a}$, $R^{12b}$ and $R^{12c}$ are independently R$^{5a}$, OR$^{5a}$ or COR$^{5a}$, R$^{12a}$ and R$^{12b}$, or R$^{12b}$ and R$^{12c}$, or R$^{13}$ and R$^{12b}$, or R$^{12a}$ and R$^{4b}$ can be taken together to form —(CH$_2$)$_r$—B—(CH$_2$)$_s$— where B is CHR$^1$, O, S(O)$_m$ or NR$^{10}$, m is 0, 1 or 2, r and s are independently 0 to 3 and R$^1$ and R$^{10}$ are as defined;
$R^{13}$ is: $C_1$-$C_3$ perfluoroalkyl, $C_1$-$C_6$ alkyl, substituted $C_1$-$C_6$ alkyl, where the substitutents are hydroxy, NR$^{10}$R$^{11}$, carboxy, phenyl or substituted phenyl; phenyl or substituted phenyl where the substituents on the phenyl are from 1 to 3 of halogen, $C_1$-$C_6$ alkyl, $C_1$-$C_6$ alkoxy or hydroxy;
and v is as defined above;
$R^4$, $R^{4b}$, $R^5$ and $R^{5a}$ are independently hydrogen, phenyl, substituted phenyl, $C_1$-$C_{10}$ alkyl, substituted $C_1$-$C_{10}$ alkyl, $C_3$-$C_{10}$ alkenyl, substituted $C_3$-$C_{10}$ alkenyl, $C_3$-$C_{10}$ alkynyl, or substituted $C_3$-$C_{10}$ alkynyl where the substituents on the phenyl, alkyl, alkenyl or alkynyl are from 1 to 5 of hydroxy, $C_1$-$C_6$ alkoxy, $C_3$-$C_7$ cycloalkyl, fluoro, $R^1$ substituted or $R^1$, $R^2$ independently disubstituted phenyl $C_1$-$C_3$ alkoxy, $R^1$ substituted or $R^1$, $R^2$ independently disubstituted phenyl, $C_1$-$C_{20}$-alkanoyloxy, $C_1$-$C_5$ alkoxycarbonyl, carboxy, formyl, or —NR$^{10}$R$^{11}$ where R$^{10}$ and R$^{11}$ are independently hydrogen, $C_1$-$C_6$ alkyl, phenyl $C_1$-$C_6$ alkyl, $C_1$-$C_5$-alkoxycarbonyl or $C_1$-$C_5$-alkanoyl-$C_1$-$C_6$ alkyl; or
$R^4$ and $R^5$ can be taken together to form —(CH$_2$)$_r$B(CH$_2$)$_s$— where B is CHR$^1$, O, S(O)$_m$ or N—R$^{10}$, r and s are independently 1 to 3, and R$^1$ and R$^{10}$ are as defined above;
$R^6$ is hydrogen, $C_1$-$C_{10}$ alkyl, phenyl or phenyl $C_1$-$C_{10}$ alkyl;
A is

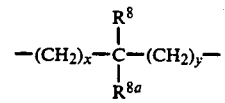

where x and y are independently 0-3;
$R^8$ and $R^{8a}$ are independently hydrogen, $C_1$-$C_{10}$ alkyl, trifluoromethyl, phenyl, substituted $C_1$-$C_{10}$ alkyl where the substituents are from 1 to 3 of imidazolyl, indolyl, hydroxy, fluoro, S(O)$_m$R$^{7a}$, $C_1$-$C_6$ alkoxy, $C_3$-$C_7$ cycloalkyl, $R^1$ substituted or $R^1$, $R^2$ independently disubstituted phenyl $C_1$-$C_3$ alkoxy, $R^1$ substituted or $R^1$, $R^2$ independently disubstituted phenyl, $C_1$-$C_5$-alkanoyloxy, $C_1$-$C_5$ alkoxycarbonyl, carboxy, formyl, or —NR$^{10}$R$^{11}$ where R$^{10}$ and R$^{11}$ are as defined above; or
$R^8$ and $R^{8a}$ can be taken together to form —(CH$_2$)$_t$— where t is 2 to 6; and $R^8$ and $R^{8a}$ can independently be joined to one or both of $R^4$ and $R^5$ to form alkylene bridges between the terminal nitrogen and the alkyl portion of the A group wherein the bridge contains from 1 to 5 carbon atoms;
and pharmaceutically acceptable salts thereof.
2. A compound of Claim 1 wherein:
n is 0;
p is 0 to 3;
q is 0 to 2;
w is 0 or 1;
m is 0 to 2;
$R^1$, $R^2$, $R^{1a}$, $R^{2a}$, $R^{1b}$, and $R^{2b}$ are independently hydrogen, halogen, $C_1$-$C_7$ alkyl, $C_1$-$C_3$ perfluoroalkyl, —S(O)$_m$R$^{7a}$, R$^{7b}$O(CH$_2$)$_v$—, R$^{7b}$COO(CH$_2$)$_v$—, R$^{7b}$OCO(CH$_2$)$_v$—, phenyl or substituted phenyl where the substituents are from 1 to 3 of halogen, $C_1$-$C_6$ alkyl, $C_1$-$C_6$ alkoxy, or hydroxy;

$R^{7a}$ and $R^{7b}$ are independently hydrogen, $C_1$-$C_3$ perfluoroalkyl, $C_1$-$C_6$ alkyl, substituted $C_1$-$C_6$ alkyl, where the substituents are phenyl; and v is 0 to 2;

$R^{3a}$ and $R^{3b}$ are independently hydrogen, $R^9$, $C_1$-$C_6$ alkyl substituted with $R^9$, phenyl substituted with $R^9$, or phenoxy substituted with $R^9$ with the proviso that either $R^{3a}$ or $R^{3b}$ must be a substituent other than hydrogen;

$R^9$ is:
$R^{4b}R^{12a}NCON(R^{12b})(CH_2)_v$—,
$R^{4b}R^{12a}NCSN(R^{12b})(CH_2)_v$—,
$R^{4b}R^{12a}NN(R^{12b})CON(R^{12c})(CH_2)_v$—,
$R^{4b}R^{12a}NN(R^{12b})COO(CH_2)_v$—,
$R^{4b}R^{12a}NCOO(CH_2)_v$—, or $R^{13}O$-$CON(R^{12b})(CH_2)_v$—,
where v is 0 to 3.

$R^{12a}$, $R^{12b}$ and $R^{12c}$ are independently $R^{5a}$, $OR^{5a}$ or $COR^{5a}$; $R^{12a}$ and $R^{12b}$, or $R^{12b}$ and $R^{12c}$, or $R^{13}$ and $R^{12b}$ or $R^{12a}$ and $R^{4b}$ can be taken together to form —$(CH_2)_r$—B—$(CH_2)_s$— where B is $CHR^1$, O, $S(O)_m$ or $NR^{10}$, m is 0, 1 or 2, r and s are independently 0 to 3, $R^1$ is as defined above and $R^{10}$ is hydrogen, $C_1$-$C_6$ alkyl, phenyl $C_1$-$C_6$ alkyl or $C_1$-$C_5$ alkanoyl-$C_1$-$C_6$ alkyl;

$R^{13}$ is: $C_1$-$C_3$ perfluoroalkyl, $C_1$-$C_6$ alkyl, substituted $C_1$-$C_6$ alkyl, where the substituents are hydroxy, $NR^{10}R^{11}$, carboxy, phenyl or substituted phenyl; phenyl or substituted phenyl where the substituents on the phenyl are from 1 to 3 of halogen, $C_1$-$C_6$ alkyl, $C_1$-$C_6$ alkoxy or hydroxy;
where v is as defined above;

$R^4$, $R^{4b}$, $R^5$ and $R^{5a}$ are independently hydrogen, Phenyl substituted phenyl, C1-C10 alkyl substituted C1-C10 alkyl, where the substiuents on the alkyl or phenyl are from 1 to 5 of hydroxy, $C_1$-$C_6$ alkoxy, $C_3$-$C_7$ cycloalkyl, fluoro, $R^1$ substituted or $R^1$, $R^2$ independently disubstituted phenyl $C_1$-$C_3$ alkoxy, $R^1$ substituted or $R^1$, $R^2$ independently disubstituted phenyl, $C_1$-$C_{20}$-alkanoyloxy, $C_1$-$C_5$ alkoxycarbonyl, carboxy or formyl;

$R^4$ and $R^5$ can be taken together to form —$(CH_2)_r$B$(CH_2)_s$— where B is $CHR^1$, O, $S(O)_m$ or N—$R^{10}$, r and s are independently 1 to 3 and $R^1$ and $R^{10}$ are as defined above;

$R^6$ is hydrogen, $C_1$-$C_{10}$ alkyl or phenyl $C_1$-$C_{10}$ alkyl;
A is

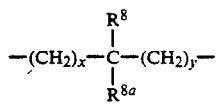

where x and y are independently 0-2;

$R^8$ and $R^{8a}$ are independently hydrogen, $C_1$-$C_{10}$ alkyl, substituted $C_1$-$C_{10}$ alkyl where the substituents are from 1 to 3 of imidazolyl, indolyl, hydroxy, fluoro, $S(O)_mR^{7a}$, $C_1$-$C_6$ alkoxy, $R^1$ substituted or $R^1$, $R^2$ independently disubstituted phenyl, $C_1$-$C_5$-alkanoyloxy, $C_1$-$C_5$ alkoxycarbonyl, carboxy, formyl, —$NR^{10}R^{11}$ where $R^{10}$ and $R^{11}$ are independently hydrogen, $C_1$-$C_6$ alkyl, or $C_1$-$C_5$ alkanoyl-$C_1$-$C_6$ alkyl; or $R^8$ and $R^{8a}$ can be taken together to form —$(CH_2)_t$— where t is 2 to 4; and $R^8$ and $R^{8a}$ can independently be joined to one or both of $R^4$ and $R^5$ to form alkylene bridges between the terminal nitrogen and the alkyl portion of the A group wherein the bridge contains from 1 to 5 carbon atoms; and pharmaceutically acceptable salts thereof.

3. A compound of Claim 2 wherein:
n is 0;
p is 0 to 2;
q is 0 to 2;
w is 0 or 1;
m is 0 or 1;
$R^1$, $R^2$, $R^{1a}$, $R^{2a}$, $R^{1b}$, and $R^{2b}$ are independently hydrogen, halogen, $C_1$-$C_7$ alkyl, $C_1$-$C_3$ perfluoroalkyl, —$S(O)_mR^{7a}$, $R^{7b}O(CH_2)_v$—, $R^{7b}COO(CH_2)_v$—, $R^{7b}OCO(CH_2)_v$—, phenyl or substituted phenyl where the substituents are from 1 to 3 of halogen, $C_1$-$C_6$ alkyl, $C_1$-$C_6$ alkoxy, or hydroxy;

$R^{7a}$ and $R^{7b}$ are independently hydrogen, $C_1$-$C_6$ alkyl, substituted $C_1$-$C_6$ alkyl, where the substituents are phenyl and v is 0 to 2;

$R^{3a}$ and $R^{3b}$ are independently hydrogen, $R^9$, $C_1$-$C_6$ alkyl substituted with $R^9$, phenyl substituted with $R^9$ or phenoxy substituted with $R^9$ with the proviso that either $R^{3a}$ or $R^{3b}$ must be a substituent other than hydrogen;

$R^9$ is:
$R^{4b}R^{12a}NCON(R^{12b})(CH_2)_v$—,
$R^{4b}R^{12a}NCSN(R^{12b})(CH_2)_v$—,
$R^{4b}R^{12a}NN(R^{12b})CON(R^{12c})(CH_2)_v$—,
$R^{4b}R^{12a}NN(R^{12b})COO(CH_2)_v$—,
$R^{4b}R^{12a}NCOO(CH_2)_v$—, or $R^{13}O$-$CON(R^{12b})(CH_2)_v$—,
where v is 0 to 2;

$R^{12a}$, $R^{12b}$ and $R^{12c}$ are independently $R^{5a}$ or $OR^{5a}$ or $R^{12a}$ and $R^{12b}$, or $R^{12b}$ and $R^{12c}$, or $R^{13}$ and $R^{12b}$ or $R^{12a}$ and $R^{4b}$ can be taken together to form —$(CH_2)_r$—B—$(CH_2)_s$— where B is $CHR^1$, O, $S(O)_m$ or $NR^{10}$, m is 0, 1 or 2, r and s are independently 0 to 2, $R^1$ is as defined above, and $R^{10}$ is hydrogen, $C_1$-$C_6$ alkyl or $C_1$-$C_5$ alkanoyl-$C_1$-$C_6$ alkyl;

$R^{13}$ is: $C_1$-$C_6$ alkyl, substituted $C_1$-$C_6$ alkyl, where the substituents are phenyl or substituted phenyl; phenyl or substituted phenyl where the substituents on the phenyl are from 1 to 3 of halogen, $C_1$-$C_6$ alkyl, $C_1$-$C_6$ alkoxy or hydroxy;

$R^4$, $R^{4b}$, $R^5$ and $R^{5a}$ are independently hydrogen, $C_1$-$C_{10}$ alkyl, substituted $C_1$-$C_{10}$ alkyl, where the substituents on the alkyl are from 1 to 5 of hydroxy, $C_1$-$C_6$ alkoxy, fluoro, $R^1$ substituted or $R^1$, $R^2$ independently disubstituted phenyl, $C_1$-$C_{20}$-alkanoyloxy, $C_1$-$C_5$ alkoxycarbonyl or carboxy;

$R^6$ is hydrogen or $C_1$-$C_{10}$ alkyl;
A is

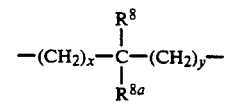

where x and y are independently 0-2;

$R^8$ and $R^{8a}$ are independently hydrogen, $C_1$-$C_{10}$ alkyl, substituted $C_1$-$C_{10}$ alkyl where the substituents are from 1 to 3 of imidazolyl, indolyl, hydroxy, fluoro, $S(O)_mR^{7a}$, $C_1$-$C_6$ alkoxy, $R^1$ substituted or $R^1$, $R^2$ independently disubstituted phenyl, $C_1$-$C_5$-alkanoyloxy, $C_1$-$C_5$ alkoxycarbonyl, carboxy; or $R^8$ and $R^{8a}$ can be taken together to form —$(CH_2)_t$— where t is 2; or $R^8$ and $R^{8a}$ can independently be joined to one or both of $R^4$ and $R^5$ to form alkylene bridges between the terminal nitrogen and the alkyl portion of the A group wherein the bridge contains from 1 to 5 carbon atoms; and pharmaceutically acceptable salts thereof.

4. A compound of claim 3 wherein:
n is 0;
p is 0 to 2;
q is 1;
w is 1;
m is 0 or 1;
$R^1$, $R^2$, $R^{1a}$, $R^{2a}$, $R^{1b}$, and $R^{2b}$ are independently hydrogen, halogen, $C_1-C_7$ alkyl, $C_1-C_3$ perfluoroalkyl, $-S(O)_mR^{7a}$, $R^{7b}O(CH_2)_v-$, $R^{7b}COO(CH_2)_v-$, phenyl or substituted phenyl where the substituents are from 1 to 3 of halogen, $C_1-C_6$ alkyl, $C_1-C_6$ alkoxy, or hydroxy; $R^{7a}$ and $R^{7b}$ are independently hydrogen, $C_1-C_6$ alkyl, substituted $C_1-C_6$ alkyl, where the substituents are phenyl and v is 0 or 1;
$R^{3a}$ and $R^{3b}$ are independently hydrogen, $R^9$, or $C_1-C_6$ alkyl substituted with $R^9$ with the proviso that either $R^{3a}$ or $R^{3b}$ must be a substituent other than hydrogen;
$R^9$ is:
$R^{4b}R^{12a}NCON(R^{12b})(CH_2)_v-$,
$R^{4b}R^{12a}NN(R^{12b})CON(R^{12c})(CH_2)_v-$,
$R^{4b}R^{12a}NN(R^{12b})COO(CH_2)_v-$,
$R^{4b}R^{12a}NCOO(CH_2)_v-$ or $R^{13}OCON(R^{12b})(CH_2)_v-$,
where v is 0 to 1;
$R^{12a}$, $R^{12b}$ and $R^{12c}$ are independently $R^{5a}$. $R^{12a}$ and $R^{12b}$, or $R^{12b}$ and $R^{12c}$, or $R^{13}$ and $R^{12b}$ or $R^{12a}$ and $R^{4b}$ can be taken together to form $-(CH_2)_r-B-(CH_2)_s-$ where B is $CHR^1$, O, $S(O)_m$ or $NR^{10}$, m is 0, 1 or 2, r and s are independently 0 to 2, $R^1$ is as defined above and $R^{10}$ is hydrogen, $C_1-C_6$ alkyl or $C_1-C_5$ alkanoyl-$C_1-C_6$ alkyl;
$R^{13}$ is: $C_1-C_6$ alkyl, substituted $C_1-C_6$ alkyl, where the substituents are phenyl or substituted phenyl; phenyl or substituted phenyl where the substituents on the phenyl are from 1 to 3 of halogen, $C_1-C_6$ alkyl, $C_1-C_6$ alkoxy or hydroxy;
$R^4$, $R^{4b}$, $R^5$, and $R^{5a}$ are independently hydrogen, $C_1-C_{10}$ alkyl, substituted $C_1-C_{10}$ alkyl, where the substituents on the alkyl are from 1 to 3 of hydroxy, $C_1-C_3$ alkoxy, fluoro, $R^1$ substituted or $R^1$, $R^2$ independently disubstituted phenyl, $C_1-C_{20}$ alkanoyloxy, $C_1-C_5$ alkoxycarbonyl or carboxy;
$R^6$ is hydrogen;
A is

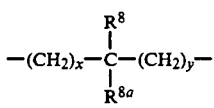

where x and y are independently 0-1;
$R^8$ and $R^{8a}$ are independently hydrogen, $C_1-C_{10}$ alkyl, substituted $C_1-C_{10}$ alkyl where the substituents are from 1 to 3 of imidazolyl, indolyl, hydroxy, fluoro, $S(O)_mR^{7a}$, $C_1-C_6$ alkoxy, $R^1$ substituted or $R^1$, $R^2$ independently disubstituted phenyl, $C_1-C_5$-alkanoyloxy, $C_1-C_5$ alkoxycarbonyl, carboxy; or $R^8$ and $R^{8a}$ can be taken together to form $-(CH_2)_t-$ where t is 2; and $R^8$ and $R^{8a}$ can independently be joined to one or both of $R^4$ and $R^5$ to form alkylene bridges between the terminal nitrogen and the alkyl portion of the A group wherein the bridge contains from 1 to 5 carbon atoms;
and pharmaceutically acceptable salts thereof.

5. A stereospecific compound of claim 1 having the following structural formula:

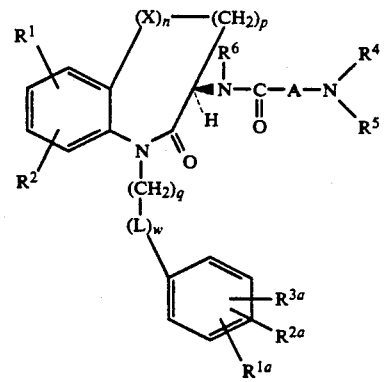

where $R^1$, $R^2$, X, n, p, q, L, w, $R^{1a}$, $R^{2a}$, $R^{3a}$, $R^4$, $R^5$, $R^6$, and A are as defined in claim 1.

6. A compound of claim 1 which is:
N-[1-[[2'-[(Methoxycarbonyl)amino][1,1'-biphenyl]-4-yl]methyl]-2,3,4,5-tetrahydro-2-oxo-1H-1-benzazepin-3(R)-yl]-3-amino-3-methylbutanamide;
N-[1-[[2'-[(Methylaminocarbonyl)amino][1,1'-biphenyl]-4-yl]methyl]-2,3,4,5-tetrahydro-2-oxo-1H-1-benzazepin-3(R)-yl]-3-amino-3-methylbutanamide;
N-[1-[[2'-[(Ethylaminocarbonyl)amino][1,1'-biphenyl]-4-yl]methyl]-2,3,4,5-tetrahydro-2—oxo-1H-1-benzazepin-3(R)-yl]-3-amino-3-methylbutanamide;
N-[1-[[2'-[(2-Propylaminocarbonyl)amino][1,1'-biphenyl]-4-yl]methyl]-2,3,4,5-tetrahydro-2-oxo-1H-1-benzazepin-3(R)-yl]-3-amino-3-methylbutanamide;
N-[1-[[2'-[(Aminocarbonyl)amino][1,1'-biphenyl]-4-yl]methyl]-2,3,4,5-tetrahydro-2-oxo-1H-1-benzazepin-3(R)-yl]-3-amino-3-methylbutanamide;
N-[1-[[2'-[(Morpholinocarbonyl)amino][1,1'-biphenyl]-4-yl]methyl]-2,3,4,5-tetrahydro-2-oxo-1H-1-benzazepin-3(R)-yl]-3-amino-3-methylbutanamide;
N-[1-[[2'-[(Piperazino)carbonyl)amino][1,1'-biphenyl]-4-yl]methyl]-2,3,4,5-tetrahydro-2-oxo-1H-1-benzazepin-3(R)-yl]-3-amino-3-methylbutanamide;
N-[1-[[2'-[[(2-Hydroxyethylamino)carbonyl]amino][1,1'-biphenyl]-4-yl]methyl]-2,3,4,5-tetrahydro-2-oxo-1H-1-benzazepin-3(R)-yl]-3-amino-3-methylbutanamide;
N-[1-[[2'-[[(2-Hydroxypropylamino)carbonyl]amino][1,1'-biphenyl]-4-yl]methyl]-2,3,4,5-tetrahydro-2-oxo-1H-1-benzazepin-3(R)-yl]-3-amino-3-methylbutanamide;
N-[1-[[2'-[(Methylaminocarbonyl)oxy][1,1'-biphenyl]-4-yl]methyl]-2,3,4,5-tetrahydro-2-oxo-1H-1-benzazepin-3(R)-yl]-3-amino-3-methylbutanamide;
N-[1-[[2'-[(Dimethylaminocarbonyl)amino][1,1'-biphenyl]-4-yl]methyl]-2,3,4,5-tetrahydro-2-oxo-1H-1-benzazepin-3(R)-yl]-3-amino-3-methylbutanamide;
N-[1-[[2'-[[(2(R)-Hydroxypropylamino)carbonyl]amino][1,1'-biphenyl]-4-yl]methyl]-2,3,4,5-tetrahydro-2-oxo-1H-1-benzazepin-3(R)-yl]-3-amino-3-methylbutanamide;
N-[1-[[2'-[[(2(S)-Hydroxypropylamino)carbonyl]amino][1,1'-biphenyl]-4-yl]methyl]-2,3,4,5-tetrahydro-2-oxo-1H-1-benzazepin-3(R)-yl]-3-amino-3-methylbutanamide;

N-[1-[[2'-[[(1-Hydroxyprop-2(R)-ylamino)carbonyl]amino][1,1'-biphenyl]-4-yl]methyl]-2,3,4,5-tetrahydro-2-oxo-1H-1-benzazepin-3(R)-yl]-3-amino-3-methylbutanamide;

N-[1-[[2'-[4-[(Methylaminocarbonyl)amino]phenoxy][1,1'-biphenyl]-4-yl]methyl]-2,3,4,5-tetrahydro-2-oxo-1H-1-benzazepin-3(R)-yl]-3-amino-3-methylbutanamide;

N-[1-[[2'-[2-[(Methylaminocarbonyl)amino]phenoxy][1,1'-biphenyl]-4-yl]methyl]-2,3,4,5-tetrahydro-2-oxo-1H-1-benzazepin-3(R)-yl]-3-amino-3-methylbutanamide;

N-[1-[[2'-[(Aminocarbonyl)amino][1,1'-biphenyl]-4-yl]methyl]-2,3,4,5-tetrahydro-2-oxo-1H-1-benzazepin-3(R)-yl]-3-(2(R)-hydroxypropyl)amino-3-methylbutanamide;

N-[1-[[2'-[(Aminocarbonyl)amino][1,1'-biphenyl]-4-yl]methyl]-2,3,4,5-tetrahydro-2-oxo-1H-1-benzazepin-3(R)-yl]-3-[2(S),3-dihydroxypropyl]amino-3-methylbutanamide;

N-[1-[[2'-[(Methylaminocarbonyl)amino][1,1'-biphenyl]-4-yl]methyl]-2,3,4,5-tetrahydro-2-oxo-1H-1-benzazepin-3(R)-yl]-3-(2(R)-hydroxypropyl)amino-3-methylbutanamide;

N-[1-[[2'-[(Methylaminocarbonyl)amino][1,1'-biphenyl]-4-yl]methyl]-2,3,4,5-tetrahydro-2-oxo-1H-1-benzazepin-3(R)-yl]-3-(2(S)-hydroxypropyl)amino-3-methylbutanamide;

N-[1-[[2'-[(Methylaminocarbonyl)amino][1,1'-biphenyl]-4-yl]methyl]-2,3,4,5-tetrahydro-2-oxo-1H-1-benzazepin-3(R)-yl]-3-[2(S),3-dihydroxypropyl]amino-3-methylbutanamide;

N-[1-[[2'-[(Morpholinocarbonyl)amino][1,1'-biphenyl]-4-yl]methyl]-2,3,4,5-tetrahydro-2-oxo-1H-1-benzazepin-3(R)-yl]-3-(2(R)-hydroxypropyl)amino-3-methylbutanamide;

N-[1-[[2'-[(Morpholinocarbonyl)amino][1,1'-biphenyl]-4-yl]methyl]-2,3,4,5-tetrahydro-2-oxo-1H-1-benzazepin-3(R)-yl]-3-[2(S),3-dihydroxypropyl]amino-3-methylbutanamide;

N-[1-[[2'-[[(2-Hydroxyethylamino)carbonyl]amino][1,1'-biphenyl]-4-yl]methyl]-2,3,4,5-tetrahydro-2-oxo-1H-1-benzazepin-3(R)-yl]-3-(2(R)-hydroxypropyl)amino-3-methylbutanamide;

N-[1-[[2'-[[(2-Hydroxyethylamino)carbonyl]amino][1,1'-biphenyl]-4-yl]methyl]-2,3,4,5-tetrahydro-2-oxo-1H-1-benzazepin-3(R)-yl]-3-(2(S)-hydroxypropyl)amino-3-methylbutanamide;

N-[1-[[2'-[[(2-Hydroxyethylamino)carbonyl]amino][1,1'-biphenyl]-4-yl]methyl]-2,3,4,5-tetrahydro-2-oxo-1H-1-benzazepin-3(R)-yl]-3-[2(S),3-dihydroxypropyl]amino-3-methylbutanamide;

N-[1-[[2'-[(Methylaminocarbonyl)amino][1,1'-biphenyl]-4-yl]methyl]-2,3,4,5-tetrahydro-2-oxo-1H-1-benzazepin-3(R)-yl]-2-amino-2-methylpropanamide;

N-[1-[[2'-[(Aminocarbonyl)amino][1,1'-biphenyl]-4-yl]methyl]-2,3,4,5-tetrahydro-2-oxo-1H-1-benzazepin-3(R)-yl]-2-amino-2-methylpropanamide;

N-[1-[[2'-[(Morpholinocarbonyl)amino][1,1'-biphenyl]-4-yl]methyl]-2,3,4,5-tetrahydro-2-oxo-1H-1-benzazepin-3(R)-yl]-2-amino-2-methylpropanamide;

N-[1-[[2'-[(Piperazinocarbonyl)amino][1,1'-biphenyl]-4-yl]methyl]-2,3,4,5-tetrahydro-2-oxo-1H-1-benzazepin-3(R)-yl]-2-amino-2-methylpropanamide;

N-[1-[[2'-[[(2-Hydroxyethylamino)carbonyl]amino][1,1'-biphenyl]-4-yl]methyl]-2,3,4,5-tetrahydro-2-oxo-1H-1-benzazepin-3(R)-yl]-2-amino-2-methylpropanamide;

N-[1-[[2'-[(Methylaminocarbonyl)oxy][1,1'-biphenyl]-4-yl]methyl]-2,3,4,5-tetrahydro-2-oxo-1H-1-benzazepin-3(R)-yl]-2-amino-2-methylpropanamide;

N-[1-[[2'-[[(Methoxycarbonylmethylamino)carbonyl]amino][1,1'-biphenyl]-4-yl]methyl]-2,3,4,5-tetrahydro-2-oxo-1H-1-benzazepin-3(R)-yl]-2-amino-2-methylpropanamide;

N-[1-[[2'-[(Hydroxyaminocarbonyl)amino][1,1'-biphenyl]-4-yl]methyl]-2,3,4,5-tetrahydro-2-oxo-1H-1-benzazepin-3(R)-yl]-2-amino-2-methylpropanamide;

N-[1-[[2'-[(Methoxycarbonyl)amino][1,1'-biphenyl]-4-yl]methyl]-7-fluoro-2,3,4,5-tetrahydro-2-oxo-1H-1-benzazepin-3(R)-yl]-3-amino-3-methylbutanamide;

N-[1-[[2'-[(Methylaminocarbonyl)amino][1,1'-biphenyl]-4-yl]methyl]-7-fluoro-2,3,4,5-tetrahydro-2-oxo-1H-1-benzazepin-3(R)-yl]-3-amino-3-methylbutanamide;

N-[1-[[2'-[(Methylaminocarbonyl)amino][1,1'-biphenyl]-4-yl]methyl]-7-trifluoromethyl-2,3,4,5-tetrahydro-2-oxo-1H-1-benzazepin-3(R)-yl]-3-amino-3-methylbutanamide;

N-[1-[[2'-[(Morpholinocarbonyl)amino][1,1'-biphenyl]-4-yl]methyl]-7-trifluoromethyl-2,3,4,5-tetrahydro-2-oxo-1H-1-benzazepin-3(R)-yl]-3-amino-3-methylbutanamide;

N-[1-[[2'-[[(2-Hydroxyethylamino)carbonyl]amino][1,1'-biphenyl]-4-yl]methyl]-7-trifluoromethyl-2,3,4,5-tetrahydro-2-oxo-1H-1-benzazepin-3(R)-yl]-3-amino-3-methylbutanamide;

N-[1-[[2'-[[(2-Hydroxyethylamino)carbonyl]amino][1,1'-biphenyl]-4-yl]methyl]-7-fluoro-2,3,4,5-tetrahydro-2-oxo-1H-1-benzazepin-3(R)-yl]-3-amino-3-methylbutanamide;

N-[1-[[2'[(Methylaminocarbonyl)oxy][1,1'-biphenyl]-4-yl]methyl]-7-fluoro-2,3,4,5-tetrahydro-2-oxo-1H-1-benzazepin-3(R)-yl]-3-amino-3-methylbutanamide;

N-[1-[[2'-[2-[(Methylaminocarbonyl)amino]phenoxy][1,1'-biphenyl]-4-yl]methyl]-7-trifluoromethyl-2,3,4,5-tetrahydro-2-oxo-1H-1-benzazepin-3(R)-yl]-3-amino-3-methylbutanamide;

N-[1-[[2'-[(Methylaminocarbonyl)amino][1,1'-biphenyl]-4-yl]methyl]-7-fluoro-2,3,4,5-tetrahydro-2-oxo-1H-1-benzazepin-3(R)-yl]-3-(2(R)-hydroxypropyl)amino-3-methylbutanamide;

N-[1-[[2'-[(Methylaminocarbonyl)amino][1,1'-biphenyl]-4-yl]methyl]-7-fluoro-2,3,4,5-tetrahydro-2-oxo-1H-1-benzazepin-3(R)-yl]-3-[2(S),3-dihydroxypropyl]amino-3-methylbutanamide;

N-[1-[[2'-[(Morpholinocarbonyl)amino][1,1'-biphenyl]-4-yl]methyl]-7-fluoro-2,3,4,5-tetrahydro-2-oxo-1H-1-benzazepin-3(R)-yl]-3-(2(R)-hydroxypropyl)amino-3-methylbutanamide;

N-[1-[[2'-[(Morpholinocarbonyl)amino][1,1'-biphenyl]4-yl]methyl]-7-fluoro-2,3,4,5-tetrahydro-2-oxo-1H-1-benzazepin-3(R)-yl]-3-[2(S),3-dihydroxypropyl]amino-3-methylbutanamide;

N-[1-[[2'-[[(2-Hydroxyethylamino)carbonyl]amino][1,1'-biphenyl]-4-yl]methyl]-7-fluoro-2,3,4,5-tetrahydro-2-oxo-1H-1-benzazepin-3(R)-yl]-3-(2(R)-hydroxypropyl)amino-3-methylbutanamide;

N-[1-[[2'-[(Methylaminocarbonyl)amino][1,1'-biphenyl]-4-yl]methyl]-7-fluoro-2,3,4,5-tetrahydro-2- oxo-1H-1-benzazepin-3(R)-yl]-2-amino-2-methylpropanamide;

N-[1-[[2'-[(Morpholinocarbonyl)amino][1,1'-biphenyl]-4-yl]methyl]-7-fluoro-2,3,4,5-tetrahydro-2-oxo-1H-1-benzazepin-3(R)-yl]-2-amino-2-methylpropanamide;

N-[1-[[2'-[(Piperazinocarbonyl)amino][1,1'-biphenyl]-4-yl]methyl]-7-fluoro-2,3,4,5-tetrahydro-2-oxo-1H-1-benzazepin-3(R)-yl]-2-amino-2-methylpropanamide;

N-[1-[[2'-[[(2-Hydroxyethylamino)carbonyl]amino][1,1'-biphenyl]-4-yl]methyl]-7-fluoro-2,3,4,5-tetrahydro-2-oxo-1H-1-benzazepin-3(R)-yl]-2-amino-2-methylpropanamide; or N-[1-[[2'-[(Methylaminocarbonyl)oxy][1,1'-biphenyl]-4-yl]methyl]-7-fluoro-2,3,4,5-tetrahydro-2-oxo-1H-1-benzazepin-3(R)-yl]-2-amino-2-methylpropanamide.

7. A method for increasing levels of endogenous growth hormone in a human or an animal which comprises administering to such human or animal an effective amount of a compound of claim 1.

8. A composition useful for increasing the endogenous production or release of growth hormone in a human or an animal which comprises an inert carrier and an effective amount of a compound of claim 1.

* * * * *

UNITED STATES PATENT AND TRADEMARK OFFICE
CERTIFICATE OF CORRECTION

PATENT NO. : 5,283,241

DATED : February 1, 1994

INVENTOR(S) : Richard J. Bochis, Matthew J. Wyvratt and William R. Schoen

It is certified that error appears in the above-indentified patent and that said Letters Patent is hereby corrected as shown below:

In the Abstract, right column, title page; column 2, line 19; and column 79, line 2, in the structural formula, replace " $(X_n$ " with -- $(X)_n$ --.

Signed and Sealed this

Twenty-fifth Day of October, 1994

Attest:

BRUCE LEHMAN

*Attesting Officer*     *Commissioner of Patents and Trademarks*